US009607724B2

(12) United States Patent
Adler

(10) Patent No.: US 9,607,724 B2
(45) Date of Patent: *Mar. 28, 2017

(54) DEVICES PROCESSED USING X-RAYS

(71) Applicant: David Lewis Adler, San Jose, CA (US)

(72) Inventor: David Lewis Adler, San Jose, CA (US)

(73) Assignee: SVXR, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/732,674

(22) Filed: Jun. 6, 2015

(65) Prior Publication Data

US 2015/0270023 A1    Sep. 24, 2015

Related U.S. Application Data

(63) Continuation of application No. 13/987,808, filed on Sep. 4, 2013, now Pat. No. 9,129,715.

(60) Provisional application No. 61/743,458, filed on Sep. 5, 2012, provisional application No. 61/852,061, filed on Mar. 15, 2013.

(51) Int. Cl.
*G21K 7/00* (2006.01)
*G01N 23/04* (2006.01)

(52) U.S. Cl.
CPC ............... *G21K 7/00* (2013.01); *G01N 23/04* (2013.01); *G21K 2207/005* (2013.01)

(58) Field of Classification Search
CPC .... G21K 7/00; G21K 2207/005; G01N 23/04; G01N 21/93; G01N 21/9501; H01L 23/49827; H01L 23/481; G06T 7/0004
See application file for complete search history.

(56) References Cited

U.S. PATENT DOCUMENTS 1,203,495 A    10/1916  Coolidge
1,211,092 A     1/1917  Coolidge
(Continued)

FOREIGN PATENT DOCUMENTS

EP    1126477 A2    8/2001
EP    2063261 A1    9/2009
WO   98/35214 A2    8/1998

OTHER PUBLICATIONS

W.C. Röntgen, Ueber eine neue Art von Strahlen (Würzburg Verlag, Würzburg, Germany, 1896); In English as: W.C. Röntgen, "On a New Kind of Rays," Nature, vol. 53, pp. 274-276 (Jan. 23 1896).
(Continued)

*Primary Examiner* — Courtney Thomas
(74) *Attorney, Agent, or Firm* — Baker Botts L.L.P.

(57) ABSTRACT

Objects undergoing processing by a high resolution x-ray microscope with a high flux x-ray source that allows high speed metrology or inspection of objects such as integrated circuits (ICs), printed circuit boards (PCBs), and other IC packaging technologies. The object to be investigated is illuminated by collimated, high-flux x-rays from an extended source having a designated x-ray spectrum. The system also comprises a stage to control the position and orientation of the object; a scintillator that absorbs x-rays and emits visible photons positioned in very close proximity to (or in contact with) the object; an optical imaging system that forms a highly magnified, high-resolution image of the photons emitted by the scintillator; and a detector such as a CCD array to convert the image to electronic signals.

24 Claims, 27 Drawing Sheets

(56) References Cited

U.S. PATENT DOCUMENTS

| | | | |
|---|---|---|---|
| 1,215,116 | A | 1/1917 | Coolidge |
| 1,328,495 | A | 1/1920 | Coolidge |
| 1,355,126 | A | 10/1920 | Coolidge |
| 2,617,942 | A | 11/1952 | McLachlan, Jr. |
| 2,814,729 | A | 11/1957 | Newberry |
| 2,877,353 | A | 3/1959 | Newberry |
| 3,778,614 | A | 12/1973 | Hounsfield |
| 3,973,127 | A | 8/1976 | Matsuda et al. |
| 4,115,698 | A | 9/1978 | Hounsfield |
| 4,144,457 | A | 3/1979 | Albert |
| 4,317,036 | A | 2/1982 | Wang |
| 4,870,674 | A | 9/1989 | Schmahl |
| 5,045,696 | A | 9/1991 | Hirose |
| 5,222,113 | A | 6/1993 | Thieme et al. |
| 5,276,724 | A | 1/1994 | Kumasaka et al. |
| 5,434,901 | A | 7/1995 | Nagai et al. |
| 5,550,887 | A | 8/1996 | Schmal |
| 5,912,939 | A | 6/1999 | Hirsch |
| 6,002,740 | A | 12/1999 | Cerrina |
| 6,091,796 | A | 7/2000 | Trissel et al. |
| 6,526,121 | B1 | 2/2003 | Hwu et al. |
| 6,672,761 | B2 | 1/2004 | Sykes et al. |
| 6,859,516 | B2 | 2/2005 | Schneider et al. |
| 6,886,153 | B1 | 4/2005 | Bevis |
| 7,057,187 | B1 | 6/2006 | Yun et al. |
| 7,099,729 | B2 | 8/2006 | Tai et al. |
| 7,119,953 | B2 | 10/2006 | Yun |
| 7,130,375 | B1 | 10/2006 | Yun et al. |
| 7,142,992 | B1 | 11/2006 | Huet et al. |
| 7,215,736 | B1 | 5/2007 | Wang et al. |
| 7,297,959 | B2 | 11/2007 | Yun et al. |
| 7,309,161 | B1 | 12/2007 | Eliasson |
| 7,388,942 | B2 | 6/2008 | Wang et al. |
| 7,394,890 | B1 | 7/2008 | Wang et al. |
| 7,443,953 | B1 | 10/2008 | Yun et al. |
| 7,561,662 | B2 | 7/2009 | Wang et al. |
| 7,800,072 | B2 | 9/2010 | Yun et al. |
| 7,813,475 | B1 | 10/2010 | Wu et al. |
| 7,877,722 | B2 | 1/2011 | Duffy |
| 8,139,846 | B2 | 3/2012 | Bajura et al. |
| 8,831,179 | B2 | 9/2014 | Adler et al. |
| 8,995,622 | B2 | 3/2015 | Adler et al. |
| 2008/0061234 | A1 | 3/2008 | Nakamura |
| 2012/0269323 | A1 | 10/2012 | Adler et al. |
| 2012/0269324 | A1 | 10/2012 | Adler |
| 2012/0269325 | A1 | 10/2012 | Adler et al. |
| 2012/0269326 | A1 | 10/2012 | Adler et al. |
| 2013/0032947 | A1* | 2/2013 | Park ............ H01L 21/568 257/774 |
| 2014/0064445 | A1* | 3/2014 | Adler ............ G21K 7/00 378/43 |
| 2014/0301630 | A1 | 10/2014 | Kulkarni |

OTHER PUBLICATIONS

Janos Kirz, "Phase zone plates for x rays and the extreme uv", J. Opt. Soc. Am. vol. 64(3), pp. 301-309 (Mar. 1974).

G. Schmahl et al., "Zone Plates for X-Ray Microscopy ", Ch. 8 of "X-Ray Microscopy", G. Schmahl et al., eds., pp. 63-74 (Springer Verlag, Berlin, 1984).

D. Rudolph et al., "The Göttingen X-Ray Microscope and X-Ray Microscopy Experiments at the BESSY Storage Ring", Ch. 20 of "X-Ray Microscopy", G. Schmahl et al., eds., pp. 192-202 (Springer Verlag, Berlin, 1984).

Malcolm R. Howells, Janos Kirz and David Sayre, "X-ray Microscopes" Scientific American vol. 264(2), pp. 88-94 (Feb. 1991).

"Standard Test Method for Measurement of Focal Spots of Industrial X-Ray Tubes by Pinhole Imaging," Standard SE-1165, ASTM Committee E-7 on Nondestructive Testing (May 15, 1992).

A.D. Dubner et al., "Diffraction effects in x-ray proximity printing", J. Vac. Sci. Technol. B, vol. 10(5), pp. 2234-2242 (Sep./Oct. 1992).

Henry I. Smith and M.L. Schattenberg, "X-ray lithography from 500 to 30 nm: X-ray nanolithography", IBM J. Res. Develop. vol. 37(3), p. 319-329 (May 1993).

Gelsomina De Stasio et al., "Soft-x-ray transmission photoelectron spectromicroscopy with the MEPHISTO system", Rev. Sci. Instrum. vol. 69(9), pp. 3106-3108 (Sep. 1998).

Gelsomina De Stasio et al., "MEPHISTO spectromicroscope reaches 20 nm lateral resolution", Rev. Sci. Instrum. vol. 70(3), pp. 1740-1742 (Mar. 1999).

J. Kirz & D. Attwood, "Zone Plates", Sec. 4.4 of the "X-ray Data Booklet", A.C. Thompson & D. Vaughan, eds., Lawrence Berkeley National Laboratory, Berkeley, CA, (Second Edition Jan. 2001); available at < http://xdb.lbl.gov/Section4/Sec_4-4.html >.

Akira Hirakimoto, "Microfocus X-ray Computed Tomography and Its Industrial Applications", Analytical Sciences vol. 17 Supplement, pp. i123-i125 (2001).

Akihisa Takeuchi et al., "Submicrometer-resolution three-dimensional imaging with hard x-ray imaging microtomography", Rev. Sci. Instrum. vol. 73(12), pp. 4246-4249 (Dec. 2002).

S. Günther et al., "Photoelectron microscopy and applications in surface and materials science", Progress in Surface Science vol. 70, pp. 187-260 (2002).

"X-Ray Lithography towards 15 nm", Jefferson Lab Technical Note 03-016 Thomas Jefferson National Accelerator Facility, Newport News, Virginia (Jan. 2003).

Yuxin Wang et al. "A Novel X-ray Microtomography System with High Resolution and Throughput," in Technical Proceedings of the 2004 NSTI Nanotechnology Conference and Trade Show, vol. 3, pp. 503-507 (2004).

Y. Hwu, J.H. Je & G. Margaritondo, "Real-time radiology in the microscale", Nuclear Instruments and Methods in Physics Research A vol. 551, pp. 108-118 (2005).

L.A. Bakaleynikov et al., "Combined X-ray-electron Imaging Techniques: Limitations on Lateral Resolution", Journal of Electron Spectroscopy and Related Phenomena vol. 151, pp. 97-104 (2005).

Thierry Martin & Andreas Koch, "Recent developments in X-ray imaging with micrometer spatial resolution" Journal of Synchrotron Radiation vol. 13, pp. 180-194 (2006).

Oded Rabin et al., "An X-ray computed tomography imaging agent based on long-circulating bismuth sulphide nanoparticles", Nature Materials vol. 5, pp. 118-122 (Feb. 2006).

Andrei Tkachuk et al. "High-resolution x-ray tomography using laboratory sources," in Developments in X-Ray Tomography V, Proc. SPIE vol. 6318, 63181D (2006).

S.H. Lau et al. "Non destructive characterization of advanced package and die level defects—with novel 3D x-ray micro and nanotomography systems", SEMI's Semiconductor Manufacturing Magazine pp. 1-10 (Feb. 2007).

Ehrenfried Zschech et al., "Application of high resolution x-ray microscopy to image backend-of-line structures", in Smart Systems Integration 2008—2nd European Conference & Exhibition on Integration Issues of Miniaturized Systems—MOMS, MOEMS, ICS and Electronic Components, pp. 1-7 (VDE Verlag, Berlin, Germany, 2008).

J. Kirz & C. Jacobsen, "The History and Future of X-ray Microscopy" in Proc. 9th International Conf. on X-ray Microscopy 2008, J. Physics: Conf. Series vol. 186 pp. 012001 (2009).

A. Gaur, B.D. Shrivastava & S.K. Joshi, "Copper K-edge XANES of Cu(I) and Cu(II) oxide mixtures", Journal of Physics: Conference Series vol. 190, 012084 (2009).

J. A. Koch, E. Dewald, & B. Kozioziemski, "X-ray source brightness comparison: Rigaku rotating anode source vs. Kevex microfocus tube", Technical Report LLNL-TR-426090 (Lawrence Livermore National Lab, Livermore, CA Mar. 18, 2010).

S.J. Liew, A.A. Malcolm, X.M. Yin, & C.S. Chong, "User-friendly visualisation of industrial X-ray computed tomography", SIMTech Technical Reports vol. 11, No. 2, pp. 92-98 (Apr.-Jun. 2010).

Dong Woo Chang et al., "Real time observation of mouse fetal skeleton using a high resolution X-ray synchrotron", J. Vet. Sci. vol. 12(2), pp. 107-113 (2011).

Roger Falcone et al., "New Directions in X-ray Microscopy", Contemp. Phys. vol. 52(4) pp. 293-318 (Jul.-Aug. 2011).

(56) References Cited

OTHER PUBLICATIONS

S. Pattnaik, S. K. Kamila, G. S. Roy, R. Das, & N. K. Sharma, "Two Point Resolution: An Introspection", Researcher vol. 3, No. 2, pp. 66-72 (2011).

Klaus Bavendiek et al., "New Measurement Methods of Focal Spot Size and Shape of X-ray Tubes in Digital Radiological Applications in Comparison to Current Standards" in Proceedings 18th World Conference on Nondestructive Testing, (Apr. 16-20, 2012, Durban, South Africa) (South African Institute for Non-Destructive Testing (SAINT), Pretoria, South Africa).

XD7600NT Data sheet, Nordson DAGE Holdings Ltd. of Aylesbury, Buckinghamshire UK. < http://www.nordson.com/EN-US/DIVISIONS/DAGE/PRODUCTS/EXAMPLEPRODUCTDAMILY/Pages/ XD7600NTDiamondFp.aspx > 1st noted upload May 19, 2011.

Xilinx Virtex 7 chip, Xilinx, Corp, San Jose, CA < http://www.xilinx.com/products/silicon-devices/3dic/index.htm >. 1st noted upload: Aug. 6, 2013.

\* cited by examiner

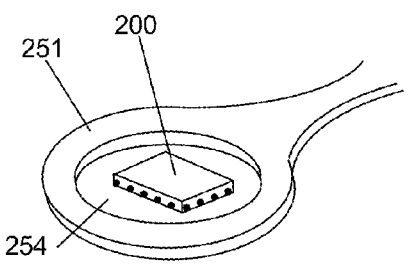 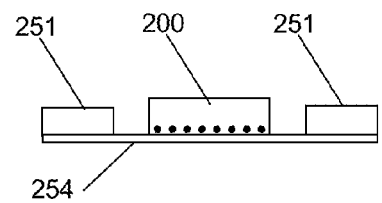
FIG. 12A      FIG. 12B
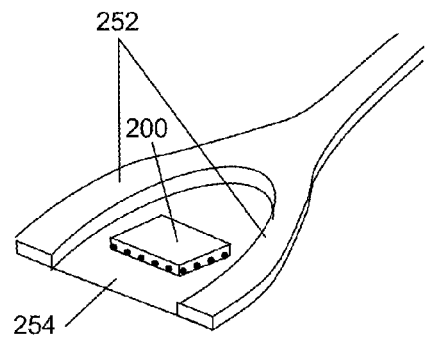 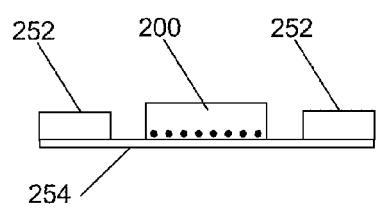
FIG. 13A      FIG. 13B
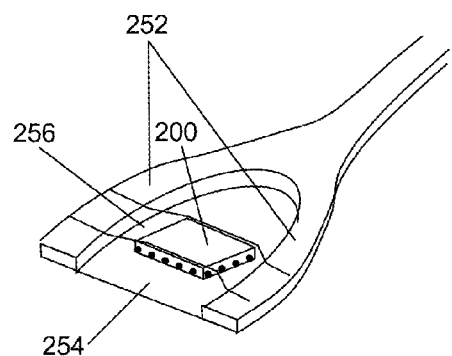 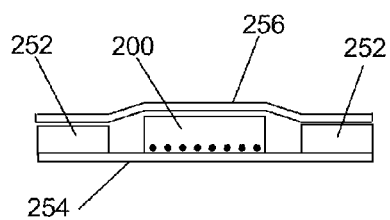
FIG. 14A      FIG. 14B

DEVICES PROCESSED USING X-RAYS

RELATED INVENTIONS

The present application is a Continuation of U.S. patent application Ser. No. 13/987,808, filed Sep. 4, 2013 and entitled HIGH SPEED X-RAY INSPECTION MICROSCOPE, which in turn claims the benefit of U.S. Provisional Application No. 61/743,458, filed on Sep. 5, 2012 and entitled X-RAY INSPECTION MICROSCOPE, and also claims the benefit of U.S. Provisional Application No. 61/852,061, filed on Mar. 15, 2013 and entitled X-RAY INSPECTION MICROSCOPE, both of which are herein incorporated by reference.

FIELD OF THE INVENTION

This invention relates to the high-speed examination and inspection of objects using x-rays that have structures of interest on the micrometer to nanometer scale. Such objects include integrated circuits (ICs) and integrated circuit packaging, including multi-chip packages (MCPs) with silicon interposers and through-silicon vias (TSVs). Certain natural objects (crystals or quasi-crystals) or biological structures may also be examined using these techniques.

In particular, this high-speed examination and inspection is accomplished by illuminating the object with x-rays, and using a scintillator to convert the transmitted high-resolution x-ray pattern into a high-resolution visible light image. The high-resolution visible light images are then relayed onto a sensor, such as a charge-coupled device (CCD) camera, where they are converted into electronic signals.

Once the image has been captured electronically, it can be used as a microscope image for metrology and structural analysis. Dimensions, such as "critical dimensions" (CDs) for integrated circuit structures, can be determined by analysis of the images. Multiple images can be combined to determine 2-dimensional (2D) and 3-dimensional (3D) structures and their measurements. Due to the high-speed acquisition of the image enabled by this invention, these measurements can be used for in-process metrology, sampling either the incoming material for a manufacturing process, or items at various stages of the manufacturing process, for quality control. It can also be used for metrology after manufacturing has been completed, to ensure manufacturing specifications have been met.

High-speed metrology is the backbone of statistical process control, or SPC. SPC improves yield over simple inspection by identifying production variations before they cause a loss of product yield. In order to obtain product yields over 90%, it is often necessary to closely monitor variations in production that are not necessarily defects, but indicate process variations that can lead to defects. Using SPC it is possible to maintain very high yields.

The presence of defects within the structure can also be observed from the images, and the image can therefore be used for inspection of objects and for manufacturing process control. Defects can be detected manually, or by comparison with other areas within the object, or by comparison with stored information such as an image of a device known to be correctly manufactured. The invention can be used for detecting defects (inspection), determining the location of suspected defects (defect location) or determining the cause of known defects (failure analysis).

The high-speed metrology and inspection results can in turn be used for yield analysis of manufacturing processes (such as the fabrication of integrated circuits and other semiconductor devices), as well as for packaging technologies for those devices (such as interposers with through-silicon vias (TSVs), or multi-chip packaging (MCP) processes such as those using microbumping for assembling multiple chips into one package). The yield analysis results can in turn be used to improve yield for these and other manufacturing and packaging processes.

BACKGROUND OF THE INVENTION

Since the early days of the semiconductor industry, the observation known as "Moore's Law" has been followed by the industry. This "law" states that the number of transistors that can economically be integrated into a semiconductor device increases by a factor of 1.5 to 2.0 times every two years. The increase has generally been achieved by miniaturization of the components of the electronic device, achieved through planer scaling of the transistor and interconnect wiring, and has provided the additional benefits of continuous improvements in processing power, data storage density and functional integration of semiconductor devices and the end products of which they are critical components. The current state-of-the-art semiconductor devices are built using a minimum critical dimension of about 28 nanometers, and smaller devices are in development.

In order to reduce the size of transistors and continue to improve semiconductor performance, it is necessary to create patterns on the silicon substrate in ever decreasing dimensions. Photolithography is the most common process used to create these patterns. The minimum feature size that can be lithographically patterned is generally limited to a factor of the wavelength of the illumination source. The state of the art illumination source used in lithographic manufacturing today uses illumination at a wavelength of 193 nanometers. In order to produce 28 nanometer features, a number of improvements have been employed, including the use of immersion optics to increase the numerical aperture (NA) of the lithographic system, the use of design modifications for the photomask, sometimes called optical proximity correction (OPC), to improve final image fidelity, and the use of multiple photo-exposures for patterning a single layer. These techniques, while making sub-wavelength patterning possible, add significant cost to the process.

Although single functional transistors with gate dimensions as small as 5 nm in size have been demonstrated, and manufacturing techniques have been proposed to enable large-scale patterning for devices with dimensions smaller than 10 nm, the cost effectiveness and commercial feasibility of these solutions have yet to be demonstrated.

An alternative to device shrinking that can enable the functional integration of ever greater numbers of semiconductor devices in a cost effective manner is the utilization of techniques that connect integrated devices vertically. New methods of attaching integrated circuits (ICs) to each other and to printed circuit boards (PCBs) are now being introduced. These new methods include silicon interposers and through-silicon vias (TSVs), so-called "3D IC" and "2.5D IC" technologies. The interconnections used for 3D and 2.5D packaging between stacked IC or semiconductor devices are much smaller than for PCBs. While PCBs rarely use interconnections smaller than a 50 micron minimum pitch dimension, commercial TSV packages can have diameters as small as 2 microns, and silicon interposers can have features with dimensions below 100 nanometers. Interposers can also be manufactured from glass, or a composite of organic material with fiberglass or a particle filler such as silica.

Integrated circuits are often manufactured using custom processes, depending on the device being manufactured. For example, dynamic random-access memory (DRAM) chips may require a different process recipe than complementary metal-oxide-semiconductor (CMOS) logic chips if each is to be manufactured for optimum performance. In the past, if a device that needed both memory and logic was desired, a chip design using both in the same IC could be manufactured, but with a compromise that optimized the performance of neither logic nor memory. Alternatively, a printed circuit board (PCB) could be manufactured, containing both a memory and a logic chip, each manufactured for optimum performance. However, the long distances that the signals would have to travel on the PCB from chip-to-chip will slow the performance considerably. As the clock speed of logic chips has increased and multiple operating cores have been introduced, memory-access latency resulting from traditional surface mount, through-hole interconnect, ball grid arrays (BGAs), or dual in-line memory module (DIMMs) on printed circuit boards has begun to limit the performance of more and more electronic systems.

Recently, it is becoming popular to stack ICs and connect them within the same package. One example of this new packaging technology is the silicon interposer that provides interconnection between two or more semiconductor devices, a semiconductor device and a printed circuit board, or a semiconductor device and some other package component. An active silicon device may also function as an interposer in which case the structure is typically referred to as "3D IC". The interposer is typically a layer of silicon, manufactured from the same kind of silicon wafer used for the ICs themselves, in which vias that pass through the silicon have been manufactured. The vias, placed at predetermined locations, are holes filled with an electrically conducting material (such as copper (Cu)) that pass completely through the silicon. When chips are bonded to both sides of the interposer, the through-silicon vias (TSVs) allow signals from one IC to travel a relatively short distance vertically from one chip to another. When chips are bonded to a PCB using an interposer, they allow signals from the chips on one side of the interposer to connect the PCB.

Similar interposers with vias passing through the materials may also be fabricated using glass or a reinforced organic material.

These vias are typically made of copper (Cu), but processes using vias made of tungsten (W) have also been developed, and vias with a variety of metal layers are anticipated. Interposers with thickness of less than 50 microns with via diameters of about 5 microns have been demonstrated. Somewhat thicker interposers may be desirable for some manufacturing processes, but the thickness is typically limited by the practical of height to via diameter aspect ratio that can be reliably manufactured. Aspect ratio of 10:1 has been widely demonstrated and prototypes indicate aspect ratios of 20:1 are possible. A single interposer, serving as the interconnection between memory chips that can contain billions of memory cells and a logic chip for a microprocessor, can have thousands or even tens of thousands of TSVs. For thinner interposers, smaller TSV diameters (as small as 1 micron) have been proposed, allowing an even greater number of connections. Since each TSV is a vital communication link between a portion of the logic and memory chip, each TSV must function perfectly. No breakdown in communication can be allowed.

It is therefore imperative that, before the active chips are bonded together to the interposer, the interposer is known to be 100% functional. The economic need for this is clear—bonding good chips to a bad interposer ruins all the economic value invested in making the chips.

There is therefore a need to properly test and/or inspect these interposers before final bonding takes place.

Aside from interposers with TSVs, other packaging technologies are also being explored as a way to increase the number of transistors in a single package, and continue the benefits of Moore's Law.

Flip chip interconnect (FCI), sometimes called controlled collapse chip connection (or "C4"), is one such technology that is currently being used. In this process, a pad ring is connected to rows, columns or an array of solder bumps on the surface of a chip while it is still in the form of a wafer. The bumps may form an array on the surface of the chip, a partial array, or may exist in a single perimeter row around the chip or a column in the center or side. The bumps are may be aligned to either the package substrate or to another die.

In traditional processes, the individual chips are then "diced" or singulated from the wafer and placed onto a substrate which is typically composed of glass fiber reinforced epoxy (such as FR4), bismaleimide triazine (BT) or similar, but may also be ceramic or Teflon or other stable material, or even a flexible substrate such as tape. Solder flux may be first applied to the bump and or substrate contact surface or it may be a component of the solder paste applied during the process.

The bumped chip and substrate are passed through a mass reflow furnace. During this process the solder melts and re-solidifies. This melting and re-solidifying should produce the desired outcome of a reliable connection at each joint between every micro-bump and every land, pad or terminal on the associated substrate or die. Chips with about 2,000 bumps using this process have been demonstrated. The pitch of such bump arrays is typically larger than 100 microns.

After mass reflow, the solder joints created in this process may be inspected using acoustic microscopy. A sound wave is passed through the joint and either detected on the other side of the structure or reflected back to the sending side. Changes in the properties of the acoustic signal can be utilized to determine if the solder joint is normal or not.

This kind of immediate feedback provided by acoustic microscopy allows for rapid identification of problems and their correction by modification of the process, materials, and equipment used in the manufacture of such products.

Newer products are currently entering the market that require interconnect pitches of less than 100 microns. Single perimeter rows of bumps made from copper and attached to organic substrates have been demonstrated at a pitch of 50 microns, and dual rows of copper bumps attached to organic substrates have been demonstrated at a pitch of 80 microns. These chips are typically mounted to the substrate using a process known as thermo-compression bonding. As opposed to mass reflow, in thermo compression bonding, the bumped chip is aligned to the substrate, placed onto the substrate and then exposed to pressure and heat all using a single tool. Typically one chip is processed at a time, and processing times can exceed tens of seconds for each individual chip.

Newer products such as those applying silicon or other fine pitch interposers or 3D stacking of die onto active devices require a full array of contacts at pitches of 50 microns or smaller. The demands for even smaller and smaller pitch is expected to continue as chip to chip data rates expand.

For current parts being developed at this smaller bump pitch, there is no reliable non-destructive test methodology to inspect the quality of bonds formed during the bonding process. Acoustic microscopy has not demonstrated the ability to detect flaws in solder bumps at bump pitches of 50 microns and below. And, in many cases, the electrical contact points on the parts are too small even for electrical testing at this stage in the manufacturing process. So additional manufacturing steps must be performed at additional cost. In most cases, several days or weeks may be required until an electrical test is performed on an assembled package.

In many cases, due to the lack of feedback data during package assembly or bonding process, some or all of the units tested will be found to be non-functional. Current failure analysis techniques examine these failed parts mechanically, typically by using focused ion beam milling to locate the specific failed connection. The connection thus exposed can be imaged used existing scanning electron microscope techniques. The time required to create an image of a defected bond has been reported to be in the range of 1-2 weeks after electrical test due to the difficulty and time required to mill to the specific spot in question without going through or past it. This is unacceptable for high-speed production lines or package assembly.

There is therefore a need for a failure analysis technique that can non-destructively examine failed parts for process improvement, preferably in a matter of seconds, and then be used in a manufacturing line for statistical process control (SPC).

For the prior art testing of interposers, electrical probes can be used to make continuity tests of the TSVs. However, given that there may be tens of thousands of TSVs, a probe using tens of thousands of electrodes may be required. It is unclear if such a probe is even possible using standard testing techniques. Furthermore, such probes physically touch the ends of the TSVs, and must be jammed against the surface to insure good electrical continuity. This protocol may in fact leave what was a perfectly good interposer scratched and marred by the time the test is finished, while not revealing this in the data gathered by the probe while it was in contact.

The pitch of connections on an interposer or die is also smaller than conventional devices being either probed or contacted. Even at the current level of technology, mechanical contact by probes or contacts small enough for the next generation of TSVs, flip chip bumpers, or interposers is not readily available to accomplish such an electrical test.

In addition, many interposers have electrical connection between the top side and the bottom side of the interposer. Contact with probes would have to be to both sides of the interposer. This further increases the difficulty of manufacturing an electrical test mechanism for silicon interposers.

In IC manufacturing, inspection to confirm correct, defect-free manufacturing is routinely used to examine wafers and PCBs before proceeding to the next manufacturing step. Integrated circuits (ICs) are inspected at many steps in the process, from bare wafer inspection to inspecting printed circuit boards (PCBs) before and after attaching ICs. Different types of microscopes are used at different inspection points: electron and optical microscopes are often used for inspecting the ICs during the manufacturing process, and x-ray microscopes can be used for inspecting PCBs.

The inspection techniques using optical photons or electrons to inspect silicon wafers cannot be used to inspect 3D and 2.5D IC packages because they do not penetrate through the ICs or interposers sufficiently to provide an internal view of the packaged ICs. They are also not capable of performing inspection or metrology for partially packaged components, a critical requirement for process control. X-rays, however, can penetrate through many layers of packaging to provide an internal view of the assembled device.

The initial discovery of x-rays by Röntgen in 1895 [W. C. Röntgen, "Eine Neue Art von Strahlen (Würzburg Verlag, 1895); "On a New Kind of Rays," Nature, Vol. 53, pp. 274-276 (Jan. 23, 1896)] was in the form of shadowgraphs, in which the contrast of x-ray transmission for biological samples (e.g. bones vs. tissue) allowed internal structures to be revealed without damaging the samples themselves. However, because of their short wavelength (10 to 0.01 nm, corresponding to energies in the range of 100-100,000 eV), and the absence of materials for which the refractive index for x-rays differs significantly from 1, there are no easy equivalents to refractive or reflective optical elements so commonly used in optical system design. So, even now, the most common use of x-rays is still as a simple shadowgraph, observing the structure of bones and teeth in the offices of doctors and dentists.

Early x-ray "microscopy," developed more than 50 years after the initial discovery of x-rays, simply consisted of elaborate shadowgraph apparatus, in which the diverging x-rays cast a shadow larger than the object [S. P. Newberry and S. E. Summers, U.S. Pat. No. 2,814,729]. With the advent of computer data collection, it became possible to gather more information from the specimen, changing the relative positions and illumination angles of the x-ray source and specimen in a systematic way. Using multiple transmission measurements taken at multiple angles around the specimen, images can be synthesized by computer that represent a 2-dimensional or 3-dimensional model of the specimen [G. N. Hounsfield, U.S. Pat. No. 3,778,614]. The "slices" of interior bodies so revealed are amazing to look at, revealing a great deal about the internal structures without invasive surgery. However, as far as the physics of the x-ray interaction with the specimen, these tomographic reconstructions represent nothing more than an elaborate map of x-ray absorption—a sophisticated shadowgraph.

Over time, other imaging tools for x-ray optical systems were invented. An apparatus using grazing incidence reflection from surfaces provided cone reflectors [C. G. Wang, U.S. Pat. No. 4,317,036] and capillary collimators [F. Kumasaka et al., U.S. Pat. No. 5,276,724] to allow a diverging x-ray beam to be manipulated into a collimated beam or to concentrate x-rays onto a specimen.

Systems using an x-ray microscope for the inspection of integrated circuits have been disclosed by the Xradia Corporation [W. Yun and Y. Wang, U.S. Pat. No. 7,119,953; Y. Wang et al., U.S. Pat. No. 7,394,890; M. Bajura et al., U.S. Pat. No. 8,139,846; <http://www.xradia.com/>]. FIG. 1 illustrates a prior art x-ray microscope system as disclosed on Drawing Sheet 2 of U.S. Pat. No. 7,119,953. In such a system, x-rays from a source 010 are collected by a condenser 012, which relays x-rays from the source 010 to a test object 020 to be examined. This condenser 012 is described in some embodiments as a capillary condenser with a suitably configured reflecting surface, while in others as a zone plate. The converging beam from the condenser 012 irradiates the test object 020 to be examined, and the radiation emerging from the test object 020 to be examined is scattered and diffracted out of the path of the direct radiation beam. An x-ray objective 041 is therefore used to form an image of the object, collecting the scattered x-rays. This objective 041 is described as being possibly a zone plate lens, a Wolter optic, or a Fresnel optic. In some embodiments, an additional phase plate 045, often in the form of a ring around the center axis of the system, is included to enhance contrast. Both the phase plate 045 and the objective 041 are described as being attached to a "high-transmissive substrate" 048 to form a composite optic 040. The focused radiation 051 forms an image of the test object 020 on a detector 050, which is described as possibly comprising in some embodiments a charge-coupled device (CCD), and in some embodiments comprising a scintillator, and in others being a film-based detector.

X-ray systems with Fresnel zone plate (FZP) optics such as this prior art Xradia system can be effective for the non-destructive examination of integrated circuits, but the limitations of the zone plate optics [J. Kirz and D. Attwood, "Zone Plates", Sec. 4.4 of the "X-ray Data Booklet" <http://xdb.lbl.gov/Section4/Sec_4-4.html>] reduce the wavelength range over which x-rays can be effectively collected, thereby decreasing the collection efficiency and increasing the time to collect data for a complete IC. The system is therefore very slow and inefficient for collecting large volumes of data on multiple layers of an IC.

X-ray systems using point projection microscopy (PPM) provide another way to form images of ICs, PCBs, or other packaging structures such as interposers. These systems form direct shadows of objects using x-rays emitted from a small point source. Such a prior art x-ray inspection system is the XD7600NT manufactured by Nordson DAGE of Aylesbury, Buckinghamshire UK.

A schematic of a PPM system is illustrated in FIG. 2. In a PPM system, a "point" source 10 emits x-rays 11 at a wide range of angles. The object 20 to be examined comprising detailed structures 21 is placed some distance away, so that it casts an enlarged shadow 30 comprising features 31 corresponding to the structures 21 on a detection screen 50 some distance behind the object.

The advantage to such a system is its simplicity—it is a simple shadow projection, and the magnification can be increased by simply placing the detector farther away. By not using inefficient zone plates, higher intensity and therefore faster image collection times are achieved.

For an object of infinite thinness and with no internal structure, this may be adequate. Unfortunately, ICs and packaging materials are not infinitely thin; they have complex 3D structures, and the wide angular range of the shadow projection system means that identical features illuminated at an angle cast very different shadows from those same features illuminated head on. This parallax error, illustrated in FIG. 2, must be taken into account in the image analysis of any shadow projection system, and prevents its easy use in an inspection system, since pixel-by-pixel comparison is impossible for images taken with different illumination angles.

Resolution is also an issue with PPM systems. Although x-ray wavelengths can be chosen to be short enough that significant diffraction does not occur, blurring is still a significant problem. The "point" source is actually the spot where an electron beam collides with an anode, and a typical x-ray source spot is at least 1 micron in diameter. The resolution of the shadow is therefore limited by the size of the original source spot, and at some distance, the shadows from an extended source will blur.

This blurring is illustrated in FIG. 3. For an object 20 with an opaque feature 21 of width A, a "point" source 10 of size S a distance $L_1$ away from the object 20 casts a shadow 31 of width $A_1$ corresponding to the opaque feature 21. At the edge of the shadow 31, the extended source 10 also casts an extended penumbra 32 of width $A_2$. The larger the extended source 10, the larger the penumbra 32, and the poorer the image contrast and resolution. [Note: a penumbra will appear on all sides of the shadow; only one is shown for illustrative purposes. It should also be noted that the penumbra for a PPM system will not be symmetric for off-axis features due to the parallax effects illustrated in FIG. 2.]

Throughput is therefore also an issue with PPM systems. To achieve the necessary resolution, all the x-rays must be emitted from as small a point as possible. Because x-rays are usually generated by colliding a beam of electrons into the surface of a metal, and there are therefore limits on the brightness that can be achieved from a single spot. Attempts to increase the current too high will not increase the brightness from the point source, but instead may simply melt the a hole in the anode. Attempts to increase the x-ray flux by extending the area of the source spot reduce the system resolution further. The x-ray target must generally be a thin foil, to limit the size of the x-ray spot due to electron scattering in the target. As a rule of thumb, approximately 1 watt of electron-beam energy can be deposited into a 1 micron spot on this type of x-ray target. Better resolution can only be obtained by reducing the size of the electron beam generating the x-rays, which in turn requires the beam current to be reduced to avoid thermal damage to the thin target. No existing x-ray source with spot size of 1 micron has been able to reliably operate at over 10 watts of power.

Therefore, existing x-ray systems lack sufficient resolution and imaging speed to meet the needs for high-resolution, high-throughput IC and electronic packaging inspection. Therefore, a new approach is needed to combine the penetrating power of x-rays with high-power, high-resolution, telecentric imaging techniques to provide measurement and inspection capabilities for the next generation of 3D and 2.5D integrated circuit packages, such as silicon interposers with TSVs.

BRIEF SUMMARY OF THE INVENTION

The inventions disclosed herewith comprise an x-ray system and various methods using an x-ray system. The x-ray system uses proximity imaging with a high-resolution scintillator coupled to a camera. The object to be examined is mounted in close proximity to a thin scintillator that converts x-rays into visible light. When collimated x-rays are directed at the object, a detailed high-resolution close proximity x-ray shadow image is created on the scintillator. The thin scintillator converts this x-ray shadow image into a high-resolution visible light image, and a high-magnification optical microscope creates a magnified optical image of the scintillator on a 2D optical sensor, such as a charge-coupled device (CCD) or complementary metal-oxide-semiconductor (CMOS) detector.

One advantage of the x-ray system architecture disclosed herewith is an increase in the x-ray flux. The system architecture can be implemented using embodiments that allow the full spectrum of x-rays, or a substantial portion thereof (e.g. greater than 1 percent of the energy spread of the beam) to be used for image formation, and that further allow the ratio of the x-ray source spot size to the resolution of the imaging system to be greater than 1 while simultaneously achieving a high contrast image resolution smaller than 10 microns (and in some cases, achieving sub-micron resolution).

The detector is coupled to electronics that convert the image to electronic signals. The resulting electronic representation of the 2D image of the object is stored in computer memory by the electronics.

This electronic image from the x-ray system can then be used for metrology, in which the contents and structure of the image are analyzed to determine information about the physical dimensions of the object. Measurements can also be made within the image or between features in multiple aligned images to detect variation in the materials and manufacturing processes used.

Multiple images of the same object made using different angles of incidence can also be used to determine 3-dimensional structures within the object. Because the x-rays can penetrate multiple layers of the structure, the structures can be determined without disassembling the object.

This electronic image from the x-ray system can also be used for inspection, in which the dimensions of the object determined from the image are compared with a set of rules, or in which the image of the object is compared with other images used as a reference to determine if there is a defective structure within the image. Defect detection and location identification can occur manually, or by comparison with other areas within the object, or by comparison with stored information such as an image of a similar device known to be correctly manufactured.

The use of images and measurements obtained from the x-ray system during the development and manufacture of components, such as those utilizing emerging interconnect technologies such as 2.5D IC, 3D IC, fine pitch TSVs, flip chip microbumps, interposers, etc., can accelerate process development and time to market for these new technologies.

The present invention addresses the need for a rapid, real time or near real time inspection tool for fine pitch detail including TSV, flip chip and interposer applications as well as any rapid inspection of MCP devices. The present invention may be used in a failure analysis lab, or inline with the TSV or MCP packaging processing. The rapid real time or near real time advantages of the invention allow feedback during the MCP, interposer or TSV packaging, manufacture or processing and allow significant yield improvement. Other advantages allow real time alignment of interposers and TSV dice.

The electronic image or images from the x-ray system can also be used for manufacturing process quality control or failure analysis, in which defects are detected by an inspection system using the x-ray images, and the defect information is used in determining the origin of the defects.

The electronic image or images from the x-ray system can also be used for yield improvement, in which the origin of defects detected by a quality control or failure analysis system using the x-ray images is used in identifying and eliminating the cause of the defects, improving yield. This may be accomplished using the methods of statistical process control (SPC).

In the absence of suitable tools for making these kinds of images and measurements at the pitches and dimensions required by new generations of manufacturing technologies, the economic feasibility of these technologies and the potential digital products that use them will be impacted negatively through higher cost and poor yields.

BRIEF DESCRIPTION OF THE DRAWINGS

FIG. 12A illustrates one embodiment of a membrane support having a circular aperture.

FIG. 12B illustrates a cross-section view of the membrane support of FIG. 12A.

FIG. 13A illustrates one embodiment of a membrane support having finger-like structures.

FIG. 13B illustrates a cross-section view of the membrane support of FIG. 13A.

FIG. 14A illustrates one embodiment of a membrane support having finger-like structures and a thin film overcoat.

FIG. 14B illustrates a cross-section view of the membrane support of FIG. 14A.

Figure 1:
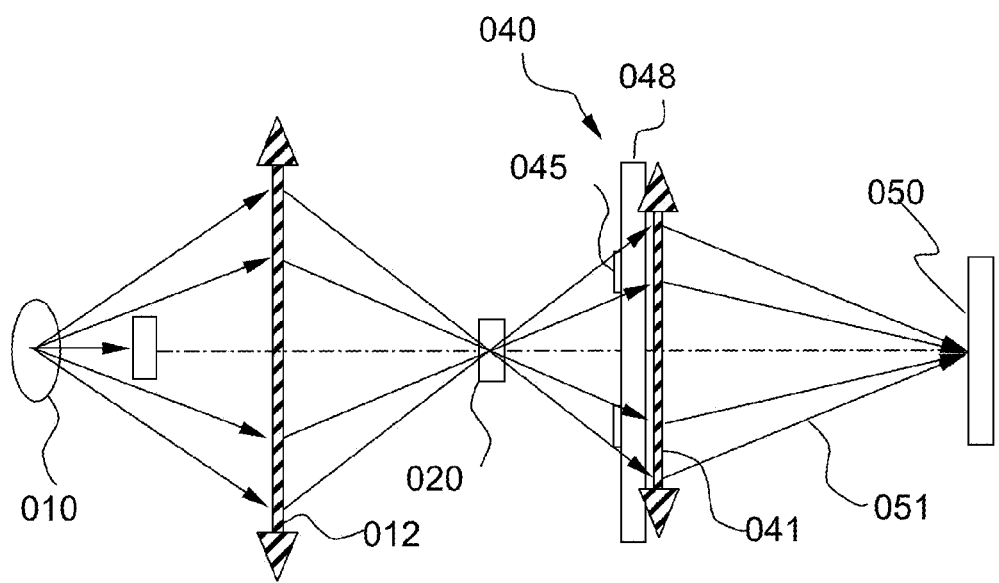
FIG. 1 illustrates a prior art x-ray microscope system from the Xradia Corporation as disclosed in U.S. Pat. No. 7,119,953.
Figure 2:
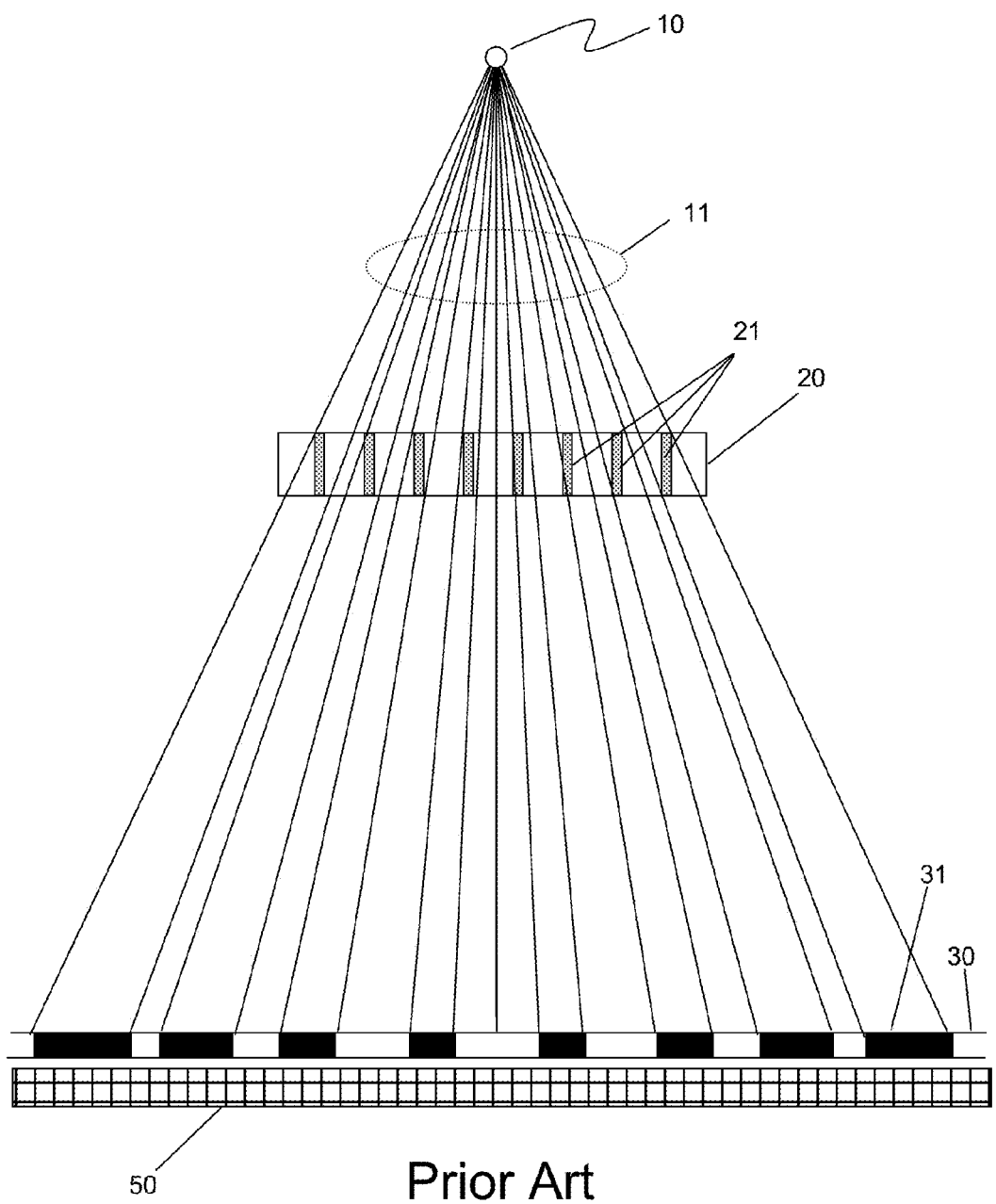
FIG. 2 illustrates a prior art system for point projection microscopy (PPM).
Figure 3:
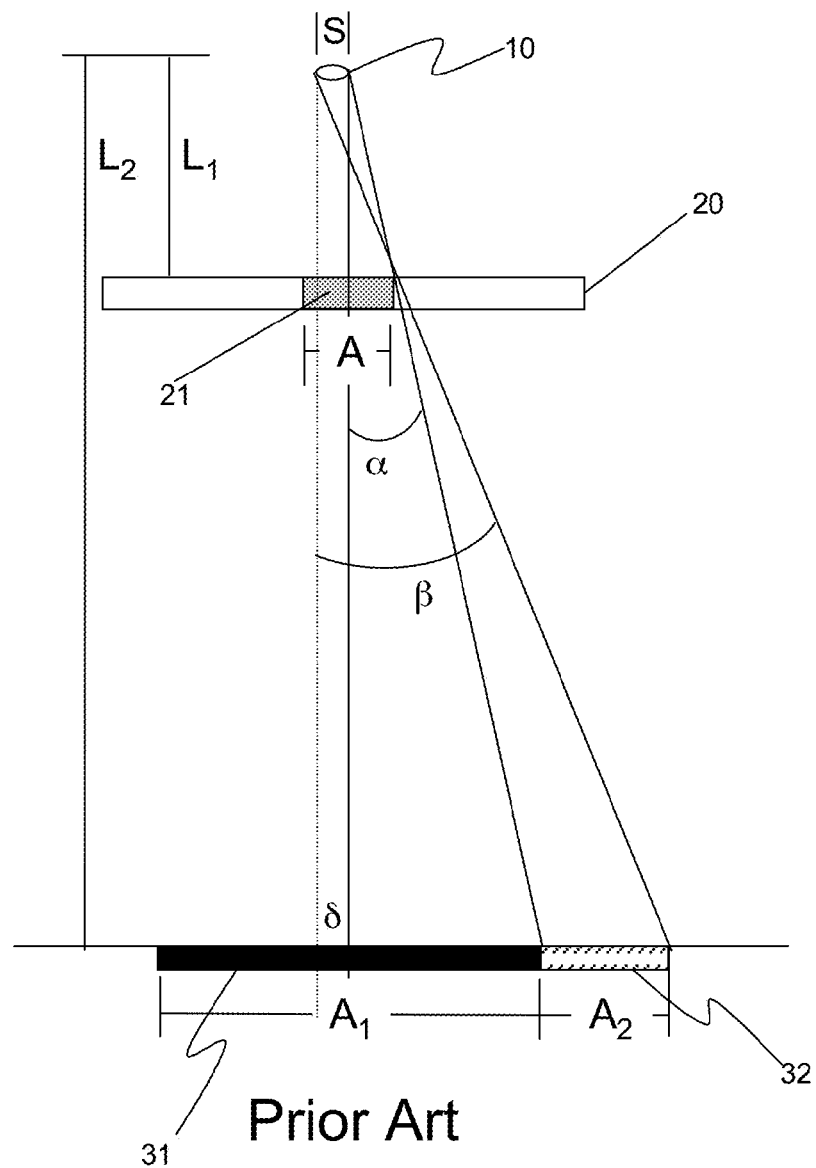
FIG. 3 illustrates resolution and blur in a prior art system for point projection microscopy (PPM).

Note: Elements shown in the drawings are meant to illustrate the functioning of the invention, and have not been drawn to scale.

DETAILED DESCRIPTIONS OF EMBODIMENTS OF THE INVENTION

Embodiments of the Invention

The system and methods disclosed in this application all comprise a system or the use of a system that illuminates an object to be examined or inspected with x-rays, converts x-rays to visible (or near-visible) photons, forms an image of the visible (or near-visible) photons, and then converts the image into an electronic form.

As such, the various embodiments of this x-ray image formation system will be presented first, followed by the various embodiments of methods and systems that utilize the x-ray imaging system.

Although many kinds of objects can be examined or inspected using the apparatus disclosed here, it is expected to be especially suitable for the examination and inspection of integrated circuit wafers and packaging assemblies. One example of these are silicon interposers, comprising silicon with multiple TSVs, but the invention can also be used for the inspection of an integrated circuit (IC) itself, a silicon interposer, a silicon dioxide interposer, a printed circuit board (PCB) with or without ICs already installed, a 3D IC package or assembly, a 2.5D IC package or assembly, a multi-chip module (MCM), a system-in-package (SIP) and other electronic microdevices or portion thereof that comprise microscopic structures. These may be examined as incoming materials, completed products, or as partially manufactured objects at any stage of their manufacture for the purpose of metrology, process control, inspection, or yield management.

Non-electronic devices with micro- or nano-structures, such as magnetic recording media, photonic structures and photonic crystals, metamaterials, etc, can also be examined and inspected using this invention. Capacitive sensors, such as fingerprint sensors, can also be examined. A particularly attractive feature of the apparatus is that it is possible to make non-destructive, high-resolution observations and measurements of features within an object that cannot otherwise be seen using electrons or optical photons, as are used in conventional metrology and inspection tools.

In general, objects suitable for use with this invention will comprise at least one flat side. Examples include: electronic circuits on semiconductor wafers, parts of wafers or selected areas on wafers; integrated circuit chips, dice, assemblies, packages, or portions thereof; micro-fluidic devices; micro-electro-mechanical systems (MEMS), including accelerometers, gyros, magnetic and capacitive sensors and the like; photonic devices, particularly those fabricated using planar waveguides; biological tissues, including stained samples; photomasks or templates for printing or fabricating any of the above mentioned devices; and solar cells, parts thereof or parts pertaining to solar cells. Other objects without flat sides may be observed and inspected as well, but the image quality may not be uniform for objects of irregular dimensions.

X-Ray Imaging System.

FIGS. 4 through 21 illustrate various embodiments of an x-ray imaging system according to the invention. Those skilled in the art will realize that these illustrations each depict only one possible embodiment, and that the figures illustrate the relative placement of elements. The actual items as depicted are not intended to be interpreted as being drawn to scale with respect to each other, nor is the vertical orientation as depicted in some figures intended to be limiting—the arrangement of elements can be oriented in any manner, including horizontally on a table, or even inverted, with a source below and the detector above.

Figure 4:
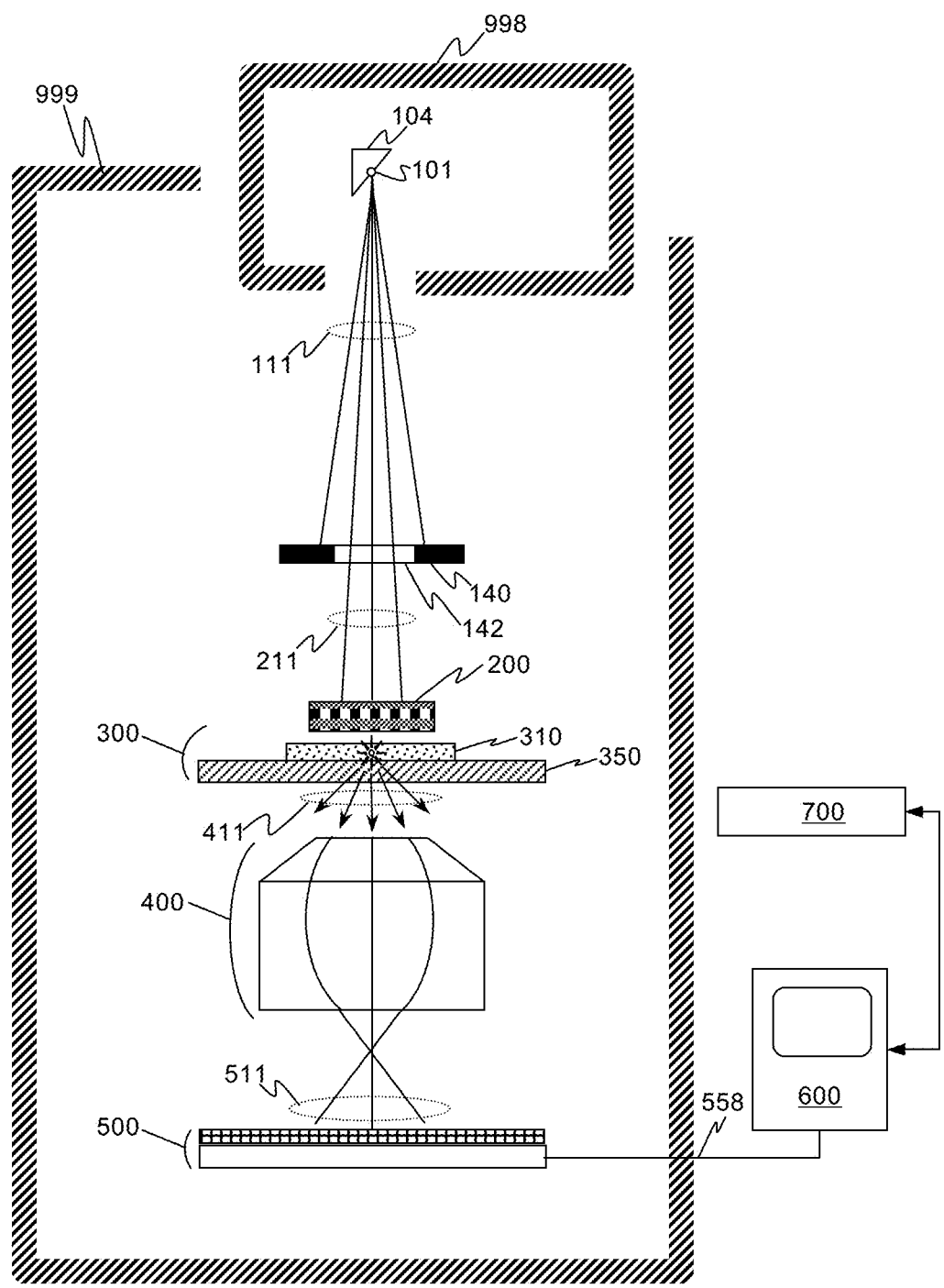
FIG. 4 illustrates an overview in cross-section of an embodiment of an x-ray imaging system according to the invention.

FIG. 4 illustrates an overview of an embodiment of an x-ray imaging system according to the invention. An x-ray emitter 101 emits x-rays 111. These x-rays are then shaped into a collimated x-ray beam 211, in some embodiments using distance from the emitter 101 and a plate 140 with an aperture 142. This collimated x-ray beam 211 then illuminates an object 200 to be examined. The x-rays that are transmitted through the object 200 illuminate a scintillator assembly 300 comprising a scintillator 310 and, in some embodiments, a support 350 for the scintillator. The scintillator 310 absorbs a portion of the x-rays and releases some of the energy so absorbed with the emission of visible photons 411.

Using an optical system 400, a magnified image 511 of the visible photons 411 emitted by the scintillator is formed on an image detector 500. The image detector 500 converts the intensity of the magnified image 511 to an electronic signal. The image detector 500 can comprise an electronic sensor, such as a charge-coupled device (CCD), or another image sensor known to those skilled in the art. The electronic signal is transmitted to a system of electronics 600 that, in some embodiments can display the image results, and in some embodiments can store the image results and/or perform image processing algorithms on the image results in conjunction with a computer system 700.

For any source emitting ionizing radiation such as x-rays, it is often wise to provide shielding 998 around the x-ray source 100, and in some situations legally required for operation. Such shielding 998 can be a simple enclosure of shaped sheets of lead metal, or a more intricate design fabricated from any of a number of x-ray absorbing materials, such as lead-doped glass or plastic, that will be known to those skilled in the art. Shielding is desirable to keep random x-rays, either directly from the emitter 101 or reflected from some other surface, from causing unwanted effects, particularly spurious signals in the various electronic components used to control the system.

Likewise, for some embodiments, additional shielding 999 around the beam path may also be desired, and in some cases be legally required for operation. Such additional shielding 999 can be a simple enclosure of shaped sheets of lead metal, or a more intricate design fabricated from any of a number of x-ray absorbing materials such as lead-doped glass or plastic, that will be known to those skilled in the art. Additional shielding 999 is desirable to keep random x-rays, either directly from the emitter 101 or reflected from some other surface, from causing unwanted effects, particularly spurious signals in the various electronic components used to control the system.

Because certain image detectors 500 such as those comprising CCD sensors can be particularly sensitive to x-ray exposure, in some embodiments a portion of the scintillator assembly 300 can also be fabricated in whole or in part using a material, such as a lead-doped glass, which absorbs x-rays while transmitting the visible photons 411 emitted by the scintillator. Other embodiments comprising a system design that places the image sensor 510 out of the x-ray beam path, as will be disclosed in more detail later in this application, may also be used if additional isolation from x-rays is desired.

Figure 5:
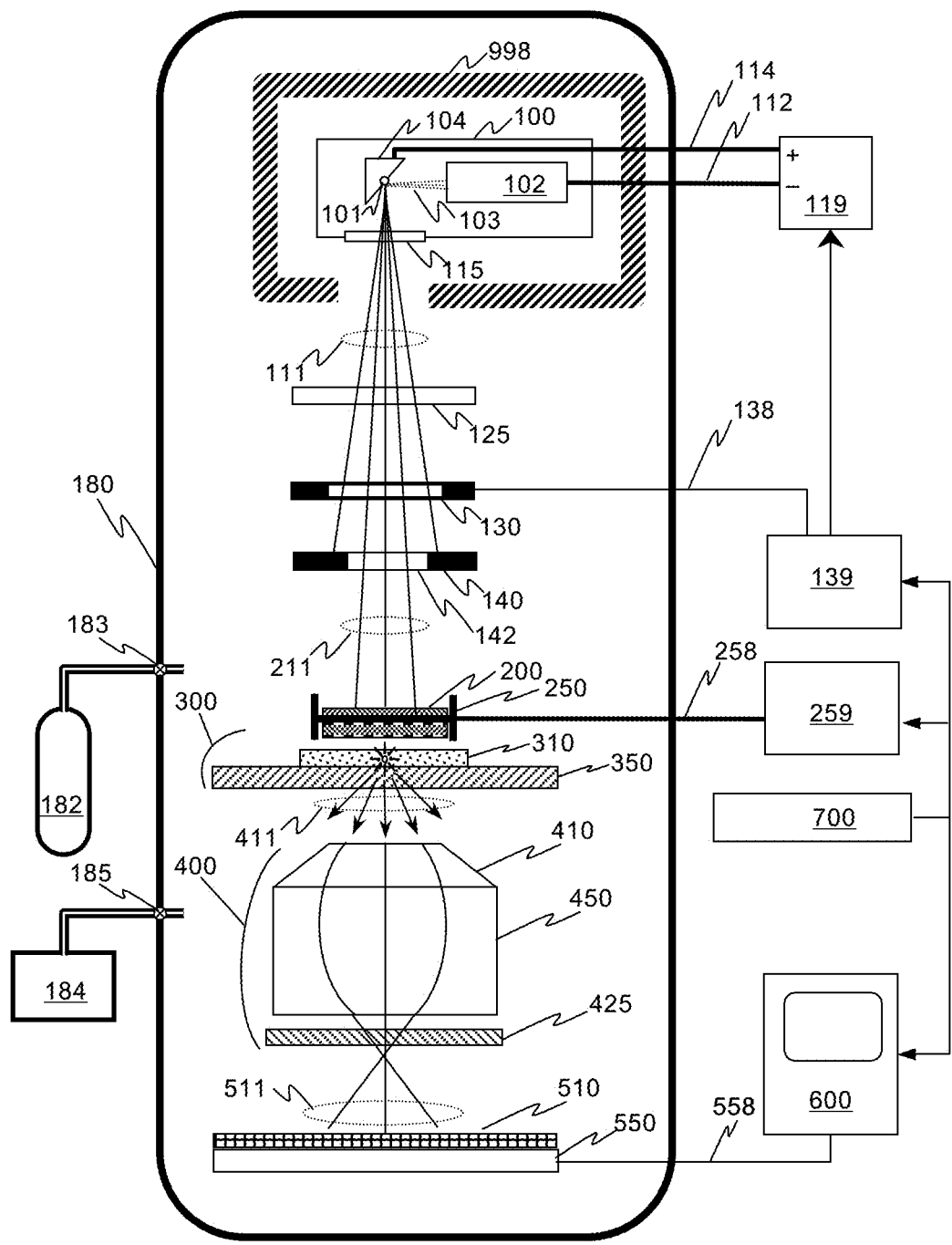
FIG. 5 illustrates the system of FIG. 4 in more detail.

FIG. 5 shows the embodiment of the x-ray system of FIG. 4 in more detail. Some elements, such as the additional shielding 999, may still be used in conjunction with this embodiment, but are not shown in FIG. 5 to allow other additional details to be shown with more clarity.

In FIG. 5, an x-ray source 100 comprises an x-ray emitter 101 that emits x-rays 111. One technique to generate x-rays is to accelerate a beam of electrons with high voltage and collide the electrons into an anode target fabricated from a designated material. In the embodiment shown, a high voltage is created by a power supply 119 and connected through positive lead 114 and negative lead 112 to create a high voltage between an electron source 102 and an anode 104, which serves as the x-ray emitter 101. Electrons 103 are then emitted from the electron source 102 to collide with the anode 104, creating x-rays 111.

A window 115 in the x-ray source 100 may be provided if maintaining a vacuum or having a fill gas of some particular composition and/or pressure in the x-ray source 100 is desired. The window 115 may comprise beryllium or some other x-ray transparent material.

The energy of the x-rays 111 emitted for such an x-ray source 100 will typically vary depending on the spot size, the accelerating voltage, the electron current, and the target materials of the emitter 101. These parameters can be adjusted and optimized independently or together to generate x-rays with particular properties. For one embodiment for an x-ray source 100 in a system designed to examine copper (Cu) micro-structures, the spot size of the emitter 101 is 1 millimeter in diameter, the accelerating voltage for electrons is 75 kV, the current is 20 mA, and the target anode is fabricated from tungsten (W). This produces x-rays of with an energy of 20-30 keV (corresponding to a wavelength range of 0.062-0.041 nanometers). If lower energy x-rays (e.g. 1.7 keV, corresponding to a wavelength of 0.730 nanometers) are desired for examining structures fabricated from aluminum (Al), an accelerating voltage of 5-10 kV can be used with a target anode comprising silicon (Si) or silicon compounds. In some embodiments, an accelerating voltage between 90 and 160 kV can be used. The choice of window material and thickness will affect the low-energy range of the x-rays due to x-ray absorption.

One example of an x-ray source is the MXR-75HP/20 1 kW x-ray source manufactured by COMET Industrial X-ray of Flamatt, Switzerland. In other embodiments, the x-ray source 100 can be a fixed or rotating anode x-ray tube, a synchrotron, a liquid metal source, or any other x-ray source known to those skilled in the art. The x-ray source may be operated in a continuous mode or a pulsed mode. Other specific x-ray sources or synchrotron sources will be known to those skilled in the art.

X-rays 111 from an emitter 101 generally emit in all directions. However, for high-resolution imaging, collimated x-rays are often preferred. Illumination of an object 200 to be examined with collimated x-rays can be achieved either by providing enough distance between the emitter 101 and the object 200 to be examined, so the angular spread of the x-ray illumination at the object 200 is small, or by using a variety of x-ray beam shaping optical elements such as zone plates or x-ray mirrors. In one embodiment, using a 1 kW x-ray source with a source spot size diameter of 1 mm and no additional beam shaping elements to illuminate an object 200 with dimensions 1 cm×1 cm, with a separation distance of 10 cm between the emitter 101 and the object 200, achieves a beam angular spread of about 1 milliradian at each point on the object 200.

In some embodiments of the invention, one or more beam adjusters 125 such as filters can be inserted between the emitter 101 and the object 200 and used to change the x-ray energy spectrum in order to provide better contrast, depending on the material composition of the object 200 under examination. For example, if the object 200 contains copper (Cu) structures (e.g. copper TSVs) embedded in a material such as silicon (Si), the x-ray spectrum can be adjusted to increase the relative portion of the x-rays with energy greater than the copper absorption k-edge at 8.9 keV. This can be achieved by increasing the electron beam voltage generating the x-rays, which increases the portion of the x-ray spectrum that is more energetic, or by using a beam adjuster 125 comprising, for example, aluminum (Al) metal to absorb lower-energy x-rays. This can lead to an adjusted x-ray beam 211 with energy that is peaked near 8.9 keV, thus increasing the contrast of the copper relative to the silicon substrate.

In some embodiments, the window 115 of the x-ray source may be selected to also function as a metallic filter, eliminating any need for a separate element such as a beam adjuster 125 to serve this function. In some embodiments, the beam adjuster 125 can also comprise beam shaping optics, such as capillary collimators, grazing incidence reflecting cones, zone plates, crystals and the like to further shape the x-ray beam angle and direction, as well as the energy spectrum. In some embodiments, an x-ray monochromator may also be inserted between the x-ray emitter 101 and the object 200 and be used to select a specific x-ray beam energy.

Aside from beam adjusters 125, the beam path between the emitter 101 and the object 200 can also include one or more shutters 130 to limit the time of x-ray exposure as well as a plate 140 with an aperture 142 to limit the physical extent of the x-ray beam. The shutter 130 can be electronically driven by a shutter controller 139 through a connector 138 such as an electrical lead, which in turn can be synchronized with the computer system 700 controlling the system, or can be operated manually by some other means. Mechanical alteration of the x-ray intensity (e.g. turning the x-rays on and off) can also be achieved in some embodiments by controlling the x-ray source power supply 119 using the controller 139.

The beam path between the window 115 of the x-ray source and the object 200 in some embodiments will be filled with ambient air at standard conditions of temperature, pressure and/or humidity, but can alternatively be filled with a designated gas composition at various temperatures and pressures, or even pumped out to low pressure or to be a vacuum. This may be of more concern if the object 200 to be examined will be heated or cooled during the time the images are collected, and an environment without oxygen, for example, may help prevent corrosion or change in the object 200.

For such an embodiment, the system may be additionally provided with a chamber 180 to contain the beam path and the appropriate portions of the x-ray source 100. This chamber 180 may be inside or outside the additional shielding 999. This chamber 180 can be further connected to one or more sources of gas 182 with a suitable means, such as a gas valve 183, for adding amounts of gas to the chamber. This chamber 180 can additionally be connected to a vacuum pump 184 with a suitable means, such as a vacuum valve 185, for removing amounts of gas from the chamber. The gas composition and conditions can be selected based on the energy of the x-rays and the environmental requirements of the object 200 under examination. For example, if low energy x-rays are to be used to provide better contrast for aluminum (Al) structures within an object, such as the interconnect layers in traditional IC, filling the beam path with helium may be preferred.

In some embodiments, the object 200 to be examined may be placed in direct contact with the scintillator 310. However, in other embodiments, the object 200 will be placed in a mount 250 and positioned in close proximity to the scintillator. This mount 250 can be a clamp, a vise, a stage (including a stage designed to hold manufactured silicon wafers), an air bearing, a membrane support, or any number of support structures that will be known or can be designed for observing objects of various sizes, shapes and compositions.

The mount 250 in some embodiments will allow the object to be moved relative the x-ray beam. Translation motion in x-y planes (with x- and y-axes defined as orthogonal axes in the plane of the scintillator) will allow observation of an object 200 larger than the size of the beam. Adjustment along the z-axis (i.e. along the direction perpendicular to the scintillator) will allow the object 200 to be moved as close as practical to the scintillator, improving resolution. Rotation in the x-y plane (around the z-axis) may also be used to align images of the object with axes of manufactured objects within the object (e.g. aligning copper wires in the object to appear horizontal or vertical in the image).

Tilting the object 200 by rotation of the mount 250 around the x- or y-axis can also allow observation of an object 200 using different angles of incidence for the x-rays. Multiple images at multiple angles can be used to allow the reconstruction of 3D structures that a single image may not provide. More information on these embodiments will be provided later in this application.

In some embodiments, the motion of the mount 250 is controlled by a controller 259 through a connector 258. The controller 259 is in turn directed either by direct input from an operator, or by electronic instructions provided by the computer system 700.

The adjusted x-ray beam 211 illuminates the object 200 to be inspected as it is held in the mount 250. Depending on the nature and construction of the object, it may comprise various internal 2D and 3D structures of various material compositions. These various materials can have varying degrees of absorption for the adjusted x-ray beam 211, producing different levels of transmission intensity. For example, for x-rays with an energy of 20 keV, absorption by 10 microns of silicon will be about 1%, while that of 10 microns of copper will be about 26%.

Figure 6:
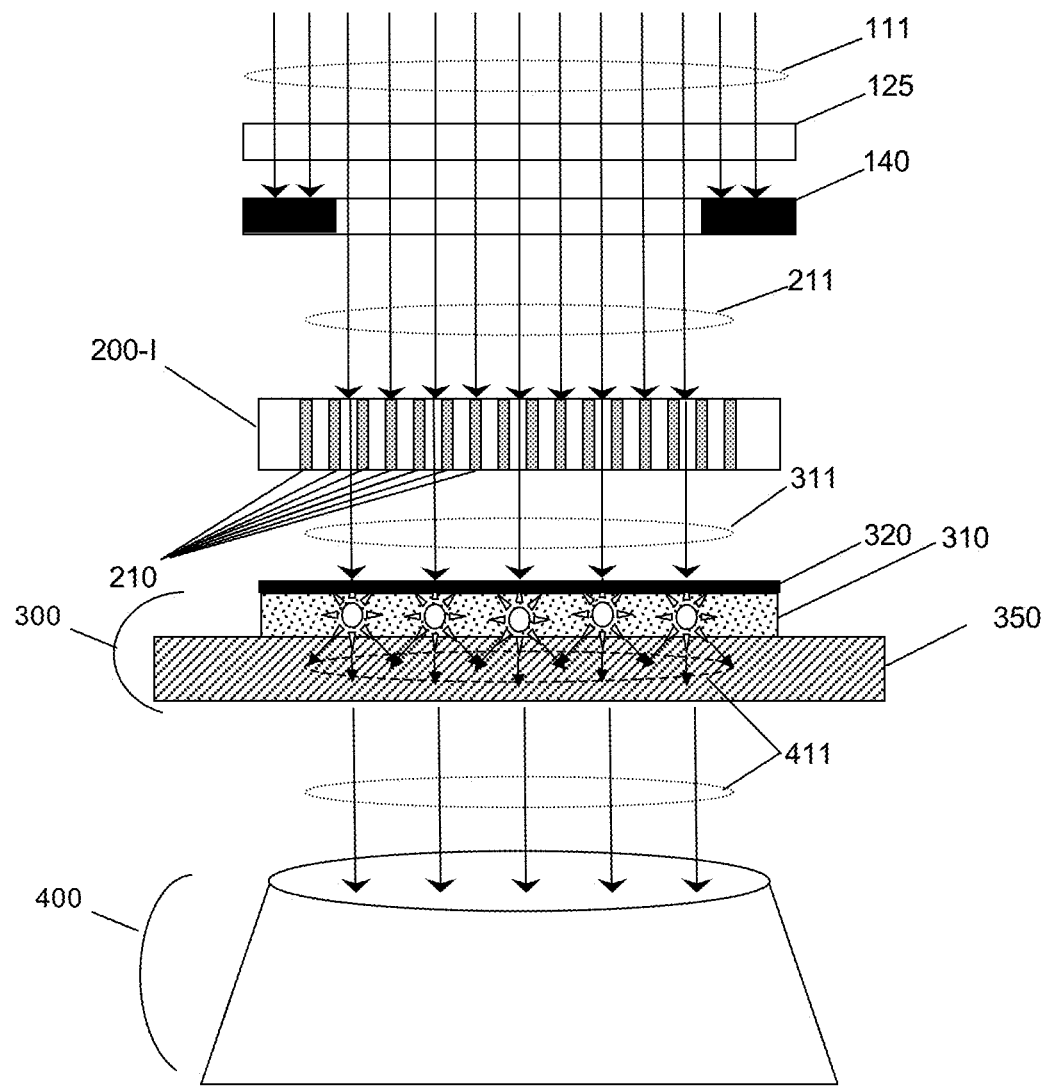
FIG. 6 illustrates in more detail the image formation elements the system of FIGS. 4 and 5.

Referring now to FIG. 6, which illustrates elements of the embodiment of FIGS. 4 and 5 in more detail, the object 200 to be inspected is illustrated as a silicon interposer 200-I, comprising a silicon wafer which can be, for example, 500 microns thick, with multiple copper TSVs 210 fabricated in the wafer and extending from one face of the silicon wafer to the other. Copper TSVs typically have a cylindrical shape, and can typically range from 1 to 150 microns in diameter and be fabricated in a wide range of pitches, for example, from a pitch range of 20 to 500 microns.

The variable transmission of x-rays through the silicon and copper of the TSVs 210 results in a pattern of intensity in the output x-rays 311 emerging from the object 200-I, shown as the absence or presence of continuing arrows in the figure. The output x-rays 311 propagate towards the scintillator assembly 300. The distance between the object 200-I and the scintillator assembly 300 can be as large as 1 mm, but if the distance between the object 200-I and the scintilltor assembly 300 is sufficiently small, typically on the order of 100 microns or smaller, there will be little scattering or spreading of the output x-rays 311 between the object and the scintillator, and the profile of the emitted visible photons 411 from the scintillator will more accurately reproduce the intensity of the output x-rays 311. In some embodiments, better pattern fidelity can be achieved if the propagation distance is minimized, and the object 200-I and the scintillator assembly 300 are in close proximity. In some embodiments, the object 200-I being examined may actually be in direct contact with the scintillator assembly 300 itself. More variations of these embodiments are disclosed later in this application.

The scintillator 310 comprises a material designed to absorb x-rays and emit visible photons 411. Although many such materials are known to those skilled in the art, one such material is lutetium aluminum garnet, doped for activation with cerium (LuAG:Ce, chemically represented by $Lu_3Al_5O_{12}$:Ce), which emits green light at 535 nm when x-rays are absorbed. LuAG:Ce is both mechanically and chemically stable, and its high density (6.76 g/cm$^3$) and hardness (8.5 Mho) allows a thinner scintillator screen (thinner than 50 microns) with higher emission to be fabricated. Scintillator materials are generally grown as single crystals, and then polished to be thin crystal wafers that are both optically smooth and relatively thin.

Other scintillator materials are: lutetium aluminum garnet doped with praseodymium (LuAG:Pr), yttrium aluminum garnet (YAG, $Y_3Al_5O_{12}$) doped with cerium or praseodymium (YAG:Ce, YAG:Pr), bismuth germanate (BGO, $Bi_4Ge_3O_{12}$), lutetium oxyorthosilicate (LSO, $Lu_2SiO_5$), gadolinium gallium garnet doped with chromium (GGG:Cr, $Gd_3Ga_5O_{12}$:Cr), and sodium iodide doped with thallium (NaI:Tl). Other scintillator materials, both fabricated from crystals and from and organic compounds embedded in plastic, will be known to those skilled in the art. Commercial scintillator screens are available from companies such as Saint Gobain Crystals of Hiram, Ohio.

Specific embodiments of the scintillator 310 can be designed to optimize either the emission brightness (which increases with scintillator thickness) or the resolution of the emission pattern (which decreases with scintillator thickness, due to increasing emission blur). Other embodiments can be co-optimized for both brightness and resolution. In some embodiments, the scintillator 310 is a crystal of LuAG:Ce 1 cm in diameter and 20 microns thick. In other embodiments, the scintillator is a crystal of LuAG:Ce 1 cm in diameter and 5 microns thick.

In some embodiments, the scintillator 310 will be controlled for thickness and surface quality, minimizing thickness variations and surface scratches. In some embodiments, the thickness variations will be controlled to be less than 10%.

In some embodiments, the scintillator assembly 300 may simply comprise a thin crystal of scintillator material. However, since such crystals can be fragile and break if an object to be examined were to be placed in contact with the crystal with too much force, a scintillator with additional mechanical supports and coatings may be preferred.

As illustrated in FIG. 6, in some embodiments the scintillator assembly 300 may have a coating 320 on the side facing the x-ray source. This coating 320 can prevent scratching of the scintillator 310 when the object 200-I being inspected is placed in contact with the scintillator assembly 300.

In some embodiments, as described in further detail below, the coating 320 can be selected to have specific mechanical and optical properties that reduce the impact of dust in the image.

In some embodiments, the scintillator 310 may also be attached to a support 350 such as a substrate. The support 350 may be a glass slide 1 mm thick made from conventional BK7 glass. This attachment of the scintillator 310 to the support 350 may be achieved by using an index-matching adhesive between the scintillator and the substrate. In some embodiments, the substrate can also provide shielding, transmitting the visible photons 411 from the scintillator 310 to the optical system 400 while also absorbing x-rays, so that unabsorbed x-rays transmitted through the scintillator 310 do not irradiate optical components, such as an objective lens, which may be damaged by exposure to x-rays. This can be achieved if the support 350 comprises a lead-doped glass. One such glass comprising 65% lead oxide by weight is RD-50 radiation shielding glass manufactured by SCHOTT North America Inc. of Elmsford, N.Y.

Returning to FIG. 5, the emitted visible photons 411 are collected by an optical system 400 that forms a magnified image 511 of the emitted visible photons 411. The magnification of the optical system 400 can be as small as 1×, but more typically will be designed to magnify the image by 10× to 100×.

In some embodiments, the optical system 400 comprises an objective lens 410. This objective lens can be similar to those commonly used for microscopy applications. In some embodiments, the objective lens will be a 10× lens, with a numerical aperture (NA) of 0.23. One such objective lens is a Nikon Plan 10× objective lens, manufactured by the Nikon Corporation of Tokyo, Japan. The objective lens 410 may also have elements manufactured using radiation-hard glass, to reduce the effects of x-ray radiation exposure on the optical components.

In some embodiments, the optical system 400 also comprises a transfer or tube lens 450 to relay the image from the objective lens 410 to the image detector 500. The transfer or tube lens 450 may also serve to additionally magnify the optical image. The transfer or tube lens 450 may also have elements manufactured using radiation-hard glass, to reduce the effects of x-ray radiation exposure to on the optical components. The transfer or tube lens 450 may also have elements manufactured using lead-doped glass, to provide additional absorption of x-rays and shielding for the optical sensors in the system.

In some embodiments, the optical system 400 can comprise additional elements 425 in the optical path to alter properties of the optical image. These additional elements 425 can comprise neutral density (ND) filters to decrease the intensity of the light reaching the detector and otherwise shape and adapt the image. Conversely, additional elements 425 can comprise an image intensifier to increase the intensity of light reaching the detector. Additional elements 425 in the optical path may also comprise elements fabricated from lead-doped glass to further shield the detector from x-rays.

Although the figures have illustrated the various optical components of the optical system 400 in a particular configuration, these can be assembled in a number of arrangements. Optical systems may or may not comprise a tube lens, may or may not comprise a filter, etc. If a filter is used, the filter may be between the transfer or tube lens 450 and the image detector 500, or may be integrated as a component within the objective lens 410 or the transfer or tube lens 450. Other arrangements and embodiments will be apparent to those skilled in the art.

An image detector 500 is used to detect the magnified image 511 of the visible photons 411. In some embodiments, this image detector 500 comprises an image sensor 510 such as a charge-coupled device (CCD) with associated electronics 550. This image sensor 510 can be placed in the image plane of the optical system 400 to convert the magnified image 511 of the visible photons 411 emitted by the scintillator 310 into electronic signals.

A CCD Camera will have a number of image sensing elements, typically arranged in a square or a rectangular array. Each element can generate a pixel of the electronic image, with the electronic signal comprising data representing the position of the pixel and the image intensity. The position of the pixel can be calibrated into x-y coordinates for the corresponding position on the object 200 being examined.

One example of a camera with a CCD image sensor is the Prosilica GT 2750 6 Megapixel CCD camera for extreme environments, manufactured by Allied Vision Technologies. The camera uses an ICX694 EXview HAD CCD sensor with 6.09 megapixels, capable of generating 25 frames/second, manufactured by Sony Corporation of Tokyo, Japan. When used with a 10× objective having an NA=0.23, a single CCD image pixel corresponds to 0.453 microns, making this an x-ray imaging system with sub-micron resolution.

Although the frame rate from this camera can be 1/25 of a second, the low light intensity emitted by the scintillator leads in some embodiments to using a longer integration time in the CCD sensor and electronics. Typical single pixel integration time in the above described embodiment is 8 seconds.

Faster image generation speed at the cost of resolution can be achieved by "binning" the pixels, collecting the signals from several pixels into one image pixel. In the above embodiment, when 8×8=64 sensor pixels are binned into one image pixel, an image can be generated in 1 second. This "binning" mode can be especially useful for real-time navigation and alignment for specific structures within an object 200 to be examined before a final, high-resolution image is collected. "Binning" can be accomplished using 2×2, 4×4, 8×8, or other combinations of sensor pixels.

Faster image collection can also be achieved by using a greater x-ray flux, which in turn increases the number of photons emitted by the scintillator 310.

In other embodiments, the image sensor 510 may be a front-illuminated CCD or a back-thinned CCD capable of detecting ultraviolet (UV) light. The CCD may be operated in interline-transfer mode, frame-transfer mode or as a time-delay and integration (TDI) sensor. The image sensor 510 may also be a CMOS sensor, or a "scientific CMOS" (sCMOS) sensor. The sensor may also be cooled to below room temperature. Other image collection sensors will be known to those skilled in the art.

The electronic signal from the image sensor 510 is then transmitted through a connector 558 to a system of electronics 600 that, in some embodiments can display the image results, and in some embodiments can store the image results and/or perform image processing algorithms on the image results in conjunction with a computer system 700. When properly calibrated, the electronic signals correspond to the transmitted x-ray intensity at corresponding locations in the object 200.

In addition to providing image signals from the detector 500 to the system of electronics 600, connector 558 may also provide information from the system of electronics 600 to the detector 500 to control settings of various elements of the detector. In some embodiments of the invention, connector 558 may extend beyond the detector 500 and connect the system of electronics 600 with the optical system 400 as well, controlling various aspects of the optical system 400 (such as focus, aperture settings etc.).

In some embodiments, the system of electronics may read in the images over an internet connection (via packets), or a serial bus (e.g. USB 2.0). In some embodiments, the system of electronics 600 may comprise a frame-grabber board and connection, such as the Orion HD high performance graphics and video capture board manufactured by Matrox Electronic Imaging of Quebec, Canada.

One or more computer systems 700 may be used to control various aspects of the x-ray system, including: properties of the x-ray source 100, including the angle of the x-ray source 100; the x-ray source power supply 119; the controller 139 directing shutters 130 or other beam conditioning or shaping equipment; and the controller 259 directing the stage 250 that manages the position and/or orientation of the object 200. In some embodiments of the invention, additional controllers can be used to control: properties of the optical system 400, including focusing or magnification; the operation of the sensor; and the collection of images from the image detector 500.

The computer system 700 can be any of a number of commercially available computers, such as an HP ENVY DV7-7212nr Notebook PC, comprising an Intel® Core i7-3630QM Processor; a 2 GB GDDR5 NVIDIA® GeForce GT 650M Graphics capability; a 750 GB 7200 RPM hard drive; a memory module comprising 8 GB DDR3 1600 MHz RAM (2 DIMM); and a 17.3-inch diagonal display (1920× 1080) display. More detail on possible variations for the computer system will be presented later in this disclosure.

Results of the X-Ray Imaging System.

Shown in FIGS. 7 and 8 are x-ray images of a test pattern having sub-micron test features fabricated in gold on silicon. The smallest line/space pitch for the innermost circle is 1 micron, comprising 500 nm lines with 500 nm spaces. For each example, one image is generated using a system constructed according to the embodiments described above, and one image is generated using commercial x-ray microscope using the prior art PPM configuration as previously described.

Figure 7A:
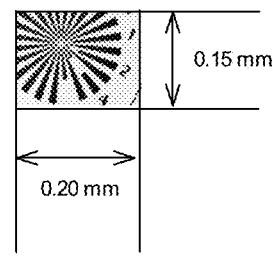
FIG. 7A presents an image of a test pattern collected using a prior art PPM x-ray system.
Figure 7B:
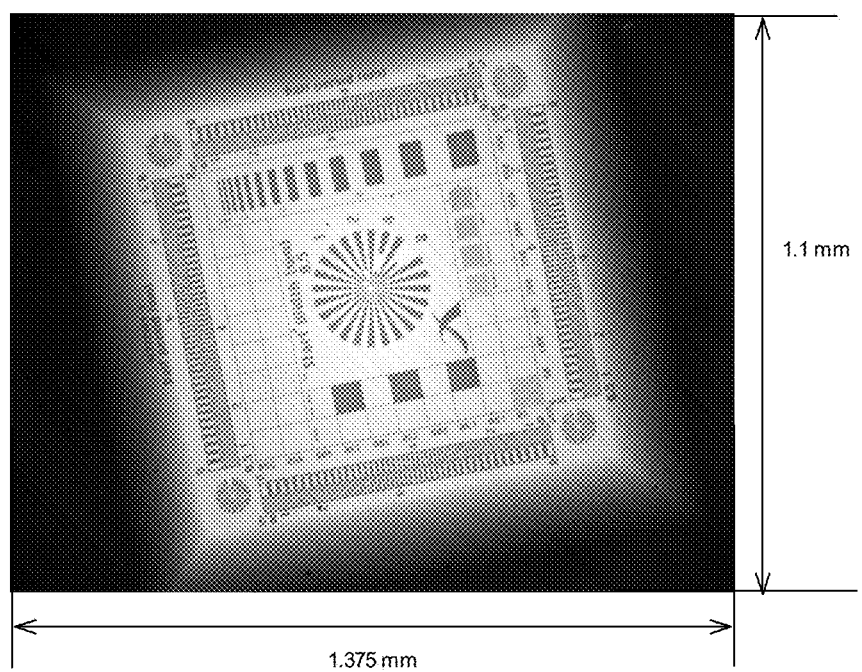
FIG. 7B presents an image of the same test pattern used in FIG. 7A, collected using an x-ray system according to the invention.

FIG. 7 illustrates an example of the larger size of the field of view for the system according to the invention. The image for the field of view for a prior art PPM system is shown in FIG. 7A, and the field of view for the system according to the invention is shown in FIG. 7B. Both images were both collected using a resolution where one pixel corresponds to 0.5 microns, and with comparable integration times.

The system according to the invention clearly demonstrates a field of view of 1.375 mm×1.1 mm, or 1.51 mm$^2$. This is more than 50 times larger than the field of view of 0.20 mm×0.15 mm, or 0.030 mm$^2$, for the PPM system with comparable image contrast and quality. A set of images covering an entire IC or chip package will therefore be collected ~50 times faster using the system according to the invention than for the prior art PPM system.

Figure 8A:
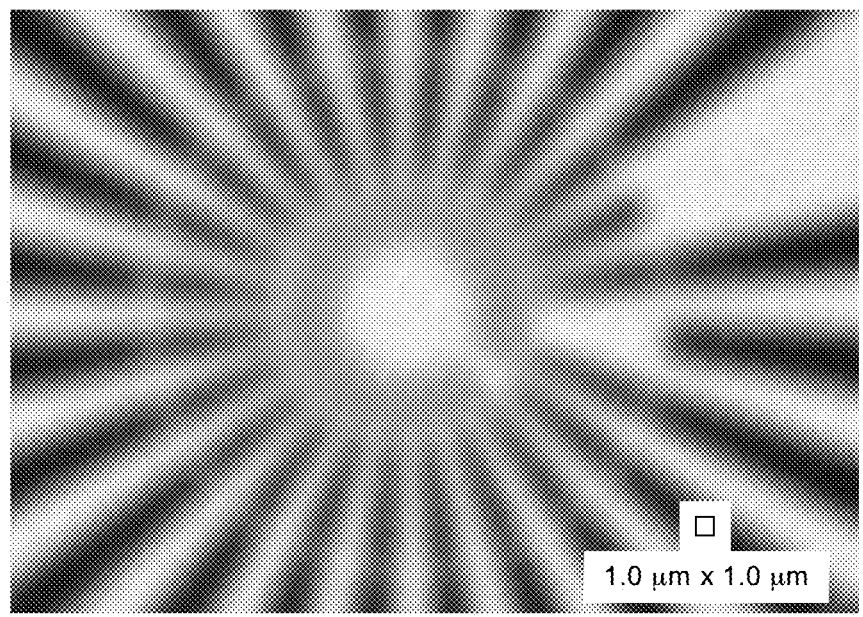
FIG. 8A presents an image of the high-resolution features of a test pattern collected using a prior art PPM x-ray system.
Figure 8B:
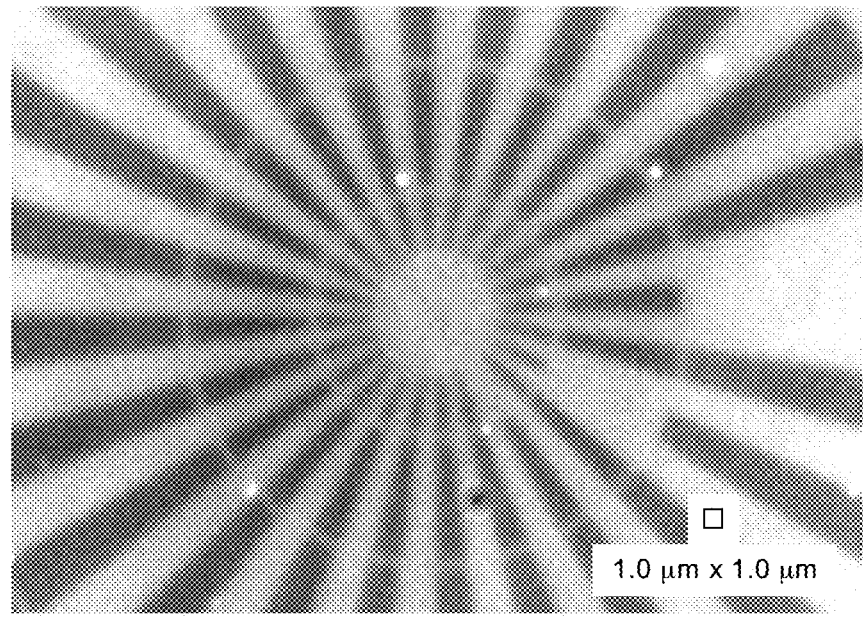
FIG. 8B presents an image of the high-resolution features of the same test pattern used in FIG. 8A, collected using an x-ray system according to the invention.

FIG. 8 illustrates an example of the higher resolution for the system according to the invention. Using the same test pattern shown in FIGS. 7A and 7B, an image showing the resolution of the prior art PPM system is shown in FIG. 8A, and an image showing the resolution of the system according to the invention is shown in FIG. 8B. Both images were collected using a resolution where one pixel corresponds to 0.1 microns, and with comparable integration times.

The system according to the invention clearly demonstrates a resolution capability for the smallest line/space features in the test pattern, which are 500 nanometers wide, while the prior art PPM system only resolves features as small as 1.5 microns (3 times larger than the system according to the invention), and only shows a blur for the 500 nanometer features.

Further Embodiments of the X-Ray Imaging System

The previous section disclosed an overview of several embodiments of the x-ray imaging system. Those skilled in the art will know some variations of the system that may offer additional advantages in certain situations. What follow are more detailed descriptions of embodiments of the invention.

X-Ray Source Variations.

Some embodiments of the invention may comprise additional variations of the x-ray source 100.

Figure 9:
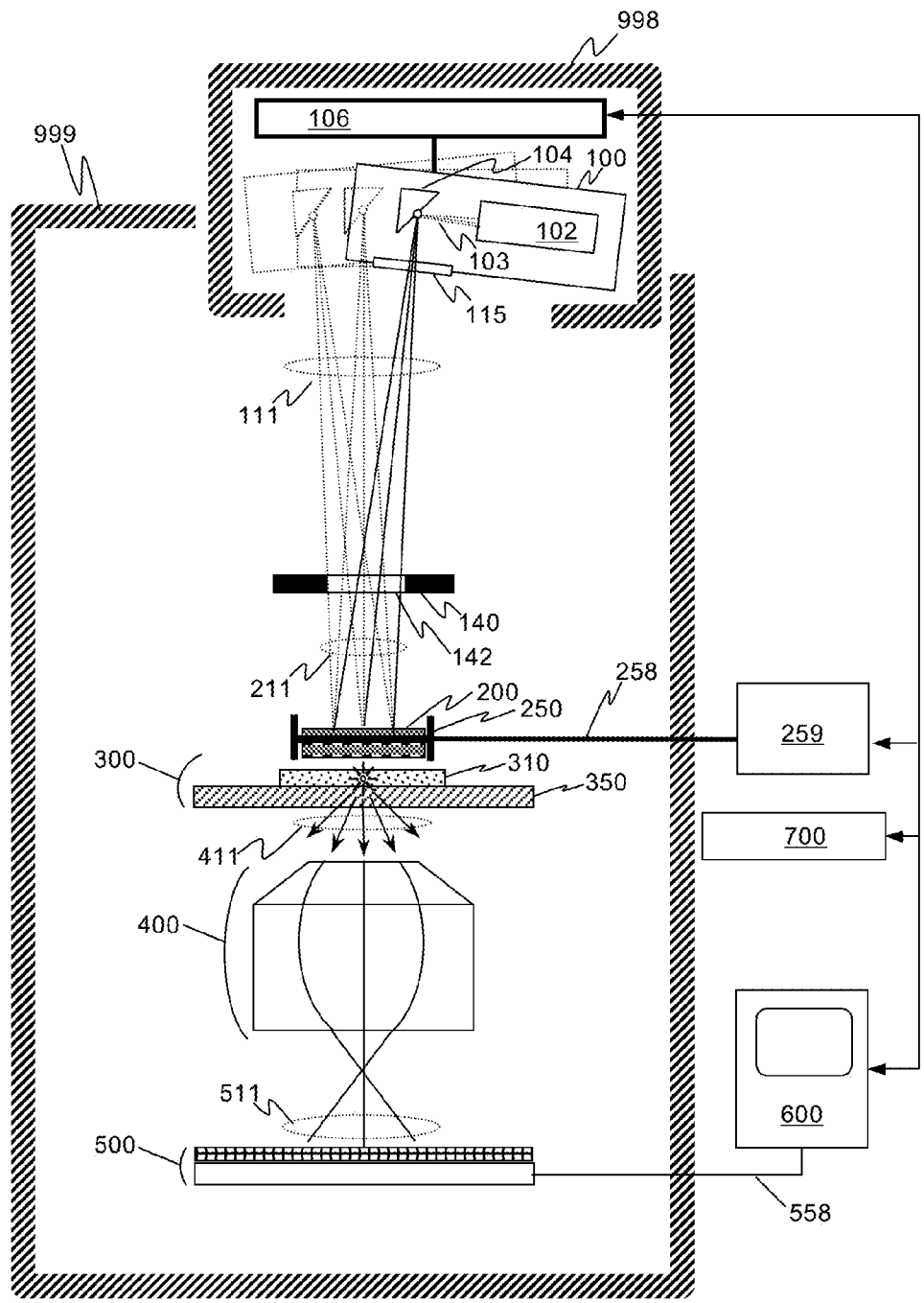
FIG. 9 illustrates an embodiment of the invention in which the x-ray source can be moved.
Figure 10:
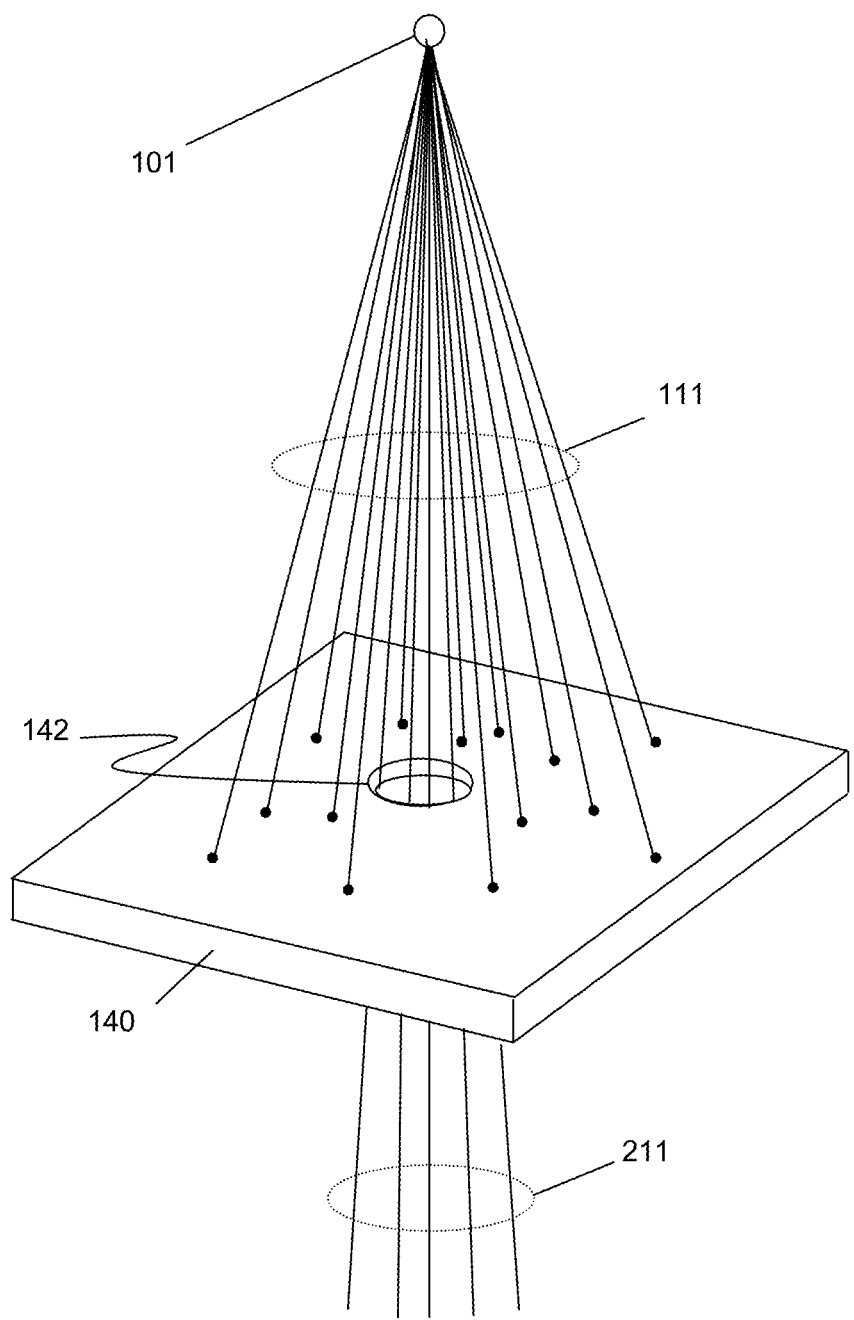
FIG. 10 illustrates an aperture being used to shape a beam as used in some embodiments of the invention.

Referring now to FIG. 9, in some embodiments, the x-ray source can comprise a mount 106 that can move the position of the x-ray source 100 relative to the object 200, thereby changing the angle of incidence of the x-ray beam on the object. The mount 106 can be designed to allow the x-ray source 100 to swing in the x-z plane, in the y-z plane, or any other combination of axes. The source can also be moved along the z-axis to move the x-ray source 100 closer to the object 200. This may have the effect of making the beam brighter, increasing signal strength, at the cost of having an x-ray beam that is less collimated, reducing resolution. This effect may be reduced or eliminated by reducing the spot size of the x-ray source.

Motion of the x-ray source 100 using the mount 106 can be controlled by the computer system 700 several ways. In some embodiments, the source mount 106 may move the x-ray source 100 to a fixed location to allow an image to be captured. In some embodiments, the mount 106 can move the x-ray source 100 continuously as images are gathered, allowing the dynamic change of x-ray intensity as transmitted through the object 200 to be recorded as a function of illumination angle. In some embodiments, the x-ray emitter 101 can be moved to at least 10 degrees off the normal incidence angle.

In some embodiments, further adjustment of the angle of incidence of the x-ray beam 211 on the object 200 can be achieved by coordinating the motion of the x-ray source 100 using the source mount 106 with the motion of the object 200 using the object mount 250. This coordination can be done manually or using the computer system 700.

In some embodiments, the shielding 998 will be designed to enclose the x-ray source 100 and the source mount 106. In other embodiments, the shielding 998 can be designed to only enclose the x-ray source, with the mount 106 designed to move the shielding 998 as it moves the x-ray source 100.

In some embodiments of the invention, multiple x-ray sources may be used to produce images with different angles of incidence. The x-ray sources may be fixed in space or moveable, and may be operated sequentially or simultaneously. They can be operated manually or controlled by one or more computer systems 700.

Beam Path Element Variations.

Some embodiments of the invention may comprise additional variations of the elements in the x-ray beam path.

X-rays 111 produced by the emitter 101 propagate in all directions from the source spot. In some embodiments, free space propagation and a suitable choice of distance to the object 200 and scintillator assembly 300 can provide collimated or near-collimated x-rays incident on the object 200. In some embodiments, such as that shown in FIG. 10, a plate 140 with an aperture 142 can be placed between the emitter 101 and the object 200 to select a portion of the x-ray beam 211 to continue propagation to the object 200.

The plate 140 can be fabricated from any number of materials that absorb x-rays. The most commonly used material is lead (Pb). Other radiation blocking materials such as steel or lead-doped glass or lead-doped polymers may be used in some embodiments. Other radiation shielding materials will be known to those skilled in the art. In some embodiments, the plate 140 may be attached to, or otherwise connected with the shielding 998 around the x-ray source 100 or the additional shielding 999 around the beam path.

In some embodiments, the aperture 142 can be circular. In some embodiments, the aperture shape can be a square, rectangle, triangle, pentagon, trapezoid, or any one of a number of geometric shapes. The aperture 142 can have a shape and size selected to be either the same or similar to the size and shape of the scintillator 310 or the object 200. The aperture 142 can be fabricated by simply punching a hole perpendicularly through the plate 140, or by the creation of more detailed geometric shape, having, for example, edges beveled with a particular angle.

Various dimensions for the thickness of the plate 140 can be used, with the thickness being specified by a desired absorption for the x-rays.

In some embodiments, beam adjusters such as an x-ray filter may also be attached to the plate 140.

In some embodiments, the shutter may also comprise a plate with aperture that allow transmission of an x-ray beam with particular shape and properties.

In some embodiments, the shutter may also comprise both a filter and a plate with aperture that allow transmission of an x-ray beam with particular energy spectrum as well as a particular shape and properties.

Mounting System Variations.

Some embodiments of the invention may comprise additional variations of the elements of the mount 250.

In some embodiments, the object 200 to be examined may be held by a mount 250 that secures the object from the sides. In some embodiments, mount 250 may comprise a clamp or a vise. In some embodiments, the object 200 to be examined may be held by a mount 250 that secures the object from the sides and/or the edges. In some embodiments, the object 200 to be examined may be held by a mount 250 that comprises an aperture so that the face of the object 200 facing the scintillator 310 is exposed. These various embodiments can allow the portion of the object 200 facing the scintillator 310 to have nothing intervening in the space between the object 200 and the scintillator assembly 300. In these various embodiments, the mount 250 securing the object 200 may be moved to place the object 200 in very close proximity or in direct contact with the scintillator assembly 300.

Figure 11:
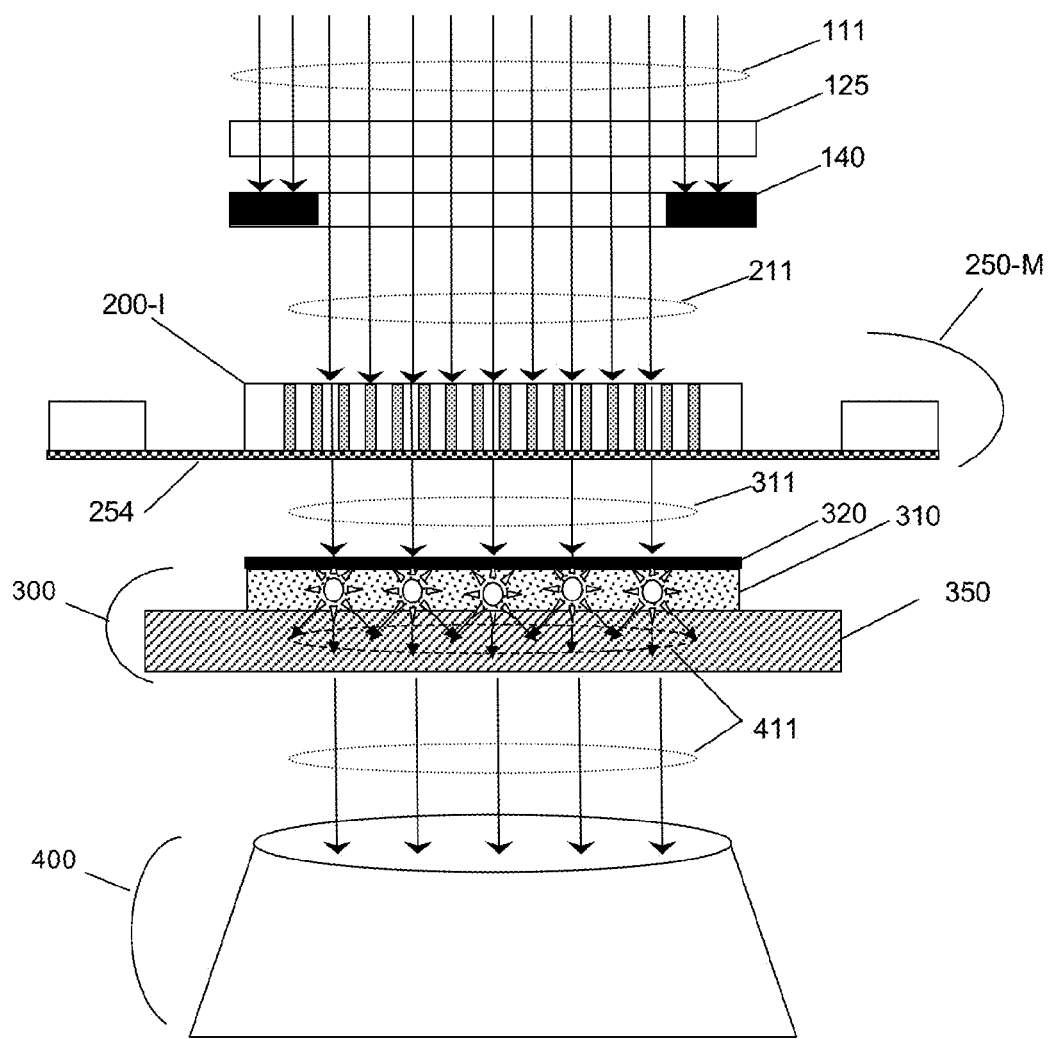
FIG. 11 illustrates an embodiment in which the support for the object being examined is provided by a membrane.

Referring now to FIG. 11 through FIG. 14, in some embodiments, such as that illustrated in FIG. 11, the mount is a structure 250-M that comprises a membrane 254 that supports the object (now shown as an interposer 200-I) to be examined. The membrane 254 with object 200-I can be moved to be in close proximity or in actual contact with the scintillator assembly 300. In some embodiments, the membrane 254 may be opaque, to prevent light from the scintillator 310 from reflecting off the object 200-I and scattering back into the optical system 400.

In some embodiments, the membrane 254 may be manufactured from a radiation resistant material such as Kapton®, a radiation resistant polyimide film with mechanical and thermal stability having high transparency for x-rays and insensitivity to radiation damage. Kapton® is a commonly used material for windows of all kinds in x-ray sources (synchrotron beam-lines and x-ray tubes) and x-ray detectors. A typical commercial Kapton® film is 25 microns thick, with thin Teflon® coatings 2.5 microns thick on each side. Kapton® is manufactured by the E. I. du Pont de Nemours and Company of Wilmington, Del.

In some embodiments, the membrane 254 may be comprise a carbon fiber film, such as Scotchprint® Wrap Film Series 1080™ vinyl film manufactured by the 3M™ Corporation of St. Paul, Minn.

In some embodiments, the membrane 254 may comprise beryllium, a rigid metal with high transparency for x-rays as well as a high thermal conductivity and a low coefficient of thermal expansion.

In some embodiments, the membrane 254 may comprise glass or fused silica. In some embodiments, the membrane 254 may comprise a crystal such as quartz, LuAG, or other crystals listed above that are used for scintillators but without the doping that causes scintillation to occur. In some embodiments, the membrane 254 may additionally comprise an aperture, such that the membrane 254 supports the object 200, but the aperture allows the face of the object 200 being examined to be directly exposed to the scintillator 310.

The mount 250-M comprising membrane 254 may also comprise support structures for the membrane 254. In some embodiments, as illustrated in FIG. 12A and FIG. 12B, these support structures 251 comprise a ring-shaped object with an aperture in the middle, allowing the membrane 254 to support the object 200 in the aperture. In some embodiments, as illustrated in FIG. 13A and FIG. 13B, these support structures 252 comprise a pair of finger-like supports for the membrane 254. Other designs and shapes for the support structures will be known to those skilled in the art.

In some embodiments, as illustrated in FIG. 14A and FIG. 14B, the object 200 to be examined will have an additional overcoat 256 to secure it in place. This overcoat 256 may also be a film made of Kapton®, carbon fiber, or other x-ray transparent materials known to those skilled in the art.

In some embodiments, motion of the mount 250-M with support structures 252, including translations in the x-y plane to change the position of the object 200, as well as vertical translations along the z-axis to move the object closer to (or even in contact with) the scintillator assembly 300, or further away from the scintillator assembly 300 (for example, for loading or unloading the object 200), is also possible. In some embodiments, rotation of the mount 250-M around various axes is achieved. In some embodiments, these various motions can be controlled by the same controller 259 as discussed above. In other embodiments, motion may be controlled by independent controllers.

Referring again to the embodiment of FIG. 11, the object 200-I moves but the scintillator 310 does not; instead, the mount 250-M with membrane 254 moves the object 200-I to allow images to be collected for different locations of the object. Another motion, perpendicular to the plane of the object 200-I, may also be actuated to cause the object 200-I and/or membrane 254 to be brought into proximity or contact with the scintillator 310, or conversely moved away from the scintillator 310 for changing objects or replacement of the membrane 254. In some embodiments, the object is attached to, or sits on, a membrane that separates the object from the scintillator. In this embodiment, the membrane may be opaque, to prevent light from the scintillator from reflecting from the object into the optical system. The membrane may be made from radiation-resistant materials, such as Kapton® or carbon fiber films. The membrane may serve as a stage to move the object over the scintillator, to permit viewing of different parts of the object.

In some embodiments of the invention, such as when the entire object 200 to be examined is relatively small and can be imaged completely on the image detector 500, the mount 250 can be a static mount that does not move relative to the scintillator assembly 300 and the optical system 400. In some embodiments, the mount 250 can be clamped or otherwise attached to the scintillator assembly 300 to prevent relative motion or vibration. In some embodiments, the mount 250 can comprise an air bearing to support the object 200 under examination, which can provide both close proximity for the object and the scintillator as well as uniform separation.

In some embodiments of the invention, such as when the object 200 to be examined is large, and cannot be completely imaged entirely with the image detector 500 in one exposure, the mount 250 for the object 200 can comprise a motion control stage, which moves the object 200 in the x-y plane. In some such embodiments, an image can be collected for one portion of the object 200 while it is static in one position, and then the object can be moved and stopped at a second position, and a second image can be collected for a second portion of the object. This process can proceed until images from multiple areas or even the entire object 200 have been collected.

In other embodiments, mount 250 can be designed so that the object 200 to be examined moves continuously as x-ray exposures are made, and the motion only stops after images have been collected for a designated portion or the entirety of the object 200. In such an embodiment, the x-ray source 100 may be operated in a pulsed mode to reduce the effect motion will have on the blur in the resulting images. The pulsing can be achieved either by varying a voltage in the power supply 119 for the x-ray source 100, or by using the shutter 130 in the x-ray beam 211 to control the exposure time. In some embodiments of the invention, the motion of the object 200 and the pulsing of the x-ray beam 211 can be synchronized, so that a stroboscopic effect is achieved. This can be especially useful if the object contains periodic arrays, and the object moves by one period (or multiple thereof) between each pulsed exposure. The strobe effect may be used to limit blurring of an image without stopping the stage completely at each location an image is desired.

In some embodiments, the mount 250 comprises a wafer stage to support an entire silicon wafer. Typical silicon wafers used in manufacturing have diameters of 6 inches, 8 inches (200 mm), 12 inches (300 mm), and 450 mm. Silicon wafer thicknesses typically vary with wafer diameter, with 200 mm wafers having a thickness of 725 microns, 300 mm wafers having a thickness of 775 microns, and 450 mm wafers having a proposed standard thickness of 925 microns. The electronic devices are typically manufactured on one side of the wafer, so for examination in the x-ray system, if the object 200 to be examined is a silicon wafer, the wafer will be inverted to allow the side with the electronic devices to be facing the scintillator 310. In some embodiments, the wafer stage will comprise a mounting system that holds the wafer by its edges, so that the x-rays are not attenuated by the wafer mount as they enter the rear of the wafer. One example of a wafer stage is the Razor™ Atmospheric Transfer Robot from Brooks Automation of Chelmsford, Mass.

In some embodiments of the invention, as was illustrated in FIG. 9, the angle of incidence of the x-rays on the object will be variable, and the system can be adjusted to take multiple images of the object to be examined at multiple angles. When a set of images at pre-determined angles are collected, the set of images can be used by a computer program to synthesize a 3D representation of the layers of the object. In some embodiments, this 3D synthesis can be achieved using the algorithms of computed laminography (CL). These algorithms can be operated on the one of more computer systems 700 controlling the system, or the images can be exported through a network to a different computer for further analysis.

Figure 15:
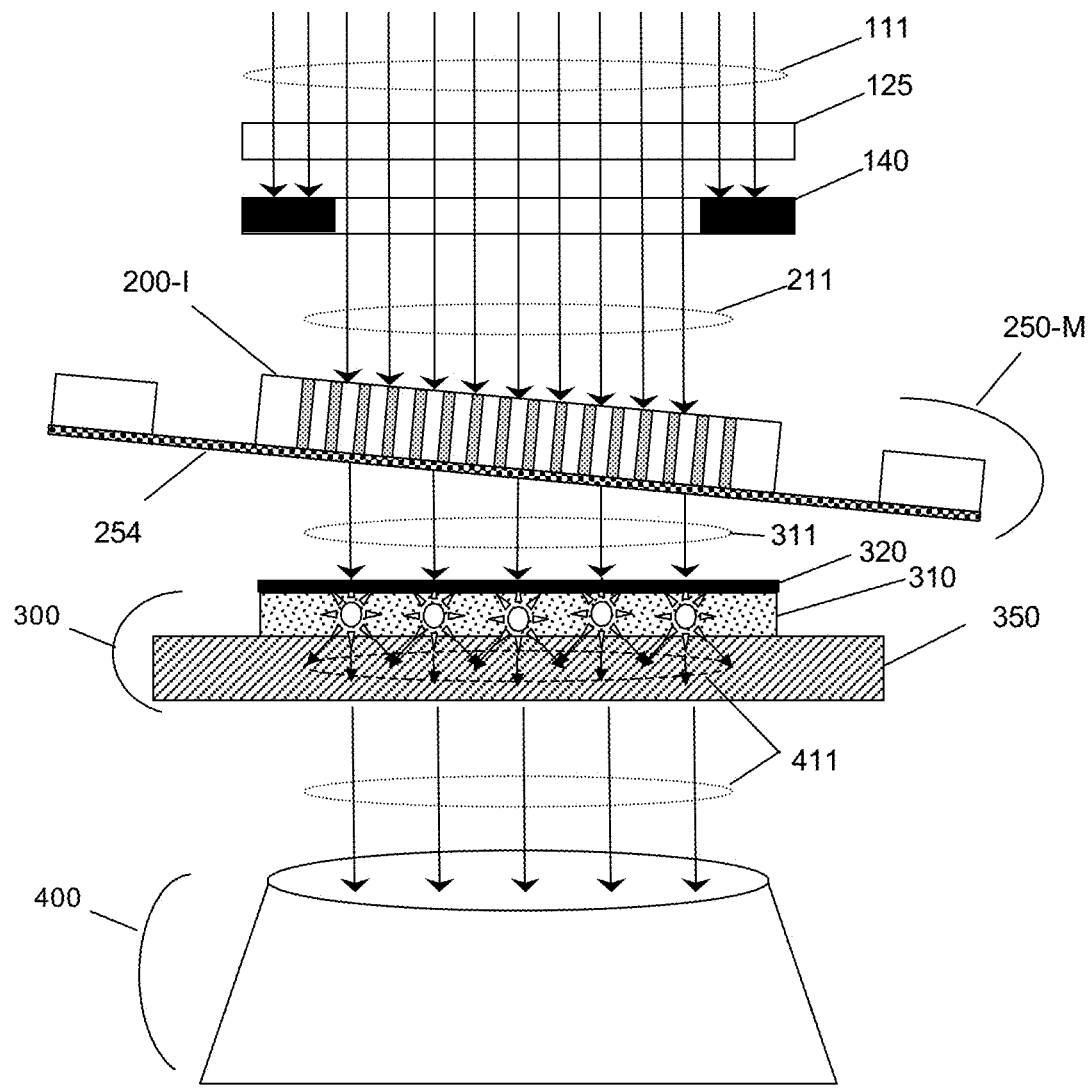
FIG. 15 illustrates an embodiment in which the object being examined and its membrane support are tilted.

Referring now to FIG. 15, the angle of incidence for the x-ray beam 211 on the object 200-I can also be adjusted by tilting or rotating the object 200-I and mount 250-M.

Figure 16:
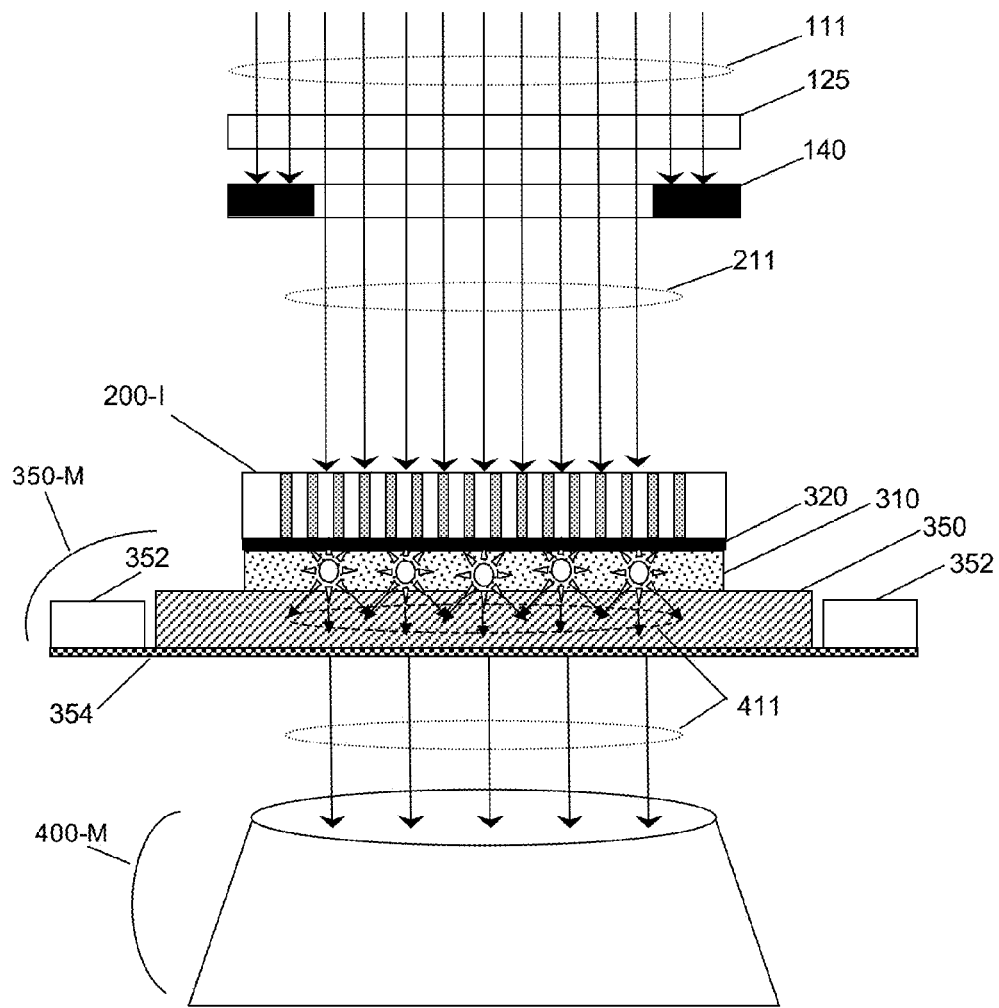
FIG. 16 illustrates an embodiment in which the object being examined and the scintillator assembly are supported by a membrane.

Referring now to FIG. 16, in other embodiments the invention, the object 200-I to be examined is placed in contact with the scintillator assembly 300. In this embodiment, the entire scintillator assembly 300 is also supported by a scintillator mount 350-M, which can also comprises a membrane 354 and finger-like support structures 352 analogous to the mount 250-M with membrane 254 and support structure 252 shown in FIGS. 11, 13 and 14. In some embodiments, the scintillator mount may also be constructed to comprise a support such as a thick substrate in place of a membrane 354 to support the object being examined. In some embodiments, the membrane 354 may be selected to have properties similar to that of the earlier described support 350, such as stiffness, rigidity, and opacity to x-rays.

For the embodiment shown in FIG. 16, the membrane 354 is now between the scintillator 310 and the optical system. In this case, the optical system must be designed to anticipate this additional optical element affecting light from the scintillator, and will therefore be a modified optical system 400-M and may not be identical to the earlier described optical system 400.

Additional embodiments of the invention may comprise a membrane 354 to support the scintillator assembly as previously described for the mount 250 for the object 200. In some embodiments, the membrane 354 may comprise Kapton®, glass or fused silica, a crystal such as quartz, LuAG, or other crystals listed above that are used for scintillators but without the doping that causes scintillation to occur. Other materials that are transparent to visible photons that can be used for membranes may be known to those skilled in the art.

In some embodiments, the mount 350 may secure the scintillator assembly 300 from the sides. In some embodiments, mount 350 may comprise a clamp or a vise. In some embodiments, the mount 350 may secure the scintillator assembly 300 from the sides and/or the edges. In some embodiments, the mount 350 that secures the scintillator assembly 300 may comprise an aperture so that the face of the scintillator assembly 300 facing the optical system 400 is exposed. These various embodiments can allow the portion of the scintillator assembly 300 facing the optical system 400 to have nothing intervening in the space between the scintillator assembly 300 and the optical system 400. In these various embodiments, the mount 350 securing the scintillator assembly 300 may be moved to place the scintillator assembly 300 in very close proximity or in direct contact with the optical system 400.

Figure 17:
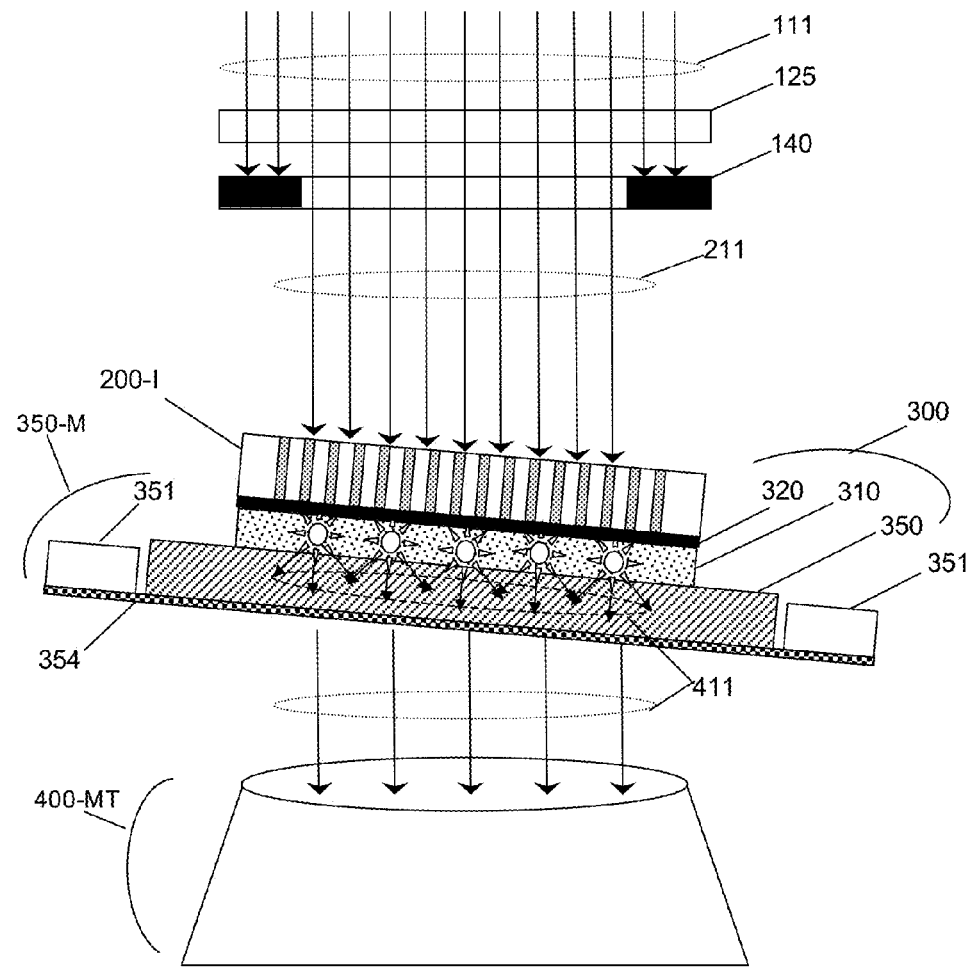
FIG. 17 illustrates an embodiment in which the object being examined, the scintillator assembly, and its membrane support are tilted.

Referring now to FIG. 17, in this embodiment, the combination of object 200-I and scintillator assembly 300 can be translated, rotated or tilted, as shown in the illustration. The object 200-I in this tilted configuration can then be rotated about the z-axis to allow images at multiple angles to be collected.

In a configuration such as that shown in FIG. 17, the optical system 400-MT may be further modified from the optical system 400 used for imaging where the scintillator is perpendicular to the optical axis of the optical system 400 (normal incidence imaging), as was shown in FIGS. 6, 11 and 16. The optical system 400-MT may also be further modified from the optical system 400-M that was used for imaging an object where the scintillator is supported by a membrane 354, as was shown in FIG. 17. The optical system 400-MT will need to collect an image of the scintillator 310 while it is supported by a membrane 354 and is tilted off axis. In some embodiments, as will be known to those skilled in the art, this can be achieved by using a design for the optical system 400-MT that produces an image with enhanced depth of focus.

Figure 18:
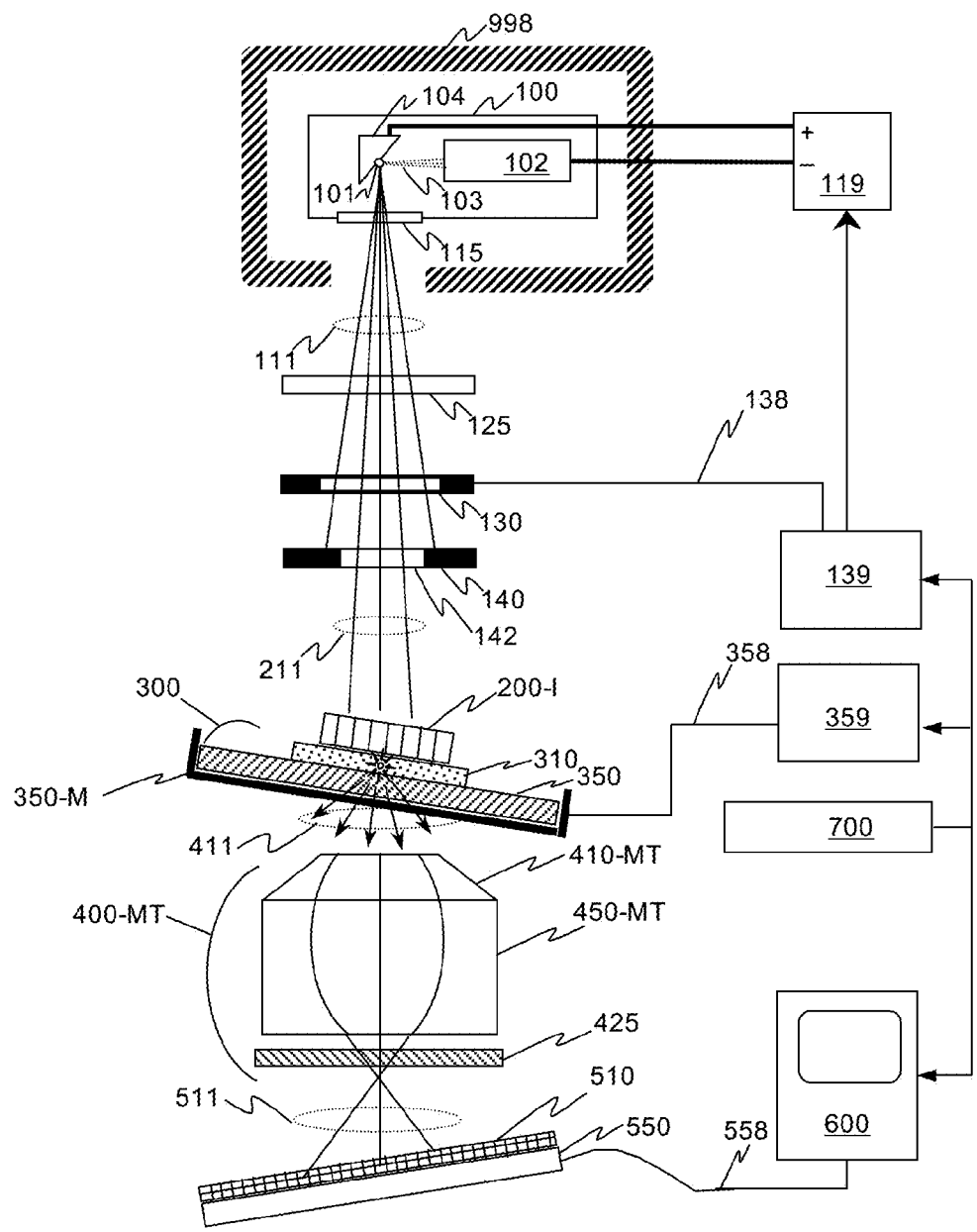
FIG. 18 illustrates an overview in cross-section of an embodiment of an x-ray imaging system according to the invention in which the object being examined and the detector for the image are both tilted.

Referring to FIG. 18, in some embodiments, this can be achieved by using a design for the optical system 400-MT in which the image plane of the optical system 400-MT may be tilted at an angle to the x-y plane. In some embodiments, the image sensor 510 can be placed at this tilted image plane. As was the case for moving the mount 250-M, connector 358 and controller 359, analogous to connector 258 and controller 259, can be used to move the object 200-I and scintilaltor assembly 300 combination. The motions may be the analogous translations, rotations, and tilts as discussed above. If the mount 350-M is rotated to collect images at different angles of incidence, the image sensor 510 will need to be correspondingly rotated to ensure the image remains in focus.

Figure 19:
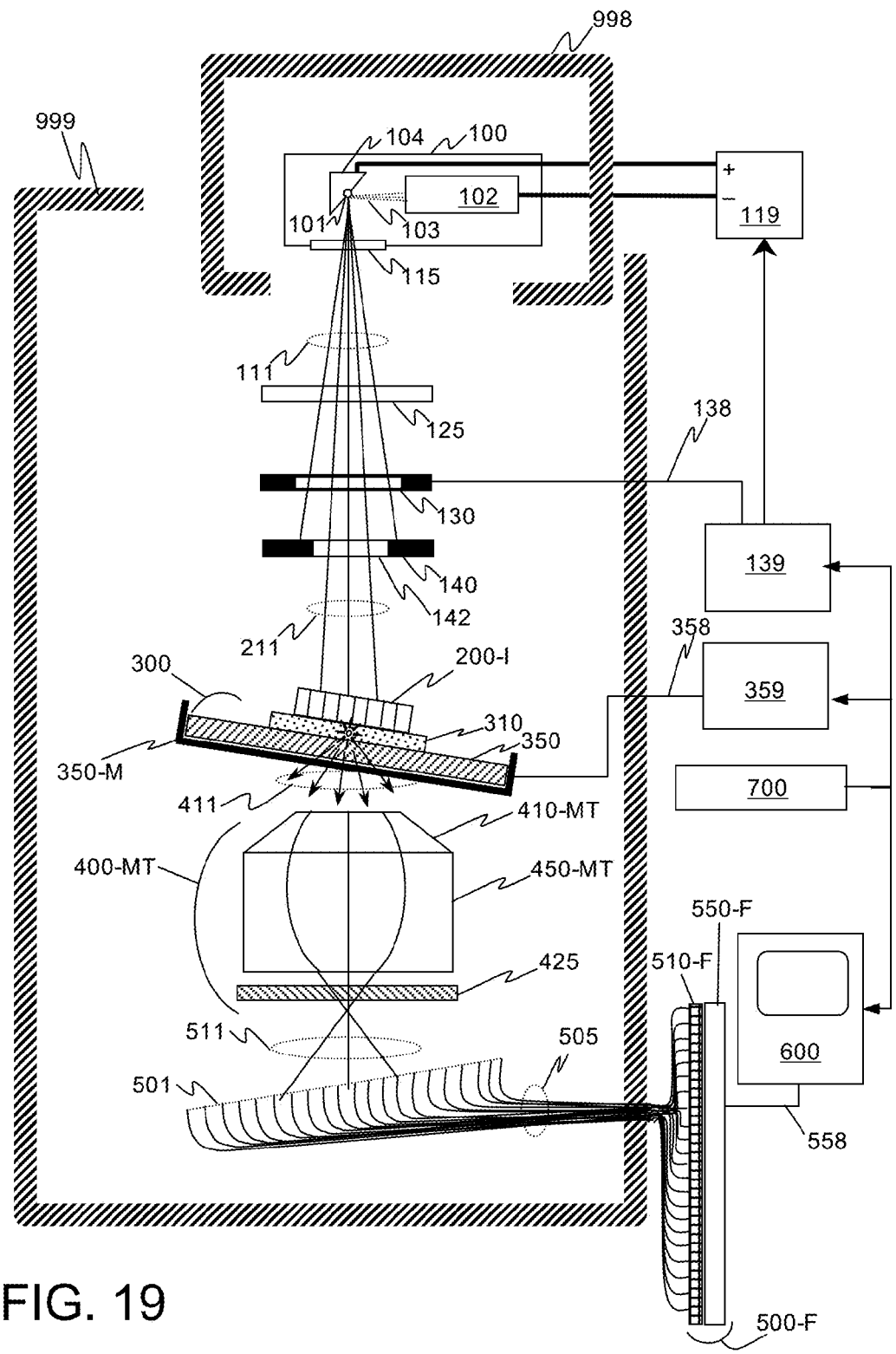
FIG. 19 illustrates an overview in cross-section of an embodiment of an x-ray imaging system according to the invention a fiber-optic bundle is used to convey the image to the detector.

Referring now to FIG. 19, in other embodiments, one set of ends for a fiber optic bundle 505 can be placed at the image plane 501 of the optical system 400-MT, and the other ends of the fiber bundle 505 placed in close proximity to the modified image sensor 510-F (which may be modified from the image detector 500 of other embodiments to accommodate coupling to the fiber bundle) of the detector 500-F. In this embodiment, if the mount 350-M is rotated to collect images at different angles of incidence, the ends of the fiber optic bundle 505 may need to be correspondingly rotated to ensure the image remains in focus.

Figure 20:
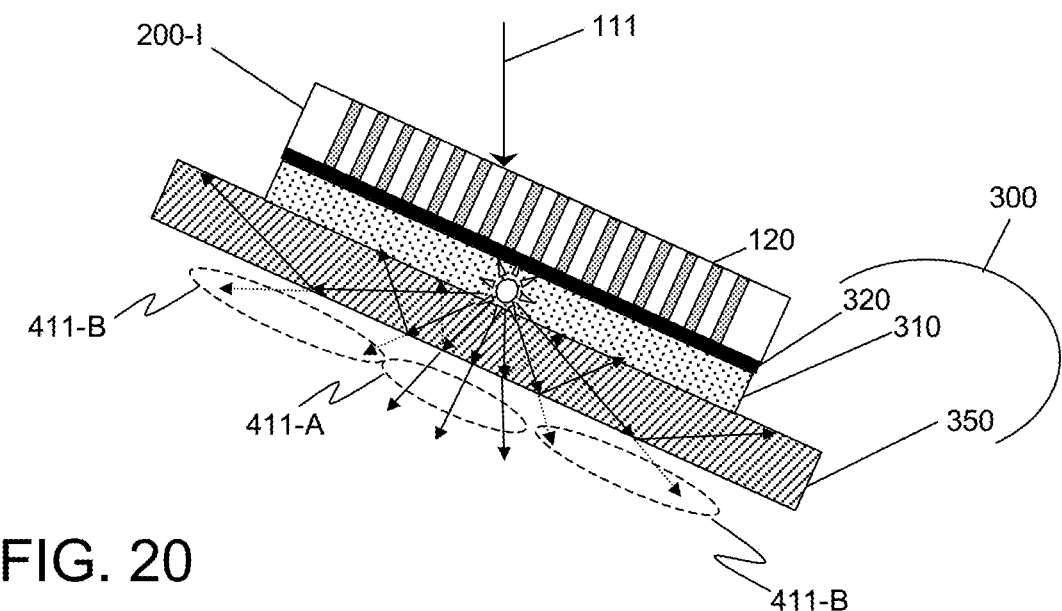
FIG. 20 illustrates the emission of light from a tilted scintillator.

Referring now to FIG. 20, the emission of photons by the scintillator 310 is typically uniform in all directions. However, if the scintillator 310 and support 350 are tilted, because the angles encountered by the emitted photons at the face of the tilted support 350 are not uniform, the light emerging from the support 350 may be attenuated more for some angles than others, distorting the image. For some tilt angles, light emitted along the optic axis of the objective lens may be internally reflected.

In FIG. 20, scintillator emission that exits the support 350 in directions near normal incidence 411-A to the plane of the support 350 will be mostly transmitted through the support-air interface. However, scintillator emission that exits the support 350 in directions far from normal incidence 411-B to the plane of the support 350 will be much weaker, and have much more of the light reflected back into the support 350 at the support-air interface. The reflection and transmission coefficients can be calculated from the relative indices of refraction for these materials, as will be known to those skilled in the art.

Figure 21:
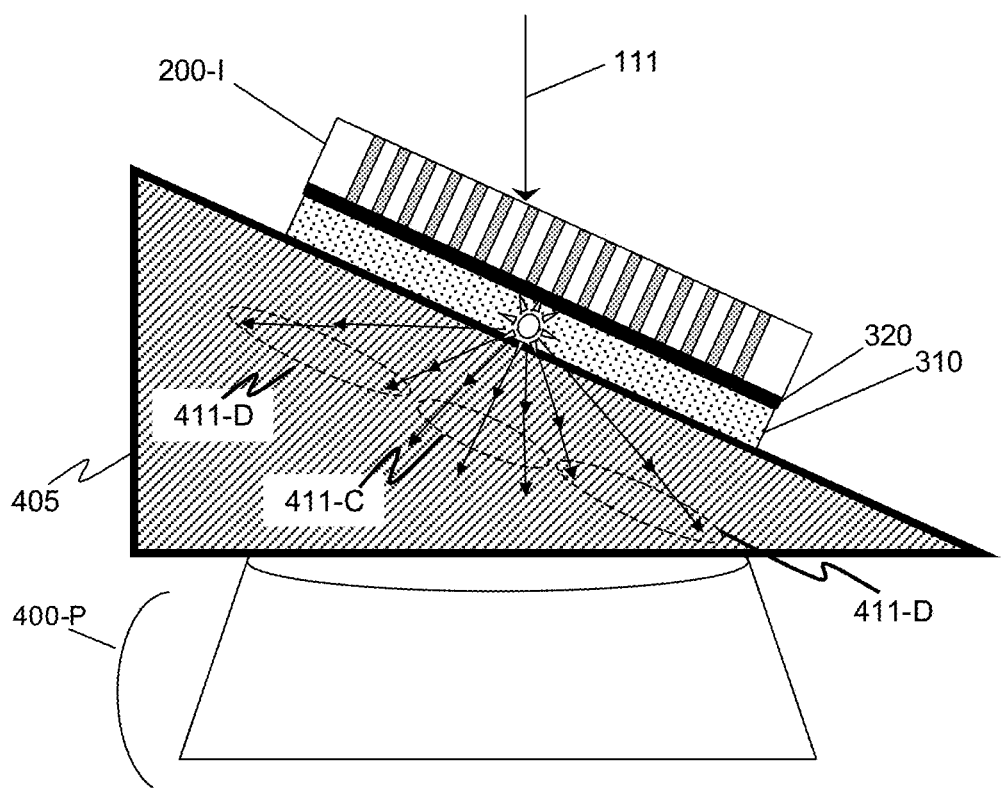
FIG. 21 illustrates an embodiment of the invention using a prism.

Referring now to FIG. 21, in some embodiments the non-uniformity of the light transmitted through the support-air interface can be addressed by a replacing the support 350 with a prism 405. In some embodiments, this prism fills the optical path between the scintillator 310 and the optical system 400-P (designed to anticipate the prism 405 in the optical path). Because the bottom of the prism is perpendicular to the optical axis of the system 400-P, these rays are no longer internally reflected and are therefore transmitted into the optical system 400-P.

In some embodiments, the modifications in design for the optical system 400-P may include design for a larger working distance, to accommodate the prism in the optical path. In some embodiments, the scintillator will be attached to the prism 405 using a index-matching optical quality adhesive. In some embodiments, the prism 405 may be used in conjunction with a support 350 for the scintillator 310 as well. In this case, the prism 405 can be index-matched to the support 350 to reduce reflections from the support-prism interface. In some embodiments, the support 350 will be attached to the prism 405 using an index-matching optical quality adhesive.

In some embodiments, the optical properties of the prism 405 will be index-matched to the scintillator, so that no additional reflections occur at the scintillator—prism interface. With a suitable design of the prism comprising one face towards the optical system 400-P, a clear view of the emitted light is provided, and the image is formed with less distortion. In some embodiments, the prism 405 will be index matched to the elements in the optical system 400-P to act as a solid immersion lens. In some embodiments, the prism may comprise LuAG. LuAG has a refractive index n=1.84 at a wavelength of 535 nm, allowing the optical system 400 to be designed with LuAG elements to have an effective NA≈1.75. This can have the effect of improving the achievable resolution of the optical system 400-P.

Scintillator Variations.

Some embodiments of the invention may comprise additional variations of the elements of the scintillator assembly 300.

Figure 22A:
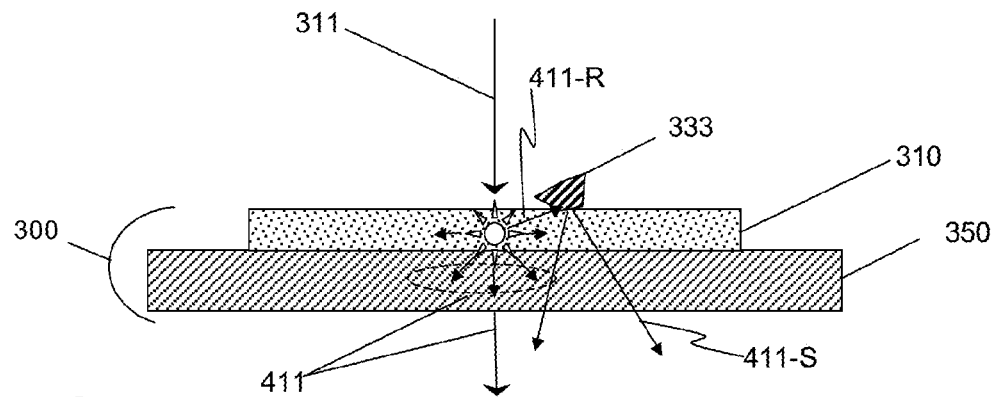
FIG. 22A illustrates scattering of scintillator emission from a dust particle when no coating is used on the scintillator.

In some embodiments, providing a coating 320 on the scintillator 310 can also reduce the impact of dust on the image. As illustrated in FIG. 22A, unless operated in an ultra-clean environment, one or more dust particles 333 can settle on the surface of the scintillator assembly 300. Light emitted by the scintillator 310 in response to the absorption of x-rays is emitted in all directions, and some emission 411-R propagates back towards the object 200. If there is no coating on the scintillator-air interface, the dust can settle directly onto the scintillator 310 itself. The emitted light 411-R can then scatter off the dust particle 333 back towards the optical system 400 as scattered light 411-S. The dust particle 333 can then appear as a bright, often out-of-focus spot in the image that has nothing to do with the object 200 being examined.

Figure 22B:
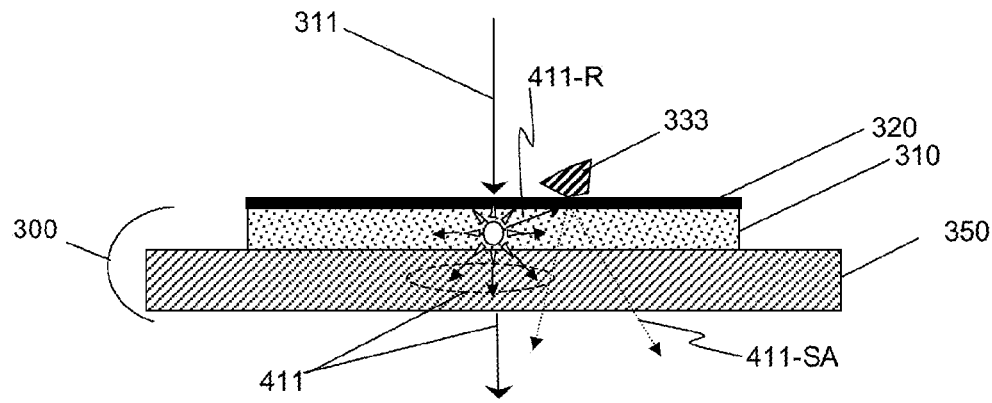
FIG. 22B illustrates scattering of scintillator emission from a dust particle when an attenuating coating is used on the scintillator according to the invention.

If, however, as shown in FIG. 22B, the scintillator assembly 300 has a coating 320 made from a material such as carbon black as manufactured by the Cabot Corporation of Boston, Mass., light 411-R emitted towards the dust particle 333 is absorbed as it passes through the coating 320, and the attenuated light that scatters off the dust particle 333 is in turn further attenuated as it again passes through the coating 320 and becomes light 411-SA propagating towards the optical system 400. The "noise" in the image from unwanted particles can therefore be significantly reduced.

Figure 22C:
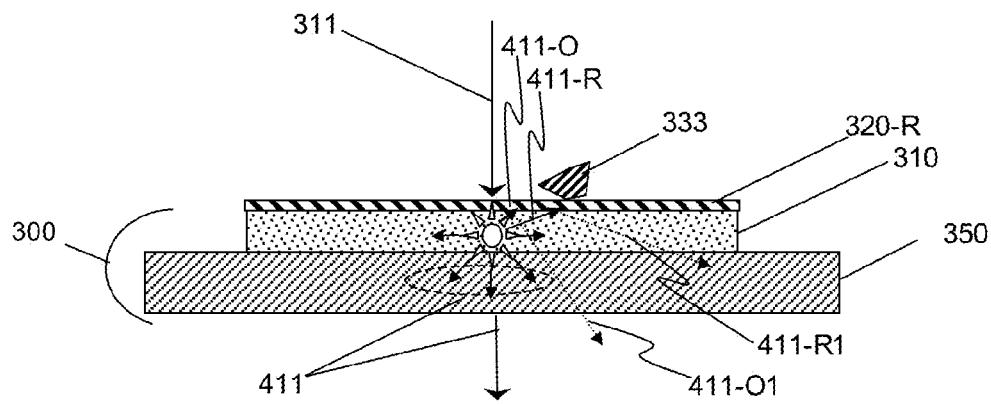
FIG. 22C illustrates scattering of scintillator emission from a dust particle when a reflective coating is used on the scintillator according to the invention.

As shown in FIG. 22C, in some embodiments, the coating 320-R may comprise a uniform layer of a reflective metal such as silver (Ag) or aluminum (Al) that can more uniformly reflect all light from the scintillator-coating interface back into the scintillator 310 and on to the optical system 400. This can have the dual advantage of reducing the susceptibility to scattering from dust particles 333 which may settle on the coating, while adding additional light to the image. Scintillator light 411-O emitted towards the object 200 will reflect off the coating 320-R and propagate back towards the optical system as reflected emitted light 411-O1. As long as the scintillator 310 is thin enough, the reflected emission 411-O1 will be collected by the optical system and be imaged close to the directly emitted visible photons 411 from the scintillator. Likewise, the emission at greater angles 411-R will reflect away from the optical system 400 as light 411-R1, and dust particles 333 will have little effect on the image.

In some embodiments, the scintillator coating 320 is fabricated from carbon as a coating of diamond or a diamond-like carbon (DLC) fabricated by chemical vapor deposition (CVD). In some embodiments, a coating of sapphire ($Al_2O_3$) may also be used. In a similar manner to the way the coating 320 prevents dust from adding unwanted light into the image, the coating 320 may also prevent light from the scintillator from scattering back from the object 200 being examined as well. The coating 320 may comprise layer of silver, aluminum or carbon deposited by evaporation or sputtering. The coating 320 may also comprise a layer of nano-particles.

As discussed above, the scintillator assembly 300 may also comprise a support 350. In some embodiments the support may be fabricated from a simple microscope slide. In other embodiments, the support 350 may be fabricated using an optical flat. In some embodiments, the support 350 may also be fabricated from a material designed to transmit UV light, such as fused silica or quartz.

Optical System Variations.

Some embodiments of the invention may comprise additional variations of the elements of the optical system 400.

In some embodiments, the lenses of the optical system 400 may comprise UV compatible optical materials, such as fused silica or quartz. In some embodiments, the lenses of the optical system 400 may comprise radiation resistant optical materials, for example glasses doped with Cerium Oxide ($CeO_2$) such as SCHOTT BK7G18, manufactured by SCHOTT Glaswerke of Mainz, Germany.

Figure 23:
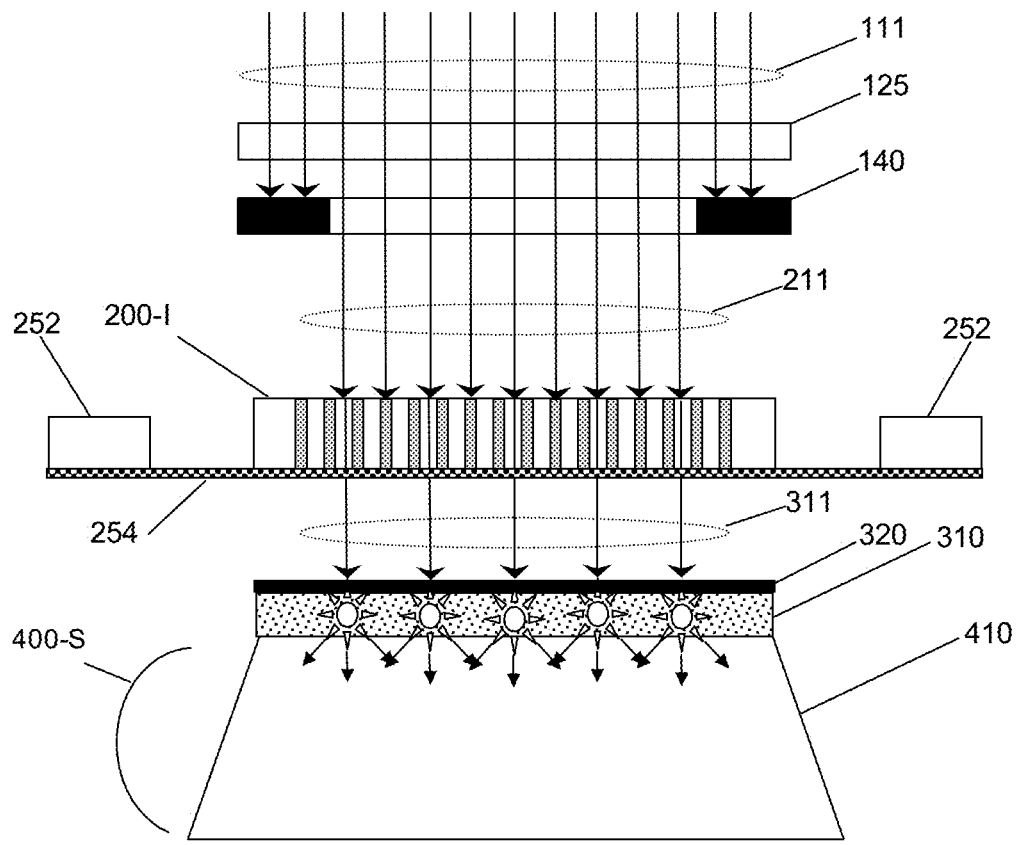
FIG. 23 illustrates an embodiment of the invention in which the scintillator is attached to the optical system.

In some embodiments, the optical system 400 is secured or fastened to the scintillator assembly 300 to prevent relative motion. In some embodiments, as illustrated in FIG. 23, the optical system 400-S can be designed so that the scintillator 310 can be mounted onto the face of objective lens 410. In such an embodiment, the lens material and the material used for the scintillator 310 may be selected to have matched refractive indices and/or matched dispersion properties. The scintillator 310 may be attached to the objective lens 410 using an index-matching adhesive. In some embodiments, the scintillator 310 as attached to the housing of the objective lens 410. In some embodiments, the scintillator 310 attached to the objective lens 410 or its housing may have a coating 320, as described above. In some embodiments, the scintillator 310 attached to the objective lens 410 or its housing may have an additional support 350, as described above, which is also attached to the objective lens 410 or its housing.

In some embodiments, such as the embodiment described above in which the space between the scintillator 310 and the optical system 400-P comprises a prism 405, or in other designs for the optical system 400 in which a "solid immersion lens" is used, the materials for the scintillator, prism or solid immersion lens, as well as the lenses of the optical system 400, may be selected to have matched refractive indices. In some embodiments, the materials for the scintillator, prism or solid immersion lens, as well as the lenses of the optical system 400, may be selected to have matched dispersion characteristics over a defined wavelength range.

The optical system may be designed to bend the optical path, so that the image is not formed along the same axis as the direction in which the x-rays are propagating. This can further isolate the image detector 500 from potential harmful exposure to x-rays.

Referring again to FIG. 19, one approach to remove the image detector from the x-ray beam path is the use of a fiber optic bundle 505 or array to collect the image formed by the optical system 400 and convey it to the modified image detector 500-F.

In another embodiment, an optical path comprising a beamsplitter or mirror can be used to reflect the optical portions of the image onto an image detector 500 while transmitting the x-rays.

Figure 24:
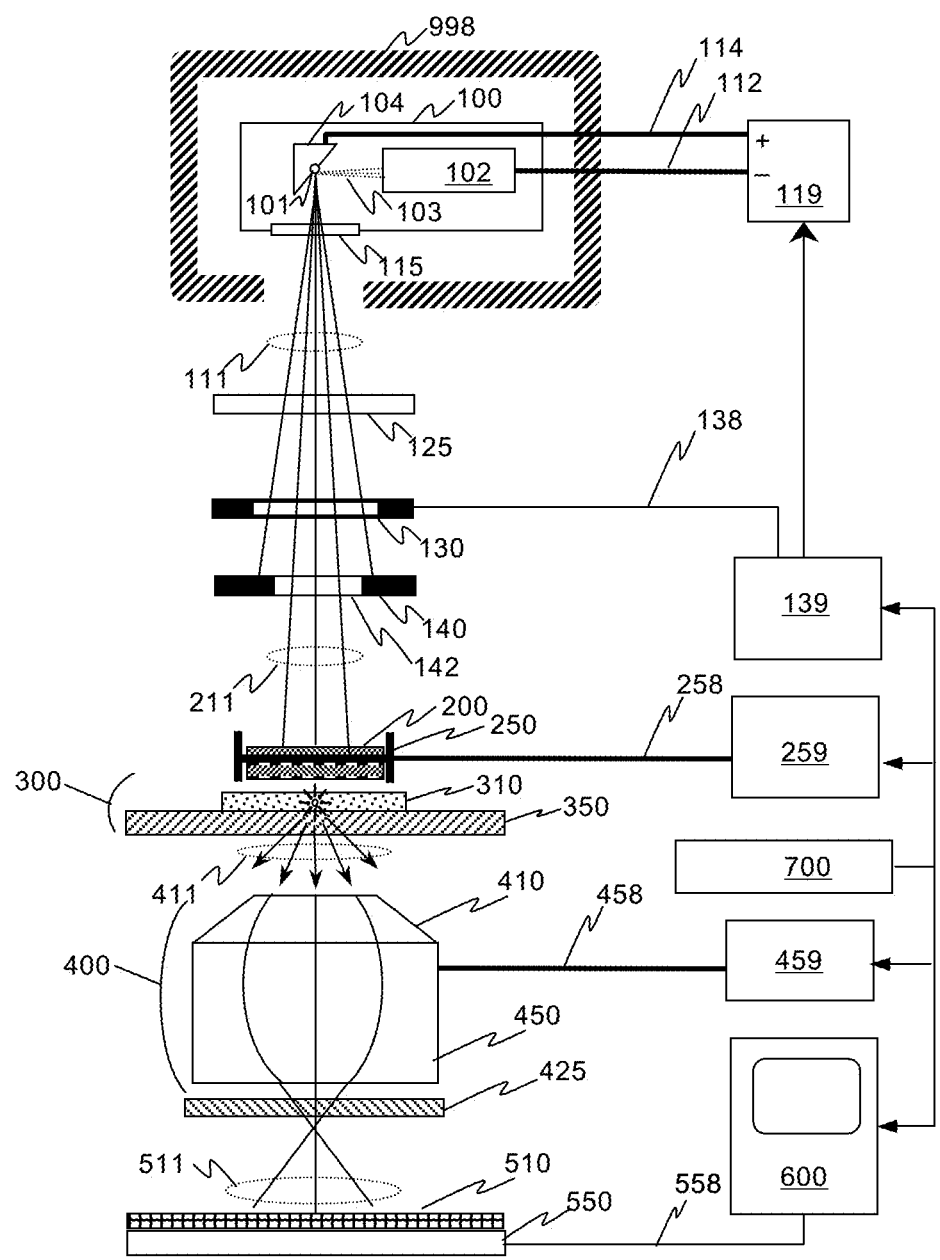
FIG. 24 illustrates a cross-section overview for a system additionally comprising control systems for the optical system.

Referring now to FIG. 24, additional, elements 425 in the optical system may also be used to introduce additional properties to the image. In some embodiments, additional elements 425 may comprise a color filter, to select specific wavelengths emitted by the scintillator 310. This filter may, for example, select visible scintillator emission for imaging while blocking or absorbing UV emission. This filter may, for example, select UV scintillator emission for imaging while blocking or absorbing visible emission.

In some embodiments, as illustrated in FIG. 24, the optical system 400 can be governed by a controller 459 through a connector 458. The optical system controller 459 may manipulate mechanical elements of the optical system 400 to change the focus, the tilt of the image plane, to coordinate lens rotation with the rotation of the object 200, to adjust internal apertures to change the image intensity, to adjust filters or other additional elements 425, and other lens adjustments that will be known to those skilled in the art.

In some embodiments, the signals from the optical system controller 459 will be coordinated with signals to the mount 250 provided by the mount controller 259. In some embodiments, the signals from the optical system controller 459 will be coordinated with signals to the shutter 130 provided by the shutter controller 139. In some embodiments, the signals from the optical system controller 459 will be coordinated with signals to the x-ray source 100 provided by the source power supply 119. In some embodiments, some or all of the coordination of the various controllers will be directed by programs run using the one or more computer systems 700.

In some embodiments, the control programs for the optical system 400 executed using the one or more computer systems 700 will have auto-focus algorithms that adjust the image for best contrast and definition. In some embodiments, the control programs for the optical system 400 executed using the computer system 700 will have look-up tables for a pre-focus map. In some embodiments, the control programs for the optical system 400 executed using the computer system 700 will have coordinated motions for both the object 200 and mount 250 and the optical system 400. In some embodiments, the control programs for the optical system 400 executed using the computer system 700 will have alignment algorithms to allow a specific region of an object 200 to be recognized and examined.

Detector Variations.

Some embodiments of the invention may comprise additional variations of the elements of the image detector 500.

In some embodiments of the invention, images are obtained continuously while the object 200 is moving using a time-delay and integration (TDI) device or method. The TDI detector may be based on a CCD camera that is synchronized with the motion of the mount 250 or stage.

In some embodiments, the image detector 500 will produce a signal with components corresponding to a pixel number and a corresponding intensity. In some embodiments, the image detector 500 will produce a signal with components corresponding to coordinate locations and a corresponding intensity. In some embodiments, this signal is transmitted over a connector 558 to a system of electronics 600 for additional signal processing and possible display.

In some embodiments of the invention, the system of electronics 600 associated with the detector will analyze the image signal and perform adjustments such as image alignment, brightness adjustment, contrast enhancement, digital filtering, or fast Fourier transforms (FFTs). In some embodiments, single images or multiple images will be analyzed to allow 3D reconstructions of the structures in the object, including algebraic reconstructions, backpropagation algorithms, adaptive kernel filtering, computed laminography (CL), as well as other reconstruction techniques that are based on some degree of pre-knowledge of the intended layout. Such pre-knowledge may comprise design databases such as GDS-II or OASIS data, specifications for planarity of layers, material properties, and the anticipated geometry and number of layers.

In some embodiments, the system of electronics 600 will additionally comprise a display that allows an operator to view the image in real time. In some embodiments, the system of electronics will comprise control programs that communicate operator input or automatically generated input to the various power supplies and controllers 119, 139, 259, and 459 for the x-ray source 100, the shutter 130, the mount 250 holding the object 200, and the optical system 400. In some embodiments, the network that interfaces the computer system 700 with the various controllers 119, 139, 259, 459, and 600 may be an Ethernet network. In some embodiments, the images may be accessed by the computer system 700 using an internet connection (via packets) or a serial bus (e.g. USB 2.0).

Control programs and image analysis procedures may comprise the operation of software programs for equipment control and image analysis such as those written in LabVIEW® by National Instruments Corp. of Austin, Tex., MatLab® by MathWorks, Inc. of Natick, Mass., or public domain image processing programs such as ImageJ, developed by the National Institutes of Health in Bethesda, Md.

Computer System Detail and Variations.

Some embodiments of the invention may comprise additional variations of the elements of the one or more computer systems 700.

In some embodiments, a computer system 700 will comprise stored control programs that communicate instructions to the various power supplies and controllers 119, 139, 259, 459 for the x-ray source 100, the shutter 130, the mount 250 holding the object 200, and the optical system 400, as well as for collecting corresponding images from the system of electronics 600 gathering image signals from the image detector 500. These instructions can be pre-programmed recipes for specific measurement sites, or a general program for inspection of an entire object 200 or portion thereof.

In some embodiments, the computer system 700 may also be used for processing images. This may include image alignment, sub-pixel interpolation, or modification of the image histogram such as brightness or contrast adjustments.

In some embodiments, the computer system 700 may also be used for three-dimensional image reconstruction. In this case, two or more images are used to generate a three-dimensional representation or model of the object being examined. The images may be obtained by changing the object orientation with respect to the x-ray beam (or vice versa), for example. These reconstructions may comprise any one of, or a combination of, algebraic reconstructions, backpropagation methods, or Fourier transform methods. Furthermore, these reconstruction methods may incorporate knowledge of the object structure or materials to aid in the reconstruction. For example, the knowledge of the number of interconnect layers may be used to improve the reconstruction.

Figure 25:
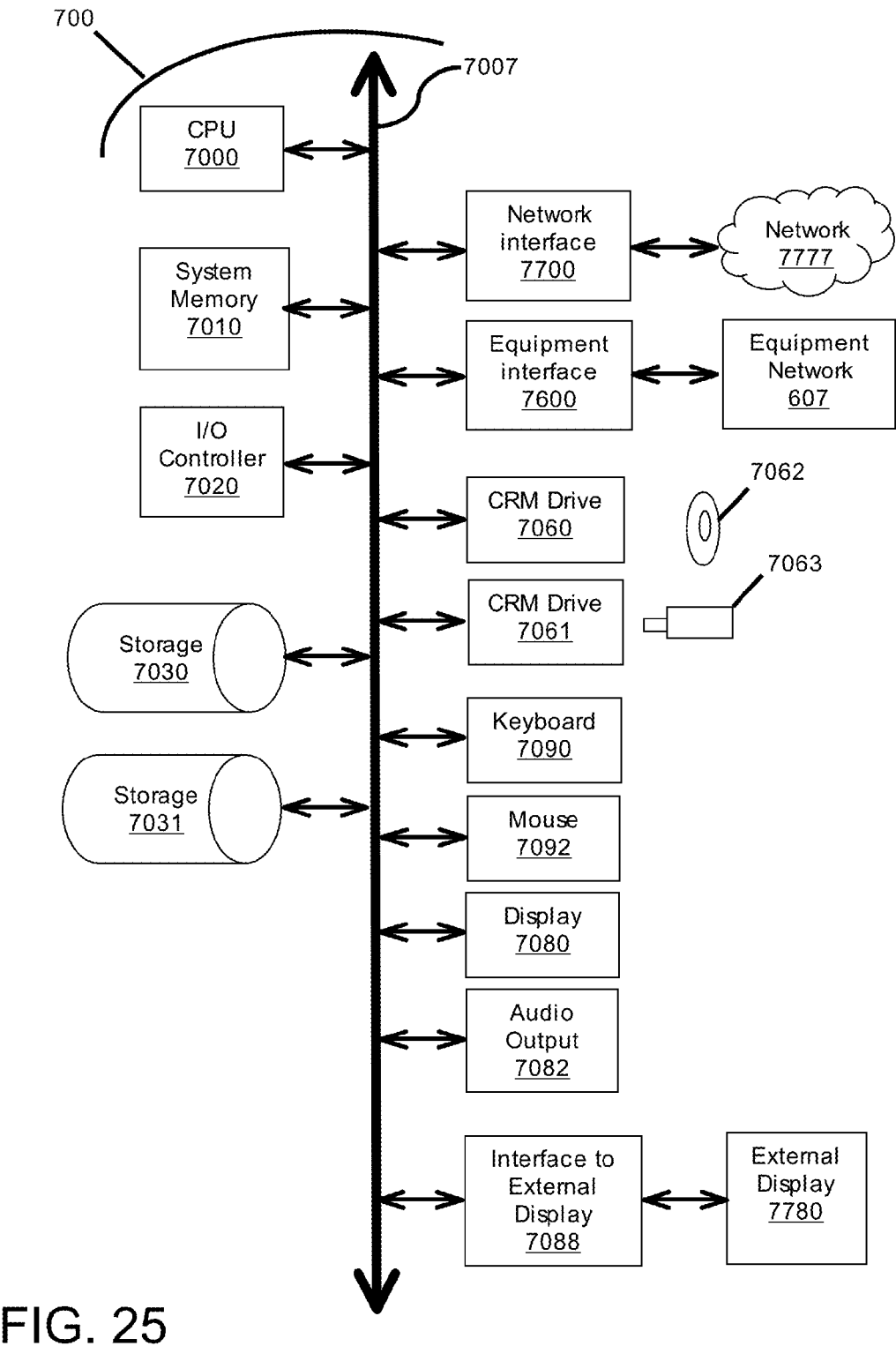
FIG. 25 illustrates a block diagram of a computer system as used according to the invention.

FIG. 25 illustrates a block diagram of an exemplary computer system that can serve as a platform for portions of embodiments of the present invention. Computer system 700, as described above, can comprise a bus 7007 which interconnects major subsystems of computer system 700, such as a central processing unit (CPU) 7000, a system memory 7010 (typically random-access memory (RAM), but which may also include read-only memory (ROM), flash RAM, or the like), an input/output (I/O) controller 7020, one or more data storage systems 7030, 7031 such as an internal hard disk drive or an internal flash drive or the like, a network interface 7700 to an external network 7777, such as the Internet, a fiber channel network, or the like, an equipment interface 7600 to connect the computer system 700 to a network 607 of other electronic equipment components, and one or more drives 7060, 7061 operative to receive computer-readable media (CRM) such as an optical disk 7062, compact disc read-only memory (CD-ROM), compact discs, floppy disks, universal serial bus (USB) thumbdrives 7063, magnetic tapes and the like. The computer system 700 may also comprise a keyboard 7090, a mouse 7092, and one or more various other I/O devices such as a trackball, an input tablet, a touchscreen device, an audio microphone and the like. The computer system 700 may also comprise a display device 7080, such as a cathode-ray tube (CRT) screen, a flat panel display or other display device; and an audio output device 7082, such as a speaker system. The computer system 700 may also comprise an interface 7088 to an external display 7780, which may have additional means for audio, video, or other graphical display capabilities for remote viewing or analysis of results at an additional location.

Bus 7007 allows data communication between central processor 7000 and system memory 7010, which may comprise read-only memory (ROM) or flash memory, as well as random-access memory (RAM), as previously noted. The RAM is generally the main memory into which the operating system and application programs are loaded. The ROM or flash memory can contain, among other code, the basic input/output system (BIOS) that controls basic hardware operation such as the interaction with peripheral components. Applications resident with computer system 700 are generally stored on storage units 7030, 7031 comprising computer readable media (CRM) such as a hard disk drive (e.g., fixed disk) or flash drives.

Data can be imported into the computer system 700 or exported from the computer system 700 via drives that accommodate the insertion of portable CRM drives, such as an optical disk 7062, a USB thumbdrive 7063, and the like. Additionally, applications and data can be in the form of electronic signals modulated in accordance with the application and data communication technology when accessed from a network 7777 via network interface 7700. The network interface 7700 may provide a direct connection to a remote server via a direct network link to the Internet via an Internet PoP (Point of Presence). The network 7700 may also provide such a connection using wireless techniques, including a digital cellular telephone connection, a Cellular Digital Packet Data (CDPD) connection, a digital satellite data connection or the like.

Many other devices or subsystems (not shown) may be connected in a similar manner (e.g., document scanners, digital cameras and so on). Conversely, all of the devices shown in FIG. 25 need not be present to practice the present disclosure. In some embodiments, the devices and subsystems can be interconnected in different ways from that illustrated in FIG. 25. The operation of a computer system 700 such as that shown in FIG. 25 is readily known in the art and is not discussed in further detail in this application.

Code to implement the present disclosure can be stored on computer-readable storage media such as one or more of: the system memory 7010, internal storage units 7030 and 7031, an optical disk 7062, a USB thumbdrive 7063, one or more floppy disks, or on other storage media. The operating system provided for computer system 700 may be any one of a number of operating systems, such as MS-DOS®, MS-WINDOWS®, UNIX®, Linux®, OS-X® or another known operating system.

Moreover, regarding the signals described herein, those skilled in the art will recognize that a signal can be directly transmitted from one block to another, between single blocks or multiple blocks, or can be modified (e.g., amplified, attenuated, delayed, latched, buffered, inverted, filtered, or otherwise modified) by one or more of the blocks.

Further Embodiments Using the X-Ray Imaging System

So far, this disclosure has described embodiments of an x-ray system that can rapidly collect images of high quality at high resolution with a large field of view. The images so generated can reveal information about the internal structures of an IC, a chip package or assembly without damaging the object itself. As a result, these electronic images can be used for various metrology systems and inspection systems. These metrology and inspection results can in turn be used as a part of manufacturing process control systems using statistical process control (SPC), or for process yield management and improvement systems that enable manufacturing products with higher yield.

Metrology.

The images from the disclosed x-ray system may be used for metrology. This may include measuring the sizes and/or shapes of features in the object being examined, such as the diameter or side-wall angle of TSVs. The metrology may also include measuring features at different places on the object and comparing them to each other, or comparing them to a standard, as well as reporting the measurements.

The images may also be used to reverse-engineer the internal structure of the object being examined. For example, the images or three-dimensional reconstruction may be used to generate a list of electrical connections or a file to be used for creating a reticle for printing the circuits. The images may be used to detect changes in the object structure from nominal. These images may also be used to identify certain features in the object that may be of interest. They may be used to reverse engineer a product, determining the materials and internal structures of an object non-destructively.

Figure 26:
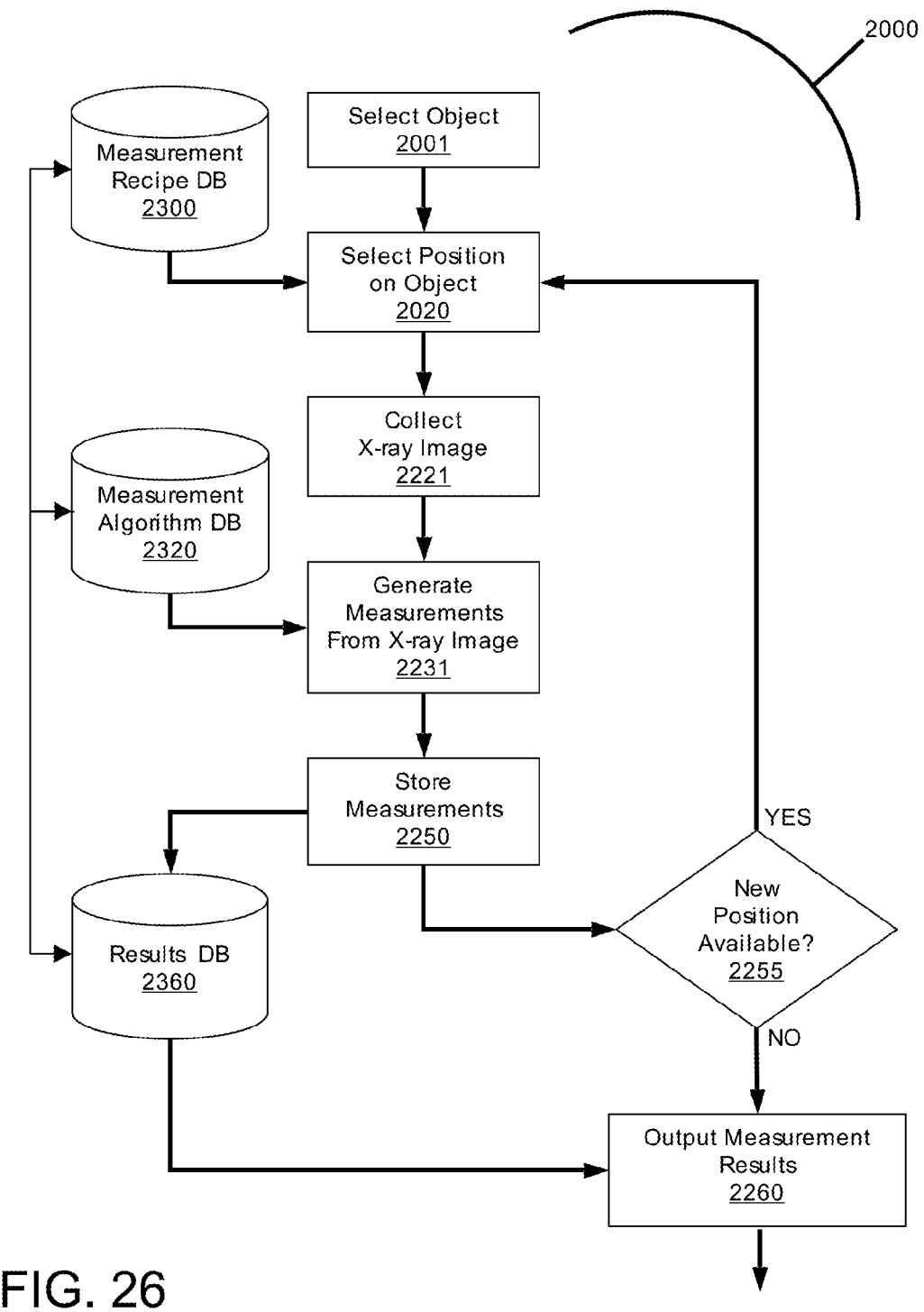
FIG. 26 illustrates a typical process flow for making a metrology measurement using the x-ray system according to the invention.

FIG. 26 illustrates one embodiment of a method for conducting metrology using an x-ray system as disclosed in this application.

This method for metrology 2000 has, as its first step 2001, the selection of an object to be examined. This object may be blank incoming material before processing begins, or a partly or fully manufactured integrated circuit or portion thereof, a 2.5D IC or 3D IC package, a silicon interposer with TSVs, a C4 flip chip interconnect package, a multi-chip module (MCM), or any one of a number of the objects, devices and structures disclosed in this application, as well as others that will be known to those skilled in the art.

In the next step 2020, a particular position on the object is selected for measurement. This may be selected manually, or it may be selected by reference to a stored program or recipe stored in a Measurement Recipe Database 2300.

In the next step 2221, the object is mounted in the x-ray system according to the disclosed invention, and one or more x-ray images are collected. The x-ray system will typically comprise a source, preferably with high x-ray flux, a mount to position the object, a scintillator, an optical system, and an optical image detector, as has already been disclosed in detail in this application. In typical embodiments according to the invention, the ratio of the source spot size to the resolution of the optical imaging system and detector combination will be greater than 1, while the resolution will be less than 10 microns.

In the next step 2231, the one or more x-ray images are gathered and the image data analyzed for certain features, such as CD measurements. Feature linewidths, diameters, shapes, thicknesses, depths, spaces between objects, line edge roughness, etc. may be calculated based on the x-ray image data collected. Some of these calculations may be done manually, but more commonly, a stored computer program comprising image analysis algorithms and image comparison procedures, as well as stored files of reference images and design databases, may be provided in a Measurement Algorithm Database 2320. In some embodiments, these algorithms may include image processing algorithms, such as Fourier Transforms, contrast enhancement, shape or pattern recognition, etc. In some embodiments, these algorithms may be called automatically as part of the recipe for measurement stored in the Measurement Recipe Database 2300. In some embodiments, these algorithms may combine data from two or more images to compute 3D depth information. Other metrology protocols will be known to those skilled in the art.

In the next step 2250, the results of the analysis of the image are stored as metrology results in a Results Database 2360. These results may be indexed or stored with reference to the Measurement Recipe Database 2300 or the Measurement Algorithm Database 2320.

Once the images and measurements have been collected for one position on the object, the next step 2255 comprises a determination of whether all positions required by the recipe for object being examined have been measured, or if the recipe requires additional measurements. If the determination is YES, a new position is determined and then selected on the object according to the earlier mentioned step 2020, x-ray measurements generated 2221, and the measurement results generated 2231 and stored 2250, and the determination 2255 is again made. If the determination is NO, i.e. that all required measurement data for the object has been gathered, the last step 2260 outputs the measurement results, in some embodiments calling them from the Results Database 2360. The output results can be in the form of a collection of data, or further prepared as a formatted report to be printed, filed and possibly archived and reviewed at a later time.

Although this is one embodiment of a metrology process using the x-ray system according to the invention, it will be recognized that variations on this process will be known to those skilled in the art of metrology. In some embodiments, all x-ray images may be gathered before any analysis is carried out. In some embodiments, the process may be entirely automatic, governed by one or more computers. In some embodiments, the one or more computers controlling the metrology process may also be one or more computers controlling the x-ray system itself.

This metrology process 2000 or similar variations may be used to examine individual objects to determine their structure and properties. However, this metrology process 2000 or similar variations can be inserted into a manufacturing process as a form of process control. Such process control techniques, such as statistical process control (SPC) or others that will be known to those skilled in the art, measure predefined structures on an ongoing basis and alert the operator when a process variable is either out of specification, or is drifting out of specification. Often, a body of knowledge about the process will have been built up over the history of the manufacturing line, and the process control alerts can be a signal that triggers some predefined process improvement. For example, an alert that wafers or chips processed by a particular tool now have linewidth variation that is increasing relative to its previous performance may trigger preventive maintenance for that particular tool.

Figure 27:
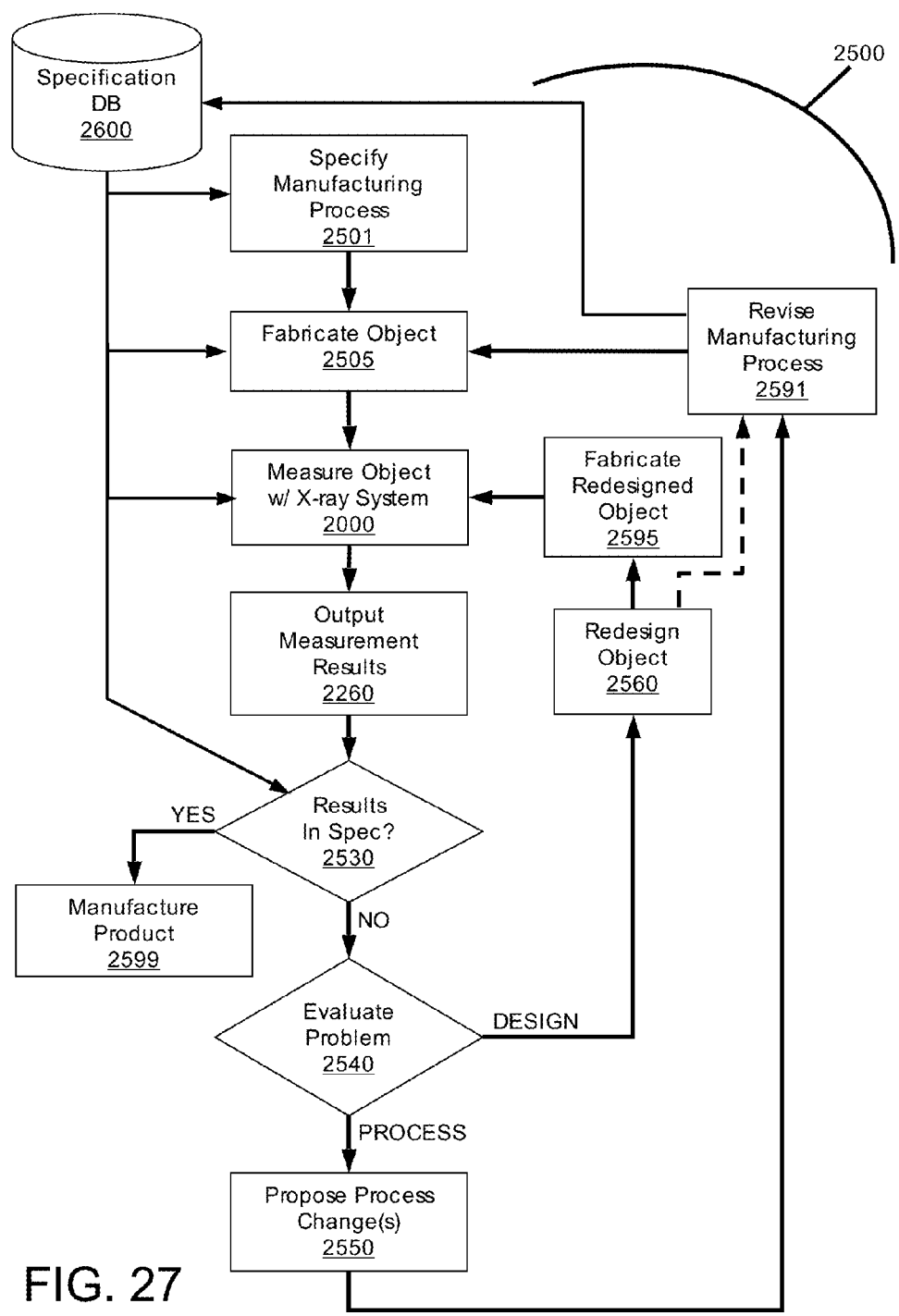
FIG. 27 illustrates a typical process flow for using metrology measurements gathered according to the process flow of FIG. 26 for manufacturing process control.

FIG. 27 illustrates one embodiment of a method for conducting process control 2500 for a manufacturing process using the metrology process 2000 comprising measurement using an x-ray system as disclosed in this application.

In the initial step 2501, the manufacturing process is defined and identified. This may be a small single unit process, such as a wafer lithography stepper and track combination, or an entire multi-step process for fabricating an entire integrated circuit, or a packaging process for assembling multiple integrated devices into one package. The manufacturing recipe or recipes and the associated specification values and control limits may be stored in one or more Specification Databases 2600.

Once the manufacturing line is operational, in the next step 2505, one or more objects are fabricated according to the predefined process, calling on the Specification Database 2600 for recipes as needed. The object may be incoming material to the manufacturing process, a partially manufactured product, a test or pilot wafer, a fully manufactured IC, a wafer prior to dicing, chips from a wafer after dicing, chips partially or fully assembled in a 3D IC package, an interposer, incoming packaging boards or material, partially mounted ICs in packages, a fully assembled IC package, or any one of a number of products and by-products associated with a manufacturing process.

In the next step 2000, the metrology process disclosed above is executed to generate measurement results for the fabricated object using the x-ray system as disclosed. The Specification Database 2600 may provide some or all of the data required by the Measurement Recipe Database 2300 to direct the metrology process.

The next step is the output step of metrology process 2000, which was the step of outputting measurement results 2260.

In the next step 2530, the measurement results are evaluated according to information provided by the specification database 2600, and the particular process variables and parameters are determined and compared to their historical values.

If this step 2530 determines that all processes are functioning within the predetermined parameters as defined in the Specification Database 2600, then the determination is YES, and the product manufacturing 2599 proceeds. The products, such as integrated circuits, IC packages, etc., are within the predefined specification, and the execution of the method for conducting process control 2500 helps to identify problems before significant amounts of material are manufactured incorrectly, and have to be scrapped. The cost per working unit of the product is therefore reduced.

However, if this step 2530 determines that a measurement is currently out of specification, or that certain derived parameters, such as the standard deviation of a process variable, are out of specification, or any one of a number of predefined conditions are met, then the determination is NO.

In this case, the next step 2540 is an evaluation of the deviant conditions, either manually or by automated means using one or more computers, and a determination of what might be changed to fix it. In some embodiments, there may be two major classifications of problems: those arising from product DESIGN, and those arising from a manufacturing PROCESS.

DESIGN problems will typically appear repeatedly as systematic failures for parts when the design has the same configuration. One example of a design problem is the bridging of interconnect lines that have been fabricated too close together, i.e. when the space between the lines cannot be resolved by the lithography stepper printing the lines. Another example of a design problem is when TSVs in an interposer have simply been designed to be smaller than the manufacturing process can reliably support.

If the result of this step 2540 is a determination that there is a DESIGN problem, the next step 2560 is to redesign the object. For the examples given above, the if two nearby lines are bridging, a new design which separates these lines will be created; likewise, if TSVs are too small, or have an un-manufacturable aspect ratio, a new design with larger TSVs, or with multiple (i.e. redundant) vias for critical connections may be created.

Once the new design has been created, the next step 2595 is to fabricate the re-designed object, and then proceed to again make measurements 2000 with the x-ray system, output the measurement results 2260, and evaluate the measurement results 2530 as before.

In some cases, a redesign may also require a step 2591 in which a revision to the manufacturing process is also made. This revision may in turn require a change to the data in the Specification Database 2600, which will now comprise recipes and specifications that correspond to the re-designed product.

If the result of this step 2540 is a determination that there is a PROCESS problem, the next step 2550 is to determine any changes in the manufacturing process. For the examples given above, comparable process problems can also occur. Two lines that are fabricated close to each other may normally be printable, but a process may no longer be reliably printing them. This may indicate a focus error in one or more of the steppers used to print the IC layer containing the line pairs. Likewise, vias that are normally manufactured reliably may now have internal voids, making electrical contact unreliable. This may require a change in the copper deposition process for the TSVs, or the adaptation of an annealing process that reduces susceptibility to void growth.

In the next step 2591, the changes are made to the manufacturing process. Corresponding changes to the data in the Specification Database 2600 may also be made, so that the Database 2600 will now comprise recipes and specifications that correspond to the re-engineered process.

Inspection.

The images from the disclosed x-ray system may be used for inspection. By comparing these gathered images to those from another nominally identical device, or to an idealized estimate of how the design should appear in the manufactured part, or by comparison with a pre-determined set of design rules, defects can be identified, and the object under investigation set aside for further investigation.

The images or a reconstructed model may then be used to perform defect detection on the object being examined. Defects may be classified as critical or non-critical, or sorted by type. The location of defects may be reported, as well a Pareto analysis of defects by size, shape, location or other relevant parameter. These results may be used for statistical process control.

Figure 28:
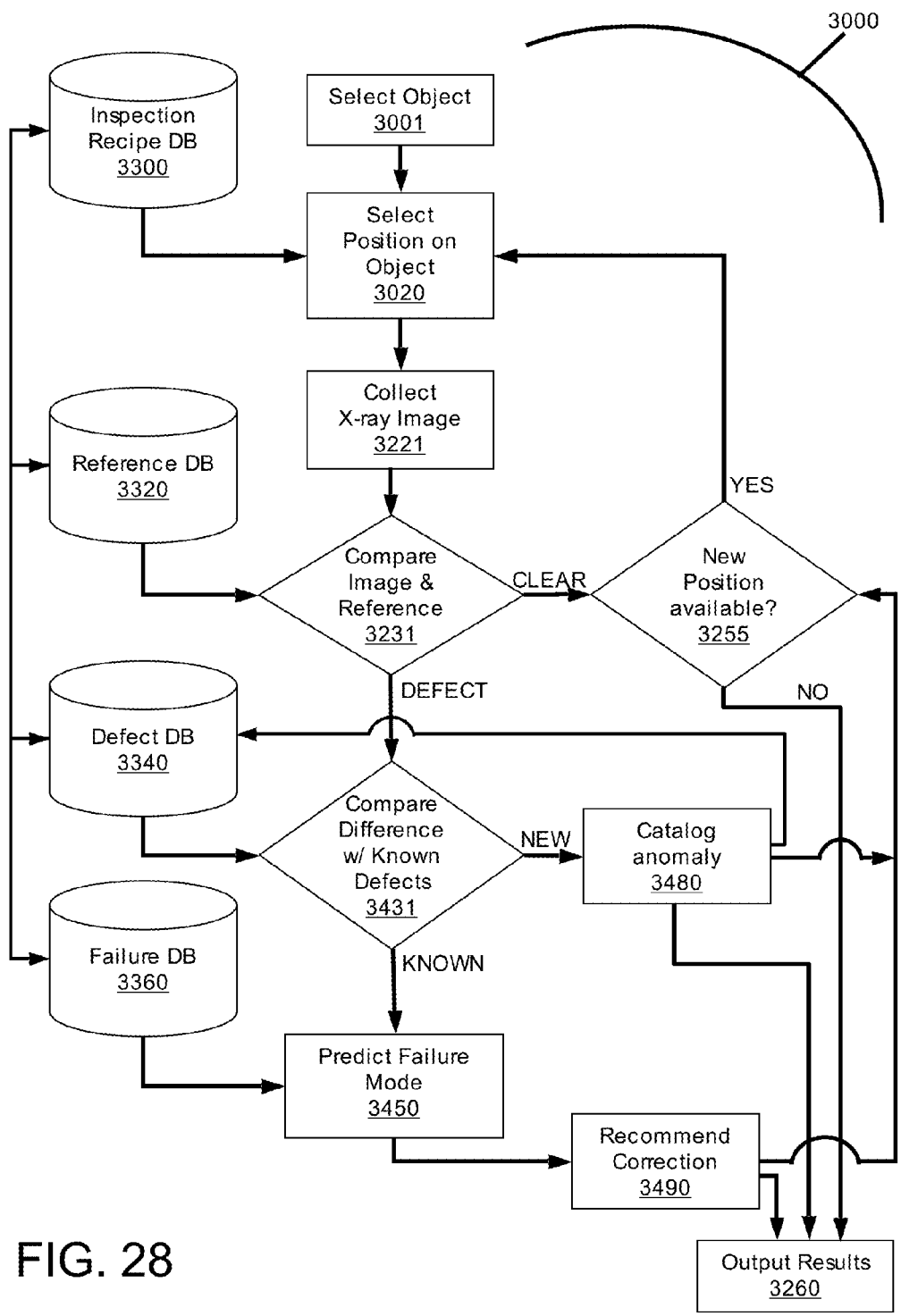
FIG. 28 illustrates a typical process flow for carrying out inspection using the x-ray system according to the invention.

FIG. 28 illustrates one embodiment of a method for conducting inspection using an x-ray system as disclosed in this application.

This method for inspection 3000 has, as its first step 3001, the selection of an object to be examined. This object may be blank incoming material before processing begins, or a partly or fully manufactured integrated circuit or portion thereof, a 2.5D IC or 3D IC package, a silicon interposer with TSVs, a C4 flip chip interconnect package, a multi-chip module (MCM), or any one of a number of the objects, devices and structures disclosed in this application, as well as others that will be known to those skilled in the art.

In the next step 3020, a particular position on the object is selected for measurement. This may be selected manually, or it may be selected by reference to a stored program or recipe stored in an Inspection Recipe Database 3300.

In the next step 3221, the object is mounted in the x-ray system according to the disclosed invention, and one or more x-ray images are collected. The x-ray system will typically comprise a source, preferably with high x-ray flux, a mount to position the object, a scintillator, an optical system, and an optical image detector, as has already been disclosed in detail in this application. In typical embodiments according to the invention, the ratio of the source spot size to the resolution of the optical imaging system and detector combination will be greater than 1, while the resolution will be less than 10 microns.

In the next step 3231, the one or more x-ray images are gathered and the image data analyzed for indications of defects. The determination of the presence or absence of defects may be carried out by conducting an analysis of the data in the x-ray image alone, evaluating the x-ray image data for the signature of various known defects (such as black dots for voids, anomalous bright spots, etc.) using algorithms that are the same as, or similar to, those used for metrology analysis as described above. The determination of the presence or absence of defects may be carried out by comparing the image data to data previously gathered for a similar section of another object (such as is done in die-to-die inspection), or it may be carried out by comparison to a corresponding portion of a reference database of design data (such as is done in die-to-database inspection). Some of these calculations may be done manually, but more commonly, a stored computer program comprising image analysis algorithms and image comparison procedures, as well as stored files of reference images and design databases, may be provided in a Reference Database 3320. In some embodiments, these algorithms may include image processing algorithms, such as Fourier Transforms, contrast enhancement, shape or pattern recognition, etc. In some embodiments, these algorithms may be called automatically as part of the recipe for measurement stored in the Inspection Recipe Database 3300. In some embodiments, these algorithms may combine data from two or more images to compute 3D depth information. Other inspection protocols will be known to those skilled in the art.

In the next step 3231, the data corresponding to the one or more x-ray images of the object will be analyzed for potential defects, using any or all of the techniques mentioned above. If none of the analyses conducted on the one or more x-ray images suggests the presence of a defect in the location of the object corresponding to the x-ray image, the determination for the set of locations is CLEAR. If at least one analysis of the image shows an anomaly, the determination for the set of locations is DEFECT.

If the determination for an x-ray image is CLEAR, the next step 3255 comprises a determination of whether all positions required by the recipe for object being examined have been measured, or if the recipe requires additional measurements. If the determination is YES, a new position is determined and then selected on the object according to the earlier mentioned step 3020, x-ray measurements are generated 3221, and the inspection results for the new location evaluated 3231 and the determination 3255 is again made.

If the determination is DEFECT, i.e. one of the analysis procedures indicates that the there is a potential defect at the location, further analysis of the image is carried out.

In this case, the next step 3431 is the comparison of the signature of the result of the defect analysis with a Defect Database 3340, which, among other things, may comprise known signatures of known types of defects. For example, an irregular, skinny blob detected within a structure corresponding to a TSV may represent a signature of a void within the copper. As another example, the comparison of an image with a corresponding portion of the design database may indicate that a interconnect line should be present when there is no corresponding feature in the x-ray image.

If the determination of the comparison step 3431 is that there is NO recognition of a particular defect type, the potential defect at this location is determined to be NEW. The next step 3480 will be will be to catalog the data associated with this anomalous result, and in some embodiments also storing this new data in the Defect Database 3340. After this, the next step 3255 comprises a determination of whether all positions required by the recipe for object being examined have been measured, or if the recipe requires additional measurements. If the determination is YES, a new position is determined and then selected on the object according to the earlier mentioned step 3020, x-ray measurements are generated 3221, and the inspection results for the new location evaluated 3231 and the determination 3255 is again made. If the determination is NO, then the next step 3260 may comprise outputting the final results for the inspection.

If the determination of the comparison step 3431 is the recognition of a particular defect type, the location is determined to be KNOWN. The next step 3450 will be the prediction of any failure mode known to occur with this particular defect type. This prediction 3450 may be carried out with reference to a Failure Database 3360, which may comprise information on historical records or theoretical models for the object, process, and product being inspected.

Once the failure mode is predicted, steps to prevent future defects and product failures may be made. In the next step 3490, a correction to the process may be recommended, either by an automated computer program based on historical data for the process, or based on an engineering evaluation of the defect type and failure mode.

Once the correction is recommended, the next steps are two-fold. On the one hand, one of the next steps 3260 comprises outputting the inspection results, typically along with the recommended changes. On the other hand, one of the next steps 3255 comprises a determination of whether all positions required by the recipe for object being examined have been measured, or if the recipe requires additional measurements. If the determination is YES, a new position is determined and then selected on the object according to the earlier mentioned step 3020, x-ray measurements are generated 3221, and the inspection results for the new location evaluated 3231. If the determination is NO, then the next step 3260 may comprise outputting the final results for the inspection.

The output results 3260 can be in the form of a collection of data, or further prepared as a formatted report to be printed, filed and possibly archived and reviewed at a later time. They may contain a list of identified electrical connections (such as a netlist), a listing of geometric polygons (such as a layout), a listing of locations and the number of defects detected, a listing such as a Pareto chart of the types of defect detected. Counts of both defect and regular features sizes and shapes may also be included. Means may be provided for manual review of defects, or for an automated review of defect.

Although this is one embodiment of an inspection process using the x-ray system according to the invention, it will be recognized that variations on this process will be known to those skilled in the art of inspection. In some embodiments, all x-ray images may be gathered before any analysis is carried out. In some embodiments, the process may be entirely automatic, governed by one or more computers. In some embodiments, the one or more computers controlling the inspection process may also be one or more computers controlling the x-ray system itself.

This inspection process 3000 or similar variations may be used to examine individual objects to determine their structure and properties. However, this inspection process 3000 or similar variations can be inserted into a manufacturing process as a form of yield management. Such yield management techniques will be known to those skilled in the art, and are commonly used to inspect manufactured products or samples from a manufacturing line on an ongoing basis, and alert the operator when a defects or anomalies are beyond certain specified limits. Often, a body of knowledge about the process will have been built up over the history of the manufacturing line, and the defect statistics can be used to produce a signal that triggers some predefined process improvement. For example, an alert that wafers or chips processed using a particular tool now have an increase in dust particles larger than 10 microns may trigger preventive maintenance for that particular tool.

Figure 29:
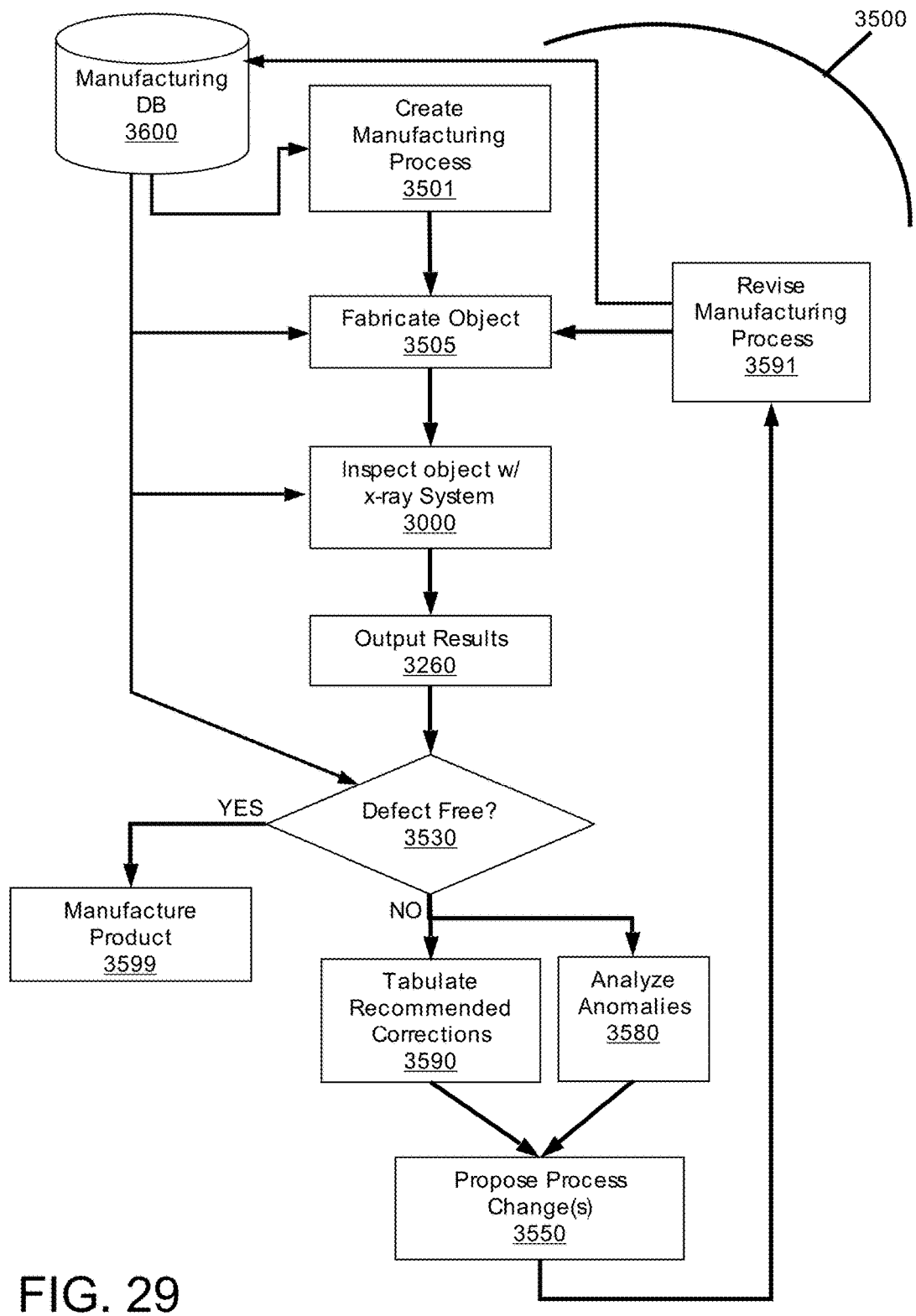
FIG. 29 illustrates a typical process flow for using inspection results gathered according to the process flow of FIG. 28 for yield management in a manufacturing process.

FIG. 29 illustrates one embodiment of a method for conducting yield management 3500 using the inspection process 3000 comprising inspection using an x-ray system as disclosed in this application.

In the initial step 3501, the manufacturing process is defined and identified. This may be a small single unit process, such as a wafer lithography stepper and track combination, or an entire multi-step process for fabricating an entire integrated circuit, or a packaging process for assembling multiple integrated devices into one package. The manufacturing recipe or recipes and the associated specification values and control limits may be stored in one or more Manufacturing Databases 3600.

Once the manufacturing line is operational, in the next step 3505, one or more objects are fabricated according to the predefined process, calling on the Manufacturing Database 3600 for recipes as needed. The object may be incoming material to the manufacturing process, a partially manufactured product, a test or pilot wafer, a fully manufactured IC, a wafer prior to dicing, chips from a wafer after dicing, chips partially or fully assembled in a 3D IC package, an interposer, incoming packaging boards or material, partially mounted ICs in packages, a fully assembled IC package, or any one of a number of products and by-products associated with a manufacturing process.

In the next step 3000, the inspection process disclosed above is executed to generate inspection results for the fabricated object using the x-ray system as disclosed. The Manufacturing Database 3600 may provide some or all of the data to direct the inspection process.

The next step is the final step of the inspection process 3000, which was the step of outputting results 3260.

In the next step 3530, the inspection results are evaluated to see if the process can be labeled "Defect Free", according in part to the definitions and specifications provided by the Manufacturing Database 3600. This step may comprise determining particular defect statistics and yield parameters and comparing them to their historical values.

If this step 3530 determines that all processes are functioning within the predetermined defect and yield parameters as defined in the Manufacturing Database 2600, then the determination is YES, the process can be labeled "Defect Free", and the product manufacturing 3599 proceeds. The products, such as integrated circuits, IC packages, etc., are within the predefined yield, and the execution of the yield management process 3500 helps to identify problems before significant amounts of material are manufactured incorrectly, and have to be scrapped. The cost per working unit of the product is therefore reduced.

However, if this step 3530 determines that some portion of the process is not functioning within the predetermined defect and yield parameters as defined in the Manufacturing Database 2600, or any one of a number of predefined conditions are met, then the determination is NO, the process is not "Defect Free".

In this case, there may be at least two possible the next steps 3580, 3590 based on the results 3480, 3490 of the inspection process 3000. If one or more anomalies were cataloged in the previous step 3480 of inspection process 3000, one of the next steps 3580 comprises analyzing the detected anomalies, either manually or automatically using programs for defect analysis and pattern recognition. One example of such analysis may be tabulating the locations of a set of defects to identify a cluster that may indicate a piece of equipment is occasionally scratching a wafer. Although the individual pits and other defects individually may only appear locally random when considered one-by-one, an analysis of the cluster may reveal the characteristic pattern of a scratch.

Likewise, if one or more process corrections were recommended in the previous step 3490 of inspection process 3000, one of the next steps 3590 comprises tabulating the process corrections, either manually or automatically using programs for defect analysis and pattern recognition.

Once the steps of analyzing the anomalies 3580 and tabulating the corrections 3590 have been completed, the next step 3550 is an evaluation of the deviant conditions, either manually or by automated means using one or more computers, and a determination of what might be changed in the manufacturing process. For example, if scratches on wafers from one particular tool are being consistently detected, it may be recommended that the deviant tool may be removed from the manufacturing process until the indicated mechanical problem with the wafer handling stage can be fixed.

In the next step 3591, the changes are actually implemented in the manufacturing process. Corresponding changes to the data in the Manufacturing Database 3600 may also be made, so that the Database 3600 will now comprise recipes and specifications that have been updated with the new information.

Metrology and Inspection Variations.

Some embodiments of the invention may comprise additional variations of the elements of the metrology 2000 and inspection 3000 processes, as well as the associated methods for process control 2500 and yield management 3500.

Several embodiments of the invention can be used, depending on the imaging properties of the detector and the design of the stage that holds the object to be examined.

In some embodiments of the invention, multiple images of the object or portions thereof may be taken with different x-ray energy spectral distributions. These multiple images may be combined, subtracted or otherwise processed numerically to produce a new image that has can make potential defects more apparent.

In some embodiments of the invention, the images of the entire object to be investigated, or images of portions of the object to be investigated, or 3D reconstructions of the object to be investigated, can be compared to stored reference data, typically data representing a correctly manufactured object. The stored reference data can comprise previously collected images, or stored information representing what is expected for a correctly manufactured object, or a set of mathematical or geometric rules that a correctly manufactured object must follow.

In some embodiments of the invention, when discrepancies with the stored reference data are identified, further image processing and analysis can be carried out to attempt to classify the discrepancies as corresponding to particular types or classes of defects. In some embodiments of the invention, additional imaging at higher resolution or using additional imaging angles for the incident x-ray beam may be performed to further identify or characterize a potential defect.

In some situations, particularly with more elaborate structures such as multiple ICs or ICs and interposers stacked in a 2.5D or a 3D configuration, an embodiment of the invention can be used to examine the configuration prior to completing the bonding of the configuration, to insure the components have been correctly aligned. It can also be used as a component of a system to not only examine and inspect, but to align and bond these multi-chip structures.

In some situations, the inspection system may be used to align to objects before bonding or otherwise connecting them.

Some embodiments of the invention also include a method of manufacturing using the apparatus described in this specification.

Some embodiments of the invention also include devices manufactured using the apparatus described in this specification, in which the manufacturing process for the product uses the apparatus to maintain the process within a process window or above a certain product yield, and in which the process includes metrology or defect detection or statistical process control.

In some embodiments of the invention, the images and measurements may be used to adjust downstream processes in real time or near real time in order to improve manufacturing yields.

In some embodiments of the invention, the images and measurements may be used to identify process variations, variation in incoming materials, changes in the condition of manufacturing equipment, or changes in the manufacturing recipe or process set up into the manufacturing equipment.

In some embodiments of the invention, the images and measurements may be used to screen defective or non-complying materials from the manufacturing line to prevent further destruction of other materials such as expensive active silicon devices.

In some embodiments of the invention, the images and measurements may be used to check the alignment between a via in an interposer or chip and a capture pad on the surface of the interposer or chip. The capture pad may also be used as a connection to the next device or interposer.

In some embodiments of the invention, the images and measurements may be used to detect voids or the absence of fill material in vias so as to reject the parts from manufacturing, or to determine if the voids are a factor in the long-term reliability of the component or system.

In some embodiments of the invention, the images may be taken as part of an alignment process between a chip and an interposer prior to bonding or attaching the individual components. Based on these images, the process of alignment and bonding can be adjusted to improve the accuracy and quality of these connections. Other embodiments of the invention allow real time feedback to alignment tools in aligning dice or interposers.

In some embodiments of the invention, the images and measurements may be used to inspect the shape and dimensions of solder used to connect devices or interposers. These inspections may be used to control the manufacturing process or screen out defective material. The presence of some patterns of solder after bonding may be used to detect improper solder joints including joints in which the solder is not continuous between the two connection points and is therefore not a useful conductor of electricity or heat. In other embodiments, multiple solder reflow processes may be utilized to repair or improve solder connections that are determined to be non-complying with manufacturing or product specifications based on results of inspection with the system according to the invention.

In some embodiments of the invention, the images and measurements may be used to determine the relative deviation in position and dimensions of multiple layers of metal lines, bumps, pads, or connecting layers in a stack of chips and interposers.

Advantages of the Invention: Inspection Speed.

A significant advantage of this invention is that an extended source of x-rays can be used, increasing the available flux of x-rays used for imaging. This in turn increases the throughput possible for the system. Put another way, in the time to acquire a single inspection image with a PPM system, the proposed invention can acquire over 300,000 images with the same resolution.

Consider the following comparison with the PPM x-ray system. The time to acquire an image depends on the flux $\Phi$ of x-rays:

$$T_{acquire} = (P_\# \times X_P)/\Phi$$

where $P_\#$ is the number of pixels, $X_P$ is the number of x-rays per pixel, and $\Phi$ is the x-ray flux. The x-ray flux from a point source is:

$$Flux = \Phi = \beta \times \Omega \times S_A$$

where $\beta$ is the point source brightness, $\Omega$ is the angular distribution in mrad$^2$ and $S_A$ is the point source area $S_A = \pi r^2$. The source spot size for x-ray systems is typically defined using the ASTM standard SE-1165 ["Standard Test Method for Measurement of Focal Spots of Industrial X-Ray Tubes by Pinhole Imaging," ASTM Committee E-7 on Nondestructive Testing, May 15, 1992].

A typical x-ray source brightness $\beta$ is $$\beta = 10^8 \text{ x-rays/sec/mm}^2/\text{mrad}^2.$$

To avoid parallax errors in automated inspection, the PPM x-ray beam should be well collimated; a divergence of 20 mrad is typical. For a point source with $$\Omega = (20 \text{ mrad})^2 = 400 \text{ mrad}^2$$

and a source spot diameter $d = 2r = 1$ μm $= 10^{-3}$ mm, the flux is given by:

$$\begin{aligned}
Flux = \Phi &= \beta \times \Omega \times S_A \\
&= 10^8 \times 400 \times \pi \times [0.5 \times 10^{-3}]^2 \text{ x-rays/sec} \\
&= 400 \times \pi \times 0.25 \times 10^8 \times [10^{-3}]^2 \text{ x-rays/sec} \\
&= 400 \times \pi \times 25 \text{ x-rays/sec} \\
&= 31{,}416 = 3.14 \times 10^4 \text{ x-rays/sec.}
\end{aligned}$$

A typical x-ray image sensor may have 512×512 pixels that need 1,000 x-rays/pixel for image formation. An image for a PPM system will therefore be collected in approximately 8,350 seconds, or 2.3 hours.

On the other hand, keeping the same source brightness, but illuminating with a larger source spot size according to the invention dramatically increases the x-ray flux illuminating the object. As an example, assume a source with a 1 mm diameter (r=0.5 mm) separated by 100 mm from the object and, furthermore, assume that the distance from the object to scintillator is 100 microns. The angular divergence of the x-ray beam is given by:

$$\alpha = 1 \text{ mm}/100 \text{ mm} = 10 \text{ mrad,}$$

making $$\Omega = 100 \text{ mrad}^2.$$

The spot area is $= \pi \times [0.5]^2 = 0.785$ mm$^2$, so the flux becomes:

$$\begin{aligned}
Flux = \Phi &= 10^8 \times 100 \times 0.785 \text{ photons/sec} \\
&= 7.85 \times 10^9 \text{ photons/sec}
\end{aligned}$$

which is higher than the PPM configuration by a factor of 250,000 times. Therefore, the same 512×512 image (with 1,000 x-rays per pixel) can now be produced at high speed and, for example, may now have a proportionally faster image collection time of approximately 33 msec.

As a practical matter, the throughput enhancement may be further reduced by a factor of between 2 and 10 from this number. A PPM imaging system can detect x-rays in the enlarged shadow image directly with a CCD x-ray detector, which can have a quantum efficiency between 50% to 100%. The typical x-ray CCD array comprises an array of pixels, with a pixel size of approximately 100 μm×100 μm.

In comparison, the high-resolution direct-shadow images for the system of the disclosed invention come from an extended x-ray source, and are not magnified. The pixels of contemporary x-ray imaging detectors are far too large to resolve the proximity images. Instead, the invention disclosed here comprises a scintillator to convert the x-rays to optical photons, and then magnifies this optical image.

In order to achieve a particular resolution, there may be thickness specifications for the scintillator. For a resolution of 1 micron, for example, the scintillator may have a specified thickness between 1 and 10 microns. For thin scintillators, some of the incident x-rays will pass through the scintillator without being absorbed. Therefore, the quantum efficiency of this conversion process may worse than the PPM system, emitting visible photons for approximately 20% of the x-rays passing through the scintillator. Beyond this, the microscope may lose additional photons, depending on the optical system NA and the quantum efficiency of the visible CCD detector. However, even with these losses, the benefit provided by the higher flux of the extended source still provides a significant advantage.

Advantages of the Invention: Imaging Resolution.

The resolution of the prior art PPM system is determined by the spot size of the x-ray source. For example, a source with a 1 micron spot size will produce images with 1 micron resolution, assuming the system is operating at optimal resolution. Practically speaking, it is difficult to achieve resolution much below 1 micron with a PPM system, due to rapidly decreasing efficiency of the x-ray source for small spot sizes. As the spot size of the x-ray source decreases, the x-ray power must be reduced to avoid melting the x-ray target. Furthermore, the x-ray target must be made thinner, to reduce scattering in the target. As a result, for each 2× decrease in spot size, the flux from the source decreases a factor of about 10×.

For the imaging system according to the invention, the scintillator is in close proximity to the object being examined, and photons emitted are in proportion to the x-rays. For the optical system that relays the photons emitted by the scintillator to the detector, assuming a scintillator emission wavelength of $\lambda = 535$ nm and a solid immersion optical system with NA≈1.75 comprising LuAG optical elements with refractive index n=1.84, the definition for the diffraction-limited resolution R of the optical system relaying scintillator photons to the detector is:

$$R = \frac{\lambda}{2 * NA} = \frac{535 \text{ nm}}{2 * 1.75} = 153 \text{ nm}$$

which is 6.5 times smaller than the 1 micron resolution of the PPM system.

Figure 30:
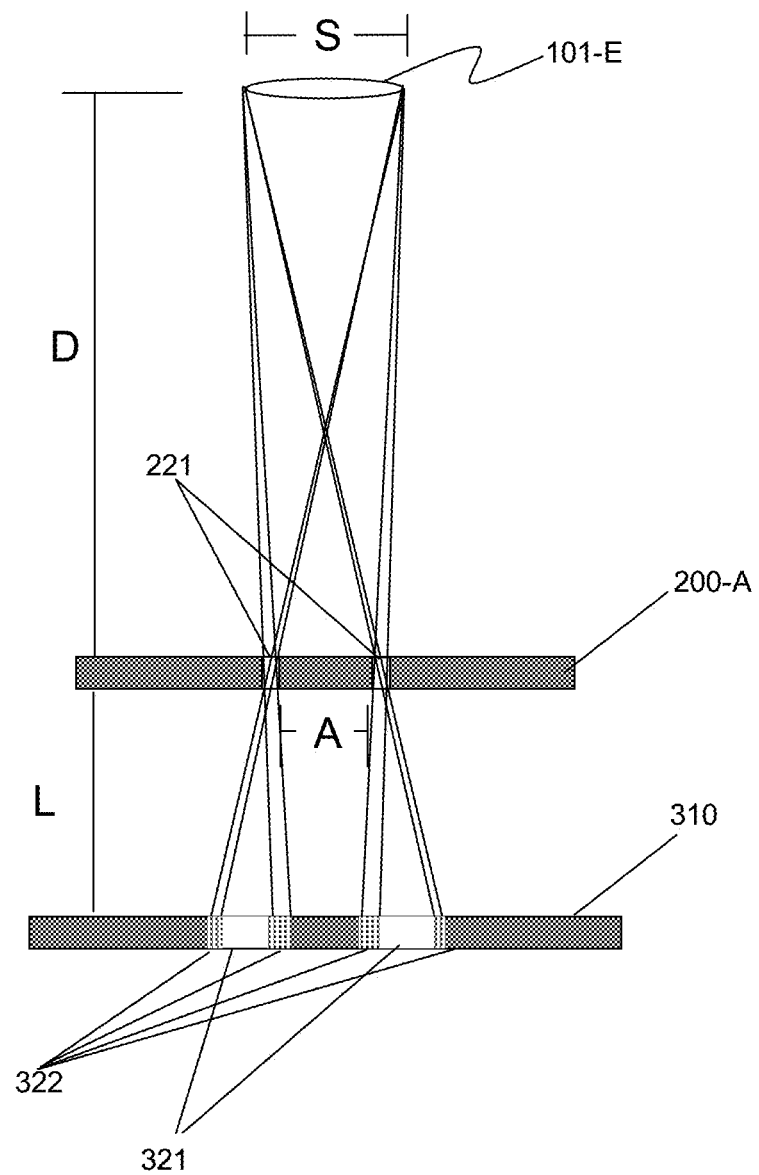
FIG. 30 illustrates an example of resolution and blur in a system according to the invention.

Resolution is not only limited by the optical system, however. When using an extended source, as with the PPM system, distortion and blur in the projected shadows can still occur. FIG. 30 illustrates a system according to the invention with a geometric projection of x-rays from an extended source 101-E of width S onto an object 200-A with two apertures 221 separated by a distance A. The distance from the extended source 101-E to the object 200-A is given by D, and the distance from the object 200-A to the scintillator 310 is given by L. Depending on the ratio of L and D, some magnification can occur, so in a preferred embodiment, D is much greater than L, and L is typically 1 mm or smaller. In some embodiments, L will be 100 microns or smaller, with the scintillator placed as close to the object as practically possible. In some embodiments, L will be 0 microns, and the object 200-A and scintillator 310 or scintillator assembly 300 will be in contact.

The bright spots of x-rays 321 on the scintillator 310 that correspond to the apertures 221 will have some blur 322 at the edges, depending on the size S of the extended source 101-E and the distances D and L. The two spots with separation A can be resolved if $$A \geq \frac{L}{D} S$$

For L=100 μm, D=10 cm, and S=1 mm, the minimum resolvable distance A=1 μm, comparable to the PPM system. For L=25 μm, D=10 cm, and S=0.5 mm, the minimum resolvable distance A=125 nm, smaller than the estimated resolution of the optical system.

In general, as a practical matter, a system will have adequate resolution if the contrast between two adjacent black and white objects (a line and a space) produces a modulation transfer function (MTF) greater than 5%

Clearly, these parameters can be optimized for certain circumstances and embodiments, as can the design of the optical microscope system, to produce a system with high-resolution at high speed while minimizing cost.

Advantages of the Invention: Time to Market.

The high speed at which non-destructive images at resolutions smaller than 50 microns can be gathered can improve the time to market for the development of manufacturing processes such as the flip chip interconnect (FCI) process described earlier. The destructive processes for failure analysis, also described earlier, can take weeks to collect a single image, and months to acquire statistical data on parts. Because of the rapid time in which images can be collected and analyzed using the system of the present invention, process development time for such products can be counted in days, and is typically a fraction of the total time required to design and bring to market a new product.

Furthermore, because of the enhanced resolution, the present invention can be used for the new FCI processes with pitches smaller than 50 microns. The present invention can be used for significantly smaller pitches, and still maintain the desired image resolution and speed.

In terms of the product development cycle, an increase in time for feedback of one to several weeks has a distinct and significant impact on the time required to develop a new product. In a simple case, perhaps three to five cycles of setup and data collection may be sufficient to establish a process for a new device. In a more complex case, such as a high-density interposer or a 3D IC, tens or hundreds of iterations may be required. Without the present invention, each of these cycles may take several weeks, and the total time to market of the product may come to be dominated by these cycles. Clearly a method of determining the quality of fine pitch (50 microns and smaller) bonds at the time of processing offers a significant advantage.

The images and calculations produced by the system and methods disclosed herewith allow the quality of bonds to be examined immediately after bonding in a matter of seconds or minutes.

In order to develop and qualify a new semiconductor product for mass production, many individual processes and the integration of these processes must be established, tuned, and tested. In the case of forming a through-silicon via (TSV) in a semiconductor wafer, the process flow typically requires that the vias be formed first and the capture pads be subsequently formed on the wafer surface over the vias. Since the capture pads obscure optical inspection of the vias themselves, in the absence of the present invention, the alignment between the vias and the capture pads may not be accurately determined at the time of manufacturing without cutting the silicon wafer and inspecting this feature in cross-section. Since this procedure is time consuming and also destroys the silicon wafer and any economic value contained within it, it is therefore undesirable.

In the case of bonding two or more chips or substrates or even complete wafers together using FCI, the alignment, bonding force, bonding temperature, rate of heating, and rate of cooling among other factors must be tightly controlled. While control of manufacturing equipment and processes can enable some of the necessary control, inspection and measurement of features within the product that are not optically visible may also be required. Without the use of the apparatus disclosed in this invention, assembled parts must be cross-sectioned in order to be inspected. Given the fine pitch of the interconnect bonds and the very large quantity of connections, this procedure can take several weeks. Even so, typically only a very small subset of the total interconnect bonds may actually be inspected.

The inability to inspect bonds quickly can add significantly to the length of time required to fine tune both individual process steps as well as the integration of multiple process steps to create a finished product.

For example, consider a case where 25 iterations of the bonding process are required to develop and qualify a product. In the case without the apparatus disclosed in this invention, each iteration may require 1 week to build each group of samples under various process and tooling configurations. After manufacturing a group of samples, an additional 2 weeks may be required to cross-section individual units and inspect the quality and attributes of the bonds that have been created. The total time is therefore:

25 cycles×(1 week making+2 weeks inspection)= 75.0 weeks.

With the use of the apparatus disclosed in this invention, the 2 weeks of inspection can be reduced to a few minutes by eliminating the need for time consuming cross-sectioning. The total time for the sequential cycles may now be calculated as:

25 cycles×(1 week making+1 hour inspection)=25.15 weeks, a reduction by 49.85 weeks (or 66% of the initial time to market).

With high-volume consumer electronic devices such as mobile phones selling in volumes of more than 100 million units a year, it can be easily seen that a decrease in time to market by 50 weeks (almost one year) can have significant impact on the market.

The apparatus may further be integrated into the bonding tool or via filling tool, for example the electrochemical deposition tool, to provide feedback to the bonding process in real time. The use of the apparatus in this way reduces time to market by many weeks and may in fact enable a product to enter the market that otherwise would be too costly or too late to market to have economic value.
Advantages of the Invention: Product Yield and Cost.

Currently, active silicon devices mounted onto a fine pitch silicon interposer with a bump pitch of around 50 microns have been demonstrated, but have not achieved high volume manufacture or acceptable yields. A well known case at this time is the Xilinx Virtex 7 chip. This chip has 4 homogeneous processors mounted onto one silicon interposer <http://www.xilinx.com/products/silicon-devices/3dic/index.htm>. The application of this device is in high-speed network processors, where selling prices are at the very highest end of the semiconductor market. It has been reported that commercial production began on these devices with overall yields related to package assembly and interconnect in the range of 80%. This yield is far lower than typically accepted in the semiconductor field, and there is considerable additional cost associated with the scrap material. However, this particular part was determined to have such high commercial value that, even considering the cost associated with low yield, it was commercially feasible to produce with only 80% package assembly yield.

In other lower-cost, more consumer-oriented segments of the market, pressure on pricing is much more intense, and it is unlikely that a product with package assembly yields at this level could be commercially viable. For this reason, it is necessary for the manufacturing process to be highly capable and tightly controlled, such that the amount of scrap product or yield loss resulting from the bonding process is reduced. Traditionally, package assembly yields are in the 98 to 99% range. Those skilled in the art will quickly realize that scrapping good chips by using poorly yielding bonding techniques, and packaging yields of 80% for lower value chips, are simply not acceptable.

It should be noted that, in the case of multiple dice mounted together either as a 3D IC or onto a high-density interposer, the failure of one connection on any chip will result in the scrapping of the entire MCP or package assembly. There may be thousands or tens of thousands of connections that must all function as designed. It is rare that any kind of rework or recovery of materials can be accomplished if any of the bonds are not produced correctly.

For example, take the case when a processor chip with a cost of $10 is mounted together with four memory chips costing $5 each, or $20. The total cost of the chips is therefore $30. Chip assembly and packaging may add another $5 of cost for a total assembly cost of $35.

In the case where the assembly yield for these parts is 80%, for each 100 sets of chips, 20 will be scrapped. The manufacturing cost for 100 units is given by:

Cost=[$10+(4×$5)+$5]×100=$3,500.

However, with only 80% of the assemblies being functional, the total cost per working assembly will be:

$$\text{Cost/unit} = \frac{\$3{,}500}{80} = \$43.75$$

which is 24% more expensive than a process yielding 99% would provide. This cost increase may consume the entire profit margin for some low-end products, and in any case represents an undesirable outcome.

By using the images and measurements produced by the apparatus in this disclosure, the processes of aligning, inspection bonding can be controlled and monitored such that the yield can be rapidly increased. For MCP packages, in the example above, detecting a flaw between the first two dice will allow the packaging assembler to scrap the first two die only, and not require the loss of all five dice, therefore saving scrap costs and improving yield. It is common for well-controlled and monitored assembly processes to have yields of over 99.9%. The present invention allows a packaging assembler to achieve a yield of greater than or equal to 90% in MCP structures having more than 4 dice and having more than 100 TSVs per interposer or die layer at pitches where the smallest pitch is less than 100 microns. The same yield advantage may be achieved in the flip chip configuration having more than 400 microbumps at a pitch where the smallest pitch is less than 100 microns.

This same advantage in cost and yield can be seen at other steps in the manufacturing process for fine-pitch interposers and 3D die stacking, such as via fill monitor for voids, via capture pad alignment to via, alignment of chip-bump to chip or interposer pad, and quality of completed joint after bonding. It may also be used to measure bondline in the assembly of multiple slices of silicon devices or fine pitch interposers or between silicon devices and other materials of interest where this bondline thickness is critical to device performance.

Embodiments and Limitations

With this application, several embodiments of the invention, including the best modes for various circumstances, have been disclosed. While specific materials, designs, configurations and fabrication steps have been set forth to describe this invention and the preferred embodiments, such descriptions are not intended to be limiting. Modifications and changes may be apparent to those skilled in the art, and it is intended that this invention be limited only by the scope of the appended claims.

I claim:

1. An improved multi-chip integrated circuit device package comprising semiconductor devices with through-silicon-vias (TSVs) and having bump pitches of less than or equal to 100 microns, the improved multi-chip integrated circuit device package being produced with a yield of greater than 90% based on inspections by a high-speed inline x-ray inspection tool of a plurality of prior multi-chip integrated circuit device packages, the improved multi-chip integrated circuit device package being produced by a process comprising the steps of:

inspecting the plurality of prior multi-chip integrated circuit device packages with the high-speed inline x-ray inspection tool, wherein the tool comprises:
a source of x-rays,
a mount for holding the integrated circuit device package,
a scintillator that absorbs x-rays and emits visible photons,
an optical system that forms a magnified image of the scintillator, and
a means of converting the magnified image of the emitted photons into electronic signals;

detecting, based on the high-speed inline x-ray inspection, whether one or more process variations are present in one or more of the plurality of prior multi-chip integrated circuit device packages;

modifying, responsive to the detection of one or more process variations, one or more steps of the production process to reduce the process variations; and producing, using the modified production process, the improved multi-chip integrated circuit device package, wherein the modified production process achieves the yield of greater than 90%.

2. The improved multi-chip integrated circuit device package of claim 1, in which the device package comprises components selected from the group consisting of:
an interposer, a silicon interposer, a silicon dioxide interposer, an integrated circuit, a semiconductor wafer, a silicon wafer, a wafer comprising TSVs, a printed circuit board, a 3D IC package, a 2.5D IC package, and a multi-chip-module.

3. The improved multi-chip integrated circuit device package of claim 1, wherein during the inspection of the plurality of prior multi-chip integrated circuit device packages with x-rays:
the integrated circuit device package is has been placed in the mount for holding the integrated circuit device package;
and the distance between the scintillator and the integrated circuit device package is less than 1 mm.

4. The improved multi-chip integrated circuit device package of claim 1, wherein during the inspection of the plurality of prior multi-chip integrated circuit device packages with x-rays:
the emission of x-rays occurs from a spot with a diameter greater than 10 micrometers formed by the collision of an electron beam with an anode;
and the ratio of the spot size of the x-ray source and the resolution of the optical system is greater than 20.

5. The integrated circuit device package of claim 1, wherein the tool further comprises:
a means for adjusting the position of the source of x-rays such that the source spot of an x-ray emitter within the source of x-ray is not on the optical axis of the optical system.

6. The improved multi-chip integrated circuit device package of claim 1, wherein the process further comprises the steps of:
selecting an integrated circuit device package for measurement;
forming at least one image of the a portion of the package using the tool, wherein the tool further comprises a means of storing the electronic signals corresponding to the image;
analyzing the electronic signals corresponding to the image with a predetermined recipe;
determining at least one physical dimension for a component of the package; and
displaying the at least one physical dimension.

7. The integrated circuit device package of claim 1, wherein the process further the steps of:
selecting a first multi-chip integrated circuit device package for inspection from among the plurality of prior multi-chip integrated circuit device packages;
forming at least one image of the first multi-chip integrated circuit device package using the tool, wherein the tool further comprises a means of storing the electronic signals corresponding to the image;
analyzing the electronic signals corresponding to the image with a predetermined recipe for identification of the process variations; and
displaying the results of the process variation analysis.

8. An improved multi-chip integrated circuit device package comprising semiconductor devices with silicon interposers, through-silicon-vias (TSVs), and having more than 4 dice and more than to 100 TSVs per interposer at pitches where the smallest pitch is less than 100 microns, the improved multi-chip integrated circuit device package being produced with a yield of greater than 90% based on inspections by a high-speed inline x-ray inspection tool of a plurality of prior multi-chip integrated circuit device packages, the improved multi-chip integrated circuit device package being produced by a process comprising the steps of:
inspecting, inline to the production process, one or more dimensions of each of the plurality of prior multi-chip integrated circuit device packages with the high-speed x-ray inspection tool;
detecting, based on the high-speed inline x-ray inspection, whether one or more process variations are present in one or more of the prior multi-chip integrated circuit device packages;
modifying, responsive to the detection of one or more process variations, one or more steps of the production process to reduce the detected process variations; and
producing, using the modified production process, the improved multi-chip integrated circuit device package, wherein the modified production process achieves the yield of greater than 90%.

9. An improved multi-chip integrated circuit device package in a flip chip configuration comprising semiconductor devices having more than 400 microbumps at pitches where the smallest pitch is less than 100 microns, the improved multi-chip integrated circuit device package being produced with a yield of greater than 90% based on inspections by a high-speed inline x-ray inspection tool of a plurality of prior multi-chip integrated circuit device packages, the improved multi-chip integrated circuit device package being produced by a process comprising the steps of:
inspecting, inline to the production process, one or more dimensions of each of the plurality of prior multi-chip integrated circuit device packages with the high-speed x-ray inspection tool;
detecting, based on the high-speed inline x-ray inspection, whether one or more process variations are present in one or more of the prior multi-chip integrated circuit device packages;
modifying, responsive to the detection of one or more process variations, one or more steps of the production process to reduce the detected process variations; and
producing, using the modified production process, the improved multi-chip integrated circuit device package, wherein the modified production process achieves the yield of greater than 90%.

10. An improved multi-chip integrated circuit device package comprising semiconductor devices with through-silicon-vias (TSVs) and having bump pitches of less than or equal to 100 microns, the improved multi-chip integrated circuit device package being produced with a yield increase of at least 10% based on inspections by a high-speed inline x-ray inspection tool of a plurality of prior multi-chip integrated circuit device packages, the improved multi-chip integrated circuit device package being produced by a process comprising the steps of:
inspecting, inline to the production process, one or more dimensions of each of the plurality of prior multi-chip integrated circuit device packages with the high-speed x-ray inspection tool;
detecting, based on the high-speed inline x-ray inspection, whether one or more process variations are present in one or more of the prior multi-chip integrated circuit device packages;

modifying, responsive to the detection of one or more process variations, one or more steps of the production process to reduce the detected process variations; and producing, using the modified production process, the improved multi-chip integrated circuit device package, wherein the modified production process achieves the yield increase of at least 10%.

11. The improved multi-chip integrated circuit device package of claim 10, wherein the high-speed x-ray inspection tool has an imaging speed sufficient to operate inline to a commercial high-throughput integrated circuit and electronic packaging inspection process.

12. The improved multi-chip integrated circuit device package of claim 10, wherein the high-speed x-ray inspection tool has an imaging speed between approximately 33 milliseconds and 2 seconds.

13. The improved multi-chip integrated circuit device package of claim 10, wherein the high-speed x-ray inspection tool has an imaging speed between approximately 2 second and 2 minutes.

14. The improved multi-chip integrated circuit device package of claim 10, wherein the high-speed x-ray inspection tool has an imaging speed between approximately 30 images/second and 30 images/hour.

15. The improved multi-chip integrated circuit device package of claim 10, wherein inspecting the one or more dimensions of each of the plurality of prior multi-chip integrated circuit device packages with the high-speed x-ray inspection tool comprises, for each prior multi-chip integrated circuit device package:
   selecting a position on the prior multi-chip integrated circuit device package for measurement;
   mounting the prior multi-chip integrated circuit device package in the high-speed x-ray inspection tool;
   gathering one or more x-ray images from the high-speed x-ray inspection tool;
   calculating measurements from the x-ray images; and
   outputting measurement results.

16. The improved multi-chip integrated circuit device package of claim 10, wherein the improved multi-chip integrated circuit device package is produced by a process further comprising the steps of:
   specifying the production process; and
   fabricating one or more of the prior multi-chip integrated circuit device packages according to a design specified by the production process; and
   modifying, responsive to the detection of one or more process variations, one or more featured of the design to reduce the detected process variations.

17. The improved multi-chip integrated circuit device package of claim 10, wherein detecting whether one or more process variations are present in one or more of the prior multi-chip integrated circuit device packages:
   determining whether one or more steps of the production process are functioning within predetermined parameters defined in a specification database.

18. The improved multi-chip integrated circuit device package of claim 10, wherein inspecting the one or more dimensions of each of the plurality of prior multi-chip integrated circuit device packages with the high-speed x-ray inspection tool comprises, for each prior multi-chip integrated circuit device package:
   selecting a position on the prior multi-chip integrated circuit device package for measurement;
   mounting the prior multi-chip integrated circuit device package in the high-speed x-ray inspection tool;
   gathering one or more x-ray images from the high-speed x-ray inspection tool;
   comparing the one or more x-ray images to one or more reference images in a reference database;
   outputting comparison results.

19. The improved multi-chip integrated circuit device package of claim 10, wherein the high-speed inline x-ray inspection tool comprises:
   a source of x-rays,
   a mount for holding the integrated circuit device package,
   a scintillator that absorbs x-rays and emits visible photons,
   an optical system that forms a magnified image of the scintillator, and
   a means of converting the magnified image of the emitted photons into electronic signals.

20. The improved multi-chip integrated circuit device package of claim 10, wherein modifying one or more steps of the production process to reduce the detected process variations comprises adjusting an alignment of one or more components of the improved multi-chip integrated circuit device package based on the detection of one or more process variations in one or more of the plurality of prior multi-chip integrated circuit device packages.

21. The improved multi-chip integrated circuit device package of claim 10, wherein modifying one or more steps of the production process to reduce the detected process variations comprises:
   using statistical process control to identify one or more improvements to the production process; and
   adjusting one or more parameters of the production process based on the identified improvements.

22. The improved multi-chip integrated circuit device package of claim 10, wherein the one or more process variations comprise one or more defects or failure modes.

23. The improved multi-chip integrated circuit device package of claim 10, wherein the one or more process variations comprise one or more process variables drifting out of specification.

24. The improved multi-chip integrated circuit device package of claim 10, wherein the plurality of prior multi-chip integrated circuit device packages comprises multi-chip integrated circuit device packages inspected by high-speed inline x-ray inspection tool at a time prior to the production of the improved multi-chip integrated circuit device package.

* * * * *